(12) United States Patent
Giobbi et al.

(10) Patent No.: US 11,727,355 B2
(45) Date of Patent: *Aug. 15, 2023

(54) PROXIMITY-BASED HEALTHCARE MANAGEMENT SYSTEM WITH AUTOMATIC ACCESS TO PRIVATE INFORMATION

(71) Applicant: Proxense, LLC, Bend, OR (US)

(72) Inventors: John J. Giobbi, Bend, OR (US); Ryan Gallivan, Bend, OR (US); Kent Yundt, Bend, OR (US)

(73) Assignee: PROXENSE, LLC, Bend, OR (US)

( * ) Notice: Subject to any disclaimer, the term of this patent is extended or adjusted under 35 U.S.C. 154(b) by 243 days.

This patent is subject to a terminal disclaimer.

(21) Appl. No.: 17/208,120

(22) Filed: Mar. 22, 2021

(65) Prior Publication Data
US 2021/0210178 A1 Jul. 8, 2021

Related U.S. Application Data

(63) Continuation of application No. 13/942,549, filed on Jul. 15, 2013, now Pat. No. 10,971,251, which is a (Continued)

(51) Int. Cl.
*G16H 10/60* (2018.01)
*G06Q 10/10* (2023.01)

(52) U.S. Cl.
CPC .............. *G06Q 10/10* (2013.01); *G16H 10/60* (2018.01)

(58) Field of Classification Search
CPC ................................ G06Q 10/10; G16H 10/60
(Continued)

(56) References Cited

U.S. PATENT DOCUMENTS

| 3,665,313 A | 5/1972 | Trent |
| 3,739,329 A | 6/1973 | Lester |

(Continued)

FOREIGN PATENT DOCUMENTS

| EP | 1536306 A1 | 6/2005 |
| JP | 10-049604 A | 2/1998 |

(Continued)

OTHER PUBLICATIONS

Liu et al., "A Practical Guide to Biometric Security Technology," IT Pro, vol. 3, No. 1, Jan./Feb. 2001, pp. 27-32.
(Continued)

*Primary Examiner* — Jason S Tiedeman
(74) *Attorney, Agent, or Firm* — Patent Law Works LLP; Greg T. Sueoka

(57) ABSTRACT

A healthcare management system and method provide efficient and secure access to private information. A portable physical device, referred to herein as a Personal Digital Key or "PDK", stores one or more profiles in memory. The biometric profile is acquired in a secure trusted process and is uniquely associated with an individual that is authorized to use and is associated with the PDK. The PDK can wirelessly transmit the identification information including a unique PDK identification number and the biometric profile over a secure wireless channel for use in an authentication process. The PDK is configured to wirelessly communicate with a reader. A provider interface coupled to the reader, and the reader is further configured to receive profile information from the PDK. The healthcare management system also includes an auto login server configured to communicate with the provider interface to allow access to information in a patient database.

20 Claims, 41 Drawing Sheets

Related U.S. Application Data continuation of application No. 12/371,170, filed on Feb. 13, 2009, now Pat. No. 8,508,336.

(60) Provisional application No. 61/102,987, filed on Oct. 6, 2008, provisional application No. 61/090,878, filed on Aug. 21, 2008, provisional application No. 61/090,234, filed on Aug. 20, 2008, provisional application No. 61/075,117, filed on Jun. 24, 2008, provisional application No. 61/028,847, filed on Feb. 14, 2008.

(58) Field of Classification Search
USPC .................................................. 705/2, 3
See application file for complete search history.

(56) References Cited

U.S. PATENT DOCUMENTS

| | | | |
|---|---|---|---|
| 3,761,883 | A | 9/1973 | Alvarez et al. |
| 3,906,166 | A | 9/1975 | Cooper et al. |
| 4,101,873 | A | 7/1978 | Anderson et al. |
| 4,430,705 | A | 2/1984 | Cannavino et al. |
| 4,476,469 | A | 10/1984 | Lander |
| 4,598,272 | A | 7/1986 | Cox |
| 4,661,821 | A | 4/1987 | Smith |
| 4,759,060 | A | 7/1988 | Hayashi et al. |
| 4,814,742 | A | 3/1989 | Morita et al. |
| 4,871,997 | A | 10/1989 | Adriaenssens et al. |
| 4,993,068 | A | 2/1991 | Piosenka et al. |
| 5,043,702 | A | 8/1991 | Kuo |
| 5,052,049 | A | 9/1991 | Andros et al. |
| 5,187,352 | A | 2/1993 | Blair et al. |
| 5,224,164 | A | 6/1993 | Elsner |
| 5,296,641 | A | 3/1994 | Stelzel |
| 5,307,349 | A | 4/1994 | Shloss et al. |
| 5,317,572 | A | 5/1994 | Satoh |
| 5,325,285 | A | 6/1994 | Araki |
| 5,392,287 | A | 2/1995 | Tiedemann et al. |
| 5,392,433 | A | 2/1995 | Hammersley et al. |
| 5,410,588 | A | 4/1995 | Ito |
| 5,416,780 | A | 5/1995 | Patel |
| 5,422,632 | A | 6/1995 | Bucholtz et al. |
| 5,428,684 | A | 6/1995 | Akiyama et al. |
| 5,450,489 | A | 9/1995 | Ostrover et al. |
| 5,473,690 | A | 12/1995 | Grimonprez et al. |
| 5,481,265 | A | 1/1996 | Russell |
| 5,506,863 | A | 4/1996 | Meidan et al. |
| 5,517,502 | A | 5/1996 | Bestler et al. |
| 5,541,583 | A | 7/1996 | Mandelbaum |
| 5,544,321 | A | 8/1996 | Theimer et al. |
| 5,552,776 | A | 9/1996 | Wade et al. |
| 5,563,947 | A | 10/1996 | Kikinis |
| 5,589,838 | A | 12/1996 | Mcewan |
| 5,594,227 | A | 1/1997 | Deo |
| 5,598,474 | A | 1/1997 | Johnson |
| 5,611,050 | A | 3/1997 | Theimer et al. |
| 5,615,277 | A | 3/1997 | Hoffman |
| 5,619,251 | A | 4/1997 | Kuroiwa et al. |
| 5,623,552 | A | 4/1997 | Lane |
| 5,629,980 | A | 5/1997 | Stefik et al. |
| 5,644,354 | A | 7/1997 | Thompson et al. |
| 5,666,412 | A | 9/1997 | Handelman et al. |
| 5,689,529 | A | 11/1997 | Johnson |
| 5,692,049 | A | 11/1997 | Johnson et al. |
| 5,719,387 | A | 2/1998 | Fujioka |
| 5,729,237 | A | 3/1998 | Webb |
| 5,760,705 | A | 6/1998 | Glessner et al. |
| 5,760,744 | A | 6/1998 | Sauer |
| 5,773,954 | A | 6/1998 | Vanhorn |
| 5,784,464 | A | 7/1998 | Akiyama et al. |
| 5,799,085 | A | 8/1998 | Shona |
| 5,821,854 | A | 10/1998 | Dorinski et al. |
| 5,825,876 | A | 10/1998 | Peterson, Jr. |
| 5,835,595 | A | 11/1998 | Fraser et al. |
| 5,838,306 | A | 11/1998 | O'Connor et al. |
| 5,854,891 | A | 12/1998 | Postlewaite et al. |
| 5,857,020 | A | 1/1999 | Peterson, Jr. |
| 5,886,634 | A | 3/1999 | Muhme |
| 5,892,825 | A | 4/1999 | Mages et al. |
| 5,892,900 | A | 4/1999 | Ginter et al. |
| 5,894,551 | A | 4/1999 | Huggins et al. |
| 5,898,880 | A | 4/1999 | Ryu |
| 5,910,776 | A | 6/1999 | Black |
| 5,917,913 | A | 6/1999 | Wang |
| 5,923,757 | A | 7/1999 | Hocker et al. |
| 5,928,327 | A | 7/1999 | Wang et al. |
| 5,942,985 | A | 8/1999 | Chin |
| 5,991,399 | A | 11/1999 | Graunke et al. |
| 5,991,749 | A | 11/1999 | Morrill, Jr. |
| 6,016,476 | A | 1/2000 | Maes et al. |
| 6,018,739 | A | 1/2000 | Mccoy et al. |
| 6,025,780 | A | 2/2000 | Bowers et al. |
| 6,035,038 | A | 3/2000 | Campings et al. |
| 6,035,329 | A | 3/2000 | Mages et al. |
| 6,038,334 | A | 3/2000 | Hamid |
| 6,038,666 | A | 3/2000 | Hsu et al. |
| 6,040,786 | A | 3/2000 | Fujioka |
| 6,041,410 | A | 3/2000 | Hsu et al. |
| 6,042,006 | A | 3/2000 | Van Tilburg et al. |
| 6,045,039 | A | 4/2000 | Stinson et al. |
| 6,055,314 | A | 4/2000 | Spies et al. |
| 6,068,184 | A | 5/2000 | Barnett |
| 6,069,647 | A | 5/2000 | Sullivan et al. |
| 6,070,796 | A | 6/2000 | Sirbu |
| 6,076,164 | A | 6/2000 | Tanaka et al. |
| 6,088,450 | A | 7/2000 | Davis et al. |
| 6,088,730 | A | 7/2000 | Kato et al. |
| 6,104,290 | A | 8/2000 | Naguleswaran |
| 6,104,334 | A | 8/2000 | Allport |
| 6,110,041 | A | 8/2000 | Walker et al. |
| 6,121,544 | A | 9/2000 | Petsinger |
| 6,134,283 | A | 10/2000 | Sands et al. |
| 6,137,480 | A | 10/2000 | Shintani |
| 6,138,010 | A | 10/2000 | Rabe et al. |
| 6,148,142 | A | 11/2000 | Anderson |
| 6,148,210 | A | 11/2000 | Elwin et al. |
| 6,161,179 | A | 12/2000 | Seidel |
| 6,175,921 | B1 | 1/2001 | Rosen |
| 6,177,887 | B1 | 1/2001 | Jerome |
| 6,185,316 | B1 | 2/2001 | Buffam |
| 6,189,105 | B1 | 2/2001 | Lopes |
| 6,209,089 | B1 | 3/2001 | Selitrennikoff et al. |
| 6,219,109 | B1 | 4/2001 | Raynesford et al. |
| 6,219,439 | B1 | 4/2001 | Burger |
| 6,219,553 | B1 | 4/2001 | Panasik |
| 6,237,848 | B1 | 5/2001 | Everett |
| 6,240,076 | B1 | 5/2001 | Kanerva |
| 6,247,130 | B1 | 6/2001 | Fritsch |
| 6,249,869 | B1 | 6/2001 | Drupsteen et al. |
| 6,256,737 | B1 | 7/2001 | Bianco et al. |
| 6,266,415 | B1 | 7/2001 | Campings et al. |
| 6,270,011 | B1 | 8/2001 | Gottfried |
| 6,279,111 | B1 | 8/2001 | Jensenworth et al. |
| 6,279,146 | B1 | 8/2001 | Evans et al. |
| 6,295,057 | B1 | 9/2001 | Rosin et al. |
| 6,307,471 | B1 | 10/2001 | Xydis |
| 6,325,285 | B1 | 12/2001 | Baratelli |
| 6,336,121 | B1 | 1/2002 | Lyson et al. |
| 6,336,142 | B1 | 1/2002 | Kato et al. |
| 6,343,280 | B2 | 1/2002 | Clark |
| 6,345,347 | B1 | 2/2002 | Biran |
| 6,363,485 | B1 | 3/2002 | Adams et al. |
| 6,367,019 | B1 | 4/2002 | Ansell et al. |
| 6,369,693 | B1 | 4/2002 | Gibson |
| 6,370,376 | B1 | 4/2002 | Sheath |
| 6,381,029 | B1 | 4/2002 | Tipirneni |
| 6,381,747 | B1 | 4/2002 | Wonfor et al. |
| 6,385,596 | B1 | 5/2002 | Wiser et al. |
| 6,392,664 | B1 | 5/2002 | White et al. |
| 6,397,387 | B1 | 5/2002 | Rosin et al. |
| 6,401,059 | B1 | 6/2002 | Shen et al. |
| 6,411,307 | B1 | 6/2002 | Rosin et al. |
| 6,424,249 | B1 | 7/2002 | Houvener |
| 6,424,715 | B1 | 7/2002 | Saito |

(56) References Cited

U.S. PATENT DOCUMENTS

| | | |
|---|---|---|
| 6,425,084 B1 | 7/2002 | Rallis et al. |
| 6,434,403 B1 | 8/2002 | Ausems et al. |
| 6,434,535 B1 | 8/2002 | Kupka et al. |
| 6,446,004 B1 | 9/2002 | Cao et al. |
| 6,446,130 B1 | 9/2002 | Grapes |
| 6,456,958 B1 | 9/2002 | Xydis |
| 6,463,534 B1 | 10/2002 | Geiger et al. |
| 6,480,101 B1 | 11/2002 | Kelly et al. |
| 6,480,188 B1 | 11/2002 | Horsley |
| 6,484,182 B1 | 11/2002 | Dunphy et al. |
| 6,484,260 B1 | 11/2002 | Scott et al. |
| 6,484,946 B2 | 11/2002 | Matsumoto et al. |
| 6,487,663 B1 | 11/2002 | Jaisimha et al. |
| 6,490,443 B1 | 12/2002 | Freeny, Jr. |
| 6,510,350 B1 | 1/2003 | Steen et al. |
| 6,522,253 B1 | 2/2003 | Saltus |
| 6,523,113 B1 | 2/2003 | Wehrenberg |
| 6,529,949 B1 | 3/2003 | Getsin et al. |
| 6,546,418 B2 | 4/2003 | Schena et al. |
| 6,550,011 B1 | 4/2003 | Sims, III |
| 6,563,465 B2 | 5/2003 | Frecska |
| 6,563,805 B1 | 5/2003 | Ma et al. |
| 6,564,380 B1 | 5/2003 | Murphy |
| 6,577,238 B1 | 6/2003 | Whitesmith et al. |
| 6,593,887 B2 | 7/2003 | Luk et al. |
| 6,597,680 B1 | 7/2003 | Lindskog et al. |
| 6,607,136 B1 | 8/2003 | Atsmon et al. |
| 6,621,528 B1 | 9/2003 | Kessler et al. |
| 6,624,752 B2 | 9/2003 | Klitsgaard et al. |
| 6,628,302 B2 | 9/2003 | White et al. |
| 6,632,992 B2 | 10/2003 | Hasegawa |
| 6,633,981 B1 | 10/2003 | Davis |
| 6,645,077 B2 | 11/2003 | Rowe |
| 6,647,417 B1 | 11/2003 | Hunter et al. |
| 6,657,538 B1 | 12/2003 | Ritter |
| 6,658,566 B1 | 12/2003 | Hazard |
| 6,667,684 B1 | 12/2003 | Waggamon et al. |
| 6,669,096 B1 | 12/2003 | Saphar et al. |
| 6,671,808 B1 | 12/2003 | Abbott et al. |
| 6,683,954 B1 | 1/2004 | Searle |
| 6,697,944 B1 | 2/2004 | Jones et al. |
| 6,709,333 B1 | 3/2004 | Bradford et al. |
| 6,711,464 B1 | 3/2004 | Yap et al. |
| 6,714,168 B2 | 3/2004 | Berenbaum |
| 6,715,246 B1 | 4/2004 | Frecska et al. |
| 6,728,397 B2 | 4/2004 | McNeal |
| 6,737,955 B2 | 5/2004 | Ghabra et al. |
| 6,758,394 B2 | 7/2004 | Maskatiya et al. |
| 6,771,969 B1 | 8/2004 | Chinoy et al. |
| 6,775,655 B1 | 8/2004 | Peinado et al. |
| 6,785,474 B2 | 8/2004 | Hirt et al. |
| 6,788,640 B2 | 9/2004 | Celeste |
| 6,788,924 B1 | 9/2004 | Knutson et al. |
| 6,795,425 B1 | 9/2004 | Raith |
| 6,804,825 B1 | 10/2004 | White et al. |
| 6,806,887 B2 | 10/2004 | Chernock et al. |
| 6,819,219 B1 | 11/2004 | Bolle et al. |
| 6,839,542 B2 | 1/2005 | Sibecas et al. |
| 6,850,147 B2 | 2/2005 | Prokoski et al. |
| 6,853,988 B1 | 2/2005 | Dickinson et al. |
| 6,859,812 B1 | 2/2005 | Poynor |
| 6,861,980 B1 | 3/2005 | Rowitch et al. |
| 6,873,975 B1 | 3/2005 | Hatakeyama et al. |
| 6,879,567 B2 | 4/2005 | Callaway et al. |
| 6,879,966 B1 | 4/2005 | Lapsley et al. |
| 6,886,741 B1 | 5/2005 | Salveson |
| 6,889,067 B2 | 5/2005 | Willey |
| 6,891,822 B1 | 5/2005 | Gubbi et al. |
| 6,892,307 B1 | 5/2005 | Wood et al. |
| 6,930,643 B2 | 8/2005 | Byrne et al. |
| 6,947,003 B2 | 9/2005 | Huor |
| 6,950,941 B1 | 9/2005 | Lee et al. |
| 6,957,086 B2 | 10/2005 | Bahl et al. |
| 6,961,858 B2 | 11/2005 | Fransdonk |
| 6,963,270 B1 | 11/2005 | Gallagher et al. |
| 6,963,971 B1 | 11/2005 | Bush et al. |
| 6,973,576 B2 | 12/2005 | Giobbi |
| 6,975,202 B1 | 12/2005 | Rodriguez et al. |
| 6,980,087 B2 | 12/2005 | Zukowski |
| 6,983,882 B2 | 1/2006 | Cassone |
| 6,999,032 B2 | 2/2006 | Pakray et al. |
| 7,012,503 B2 | 3/2006 | Nielsen |
| 7,020,635 B2 | 3/2006 | Hamilton et al. |
| 7,031,945 B1 | 4/2006 | Donner |
| 7,049,963 B2 | 5/2006 | Waterhouse et al. |
| 7,055,171 B1 | 5/2006 | Martin et al. |
| 7,058,806 B2 | 6/2006 | Smeets et al. |
| 7,061,380 B1 | 6/2006 | Orlando et al. |
| 7,068,623 B1 | 6/2006 | Barany et al. |
| 7,072,900 B2 | 7/2006 | Sweitzer et al. |
| 7,079,079 B2 | 7/2006 | Jo et al. |
| 7,080,049 B2 | 7/2006 | Truitt et al. |
| 7,082,415 B1 | 7/2006 | Robinson et al. |
| 7,090,126 B2 | 8/2006 | Kelly et al. |
| 7,090,128 B2 | 8/2006 | Farley et al. |
| 7,100,053 B1 | 8/2006 | Brown et al. |
| 7,107,455 B1 | 9/2006 | Merkin |
| 7,107,462 B2 | 9/2006 | Fransdonk |
| 7,111,789 B2 | 9/2006 | Rajasekaran et al. |
| 7,112,138 B2 | 9/2006 | Hedrick et al. |
| 7,119,659 B2 | 10/2006 | Bonalle et al. |
| 7,123,149 B2 | 10/2006 | Nowak et al. |
| 7,130,668 B2 | 10/2006 | Chang et al. |
| 7,131,139 B1 | 10/2006 | Meier |
| 7,137,008 B1 | 11/2006 | Hamid et al. |
| 7,137,012 B1 | 11/2006 | Kamibayashi et al. |
| 7,139,914 B2 | 11/2006 | Arnouse |
| 7,150,045 B2 | 12/2006 | Koelle et al. |
| 7,155,416 B2 | 12/2006 | Shatford |
| 7,159,114 B1 | 1/2007 | Zajkowski et al. |
| 7,159,765 B2 | 1/2007 | Frerking |
| 7,167,987 B2 | 1/2007 | Angelo |
| 7,168,089 B2 | 1/2007 | Nguyen et al. |
| 7,176,797 B2 | 2/2007 | Zai et al. |
| 7,185,363 B1 | 2/2007 | Narin et al. |
| 7,188,110 B1 | 3/2007 | Ludtke et al. |
| 7,191,466 B1 | 3/2007 | Hamid et al. |
| 7,194,438 B2 | 3/2007 | Sovio et al. |
| 7,209,955 B1 | 4/2007 | Major et al. |
| 7,218,944 B2 | 5/2007 | Cromer et al. |
| 7,225,161 B2 | 5/2007 | Lam et al. |
| 7,230,908 B2 | 6/2007 | Vanderaar et al. |
| 7,231,068 B2 | 6/2007 | Tibor |
| 7,231,451 B2 | 6/2007 | Law et al. |
| 7,239,226 B2 | 7/2007 | Berardi et al. |
| 7,242,923 B2 | 7/2007 | Perera et al. |
| 7,249,177 B1 | 7/2007 | Miller |
| 7,272,723 B1 | 9/2007 | Abbott et al. |
| 7,277,737 B1 | 10/2007 | Vollmer et al. |
| 7,278,025 B2 | 10/2007 | Saito et al. |
| 7,283,650 B1 | 10/2007 | Sharma et al. |
| 7,295,119 B2 | 11/2007 | Rappaport et al. |
| 7,305,560 B2 | 12/2007 | Giobbi |
| 7,310,042 B2 | 12/2007 | Seifert |
| 7,314,164 B2 | 1/2008 | Bonalle et al. |
| 7,317,799 B2 | 1/2008 | Hammersmith et al. |
| 7,319,395 B2 | 1/2008 | Puzio et al. |
| 7,330,108 B2 | 2/2008 | Thomas |
| 7,333,002 B2 | 2/2008 | Bixler et al. |
| 7,333,615 B1 | 2/2008 | Jarboe et al. |
| 7,336,181 B2 | 2/2008 | Nowak et al. |
| 7,336,182 B2 | 2/2008 | Baranowski et al. |
| 7,337,326 B2 | 2/2008 | Palmer et al. |
| 7,341,181 B2 | 3/2008 | Bonalle et al. |
| 7,342,503 B1 | 3/2008 | Light et al. |
| 7,349,557 B2 | 3/2008 | Tibor |
| 7,356,393 B1 | 4/2008 | Schlatre et al. |
| 7,356,706 B2 | 4/2008 | Scheurich |
| 7,361,919 B2 | 4/2008 | Setlak |
| 7,363,494 B2 | 4/2008 | Brainard et al. |
| 7,370,366 B2 | 5/2008 | Lacan et al. |
| 7,378,939 B2 | 5/2008 | Sengupta et al. |
| 7,380,202 B1 | 5/2008 | Lindhorst et al. |
| 7,382,799 B1 | 6/2008 | Young et al. |

(56) References Cited

U.S. PATENT DOCUMENTS

| | | | |
|---|---|---|---|
| 7,387,235 | B2 | 6/2008 | Gilbert et al. |
| 7,401,731 | B1 | 7/2008 | Pletz et al. |
| 7,404,088 | B2 | 7/2008 | Giobbi |
| 7,408,799 | B1 | 8/2008 | Kang |
| 7,424,134 | B2 | 9/2008 | Chou |
| 7,437,330 | B1 | 10/2008 | Robinson et al. |
| 7,447,911 | B2 | 11/2008 | Chou et al. |
| 7,448,087 | B2 | 11/2008 | Ohmori et al. |
| 7,458,510 | B1 | 12/2008 | Zhou |
| 7,460,836 | B2 | 12/2008 | Smith et al. |
| 7,461,444 | B2 | 12/2008 | Deaett et al. |
| 7,464,053 | B1 | 12/2008 | Pylant |
| 7,464,059 | B1 | 12/2008 | Robinson et al. |
| 7,466,232 | B2 | 12/2008 | Neuwirth |
| 7,472,280 | B2 | 12/2008 | Giobbi |
| 7,477,285 | B1 * | 1/2009 | Johnson ................ G16H 40/20 725/108 |
| 7,512,806 | B2 | 3/2009 | Lemke |
| 7,525,413 | B2 | 4/2009 | Jung et al. |
| 7,529,944 | B2 | 5/2009 | Hamid |
| 7,533,809 | B1 | 5/2009 | Robinson et al. |
| 7,545,312 | B2 | 6/2009 | Kiang et al. |
| 7,565,329 | B2 | 7/2009 | Lapsley et al. |
| 7,573,382 | B2 | 8/2009 | Choubey et al. |
| 7,573,841 | B2 | 8/2009 | Lee et al. |
| 7,574,734 | B2 | 8/2009 | Fedronic et al. |
| 7,578,442 | B2 | 8/2009 | Knowles et al. |
| 7,583,238 | B2 | 9/2009 | Cassen et al. |
| 7,583,643 | B2 | 9/2009 | Smith et al. |
| 7,587,502 | B2 | 9/2009 | Crawford et al. |
| 7,587,611 | B2 | 9/2009 | Johnson et al. |
| 7,594,611 | B1 | 9/2009 | Arrington, III |
| 7,595,765 | B1 | 9/2009 | Hirsch et al. |
| 7,603,564 | B2 | 10/2009 | Adachi |
| 7,606,733 | B2 | 10/2009 | Shmueli et al. |
| 7,617,523 | B2 | 11/2009 | Das et al. |
| 7,620,184 | B2 | 11/2009 | Marque Pucheu |
| 7,624,073 | B1 | 11/2009 | Robinson et al. |
| 7,624,417 | B2 | 11/2009 | Dua |
| 7,640,273 | B2 | 12/2009 | Wallmeier et al. |
| 7,644,443 | B2 | 1/2010 | Matsuyama et al. |
| 7,646,307 | B2 | 1/2010 | Plocher et al. |
| 7,652,892 | B2 | 1/2010 | Shiu et al. |
| 7,676,380 | B2 | 3/2010 | Graves et al. |
| 7,689,005 | B2 | 3/2010 | Wang et al. |
| 7,701,858 | B2 | 4/2010 | Werb et al. |
| 7,706,896 | B2 | 4/2010 | Music et al. |
| 7,711,152 | B1 | 5/2010 | Davida et al. |
| 7,711,586 | B2 | 5/2010 | Aggarwal et al. |
| 7,715,593 | B1 | 5/2010 | Adams et al. |
| 7,724,713 | B2 | 5/2010 | Del Prado Pavon et al. |
| 7,724,717 | B2 | 5/2010 | Porras et al. |
| 7,724,720 | B2 | 5/2010 | Korpela et al. |
| 7,764,236 | B2 | 7/2010 | Hill et al. |
| 7,765,164 | B1 | 7/2010 | Robinson et al. |
| 7,765,181 | B2 | 7/2010 | Thomas et al. |
| 7,768,960 | B1 | 8/2010 | Barratt |
| 7,773,754 | B2 | 8/2010 | Buer et al. |
| 7,774,613 | B2 | 8/2010 | Lemke |
| 7,780,082 | B2 | 8/2010 | Handa et al. |
| 7,796,551 | B1 | 9/2010 | Machiraju et al. |
| 7,813,822 | B1 | 10/2010 | Hoffberg |
| 7,865,448 | B2 | 1/2011 | Pizarro |
| 7,865,937 | B1 | 1/2011 | White et al. |
| 7,883,003 | B2 | 2/2011 | Giobbi et al. |
| 7,883,417 | B2 | 2/2011 | Bruzzese et al. |
| 7,904,718 | B2 | 3/2011 | Giobbi et al. |
| 7,943,868 | B2 | 5/2011 | Anders et al. |
| 7,957,536 | B2 | 6/2011 | Nolte |
| 7,961,078 | B1 | 6/2011 | Reynolds et al. |
| 7,984,064 | B2 | 7/2011 | Fusari |
| 7,996,514 | B2 | 8/2011 | Baumert et al. |
| 8,026,821 | B2 | 9/2011 | Reeder et al. |
| 8,036,152 | B2 | 10/2011 | Brown et al. |
| 8,049,594 | B1 | 11/2011 | Baranowski |
| 8,077,041 | B2 | 12/2011 | Stern et al. |
| 8,081,215 | B2 | 12/2011 | Kuo et al. |
| 8,082,160 | B2 | 12/2011 | Collins et al. |
| 8,089,354 | B2 | 1/2012 | Perkins |
| 8,112,066 | B2 | 2/2012 | Ben Ayed |
| 8,125,624 | B2 | 2/2012 | Jones et al. |
| 8,135,624 | B1 | 3/2012 | Ramalingam et al. |
| 8,171,528 | B1 | 5/2012 | Brown |
| 8,193,923 | B2 | 6/2012 | Rork et al. |
| 8,200,980 | B1 | 6/2012 | Robinson et al. |
| 8,215,552 | B1 | 7/2012 | Rambadt |
| 8,219,129 | B2 | 7/2012 | Brown et al. |
| 8,248,263 | B2 | 8/2012 | Shervey et al. |
| 8,258,942 | B1 | 9/2012 | Lanzone et al. |
| 8,294,554 | B2 | 10/2012 | Shoarinejad et al. |
| 8,296,573 | B2 | 10/2012 | Bolle et al. |
| 8,307,414 | B2 | 11/2012 | Zerfos et al. |
| 8,325,011 | B2 | 12/2012 | Butler et al. |
| 8,340,672 | B2 | 12/2012 | Brown et al. |
| 8,352,730 | B2 | 1/2013 | Giobbi |
| 8,373,562 | B1 | 2/2013 | Heinze et al. |
| 8,387,124 | B2 | 2/2013 | Smetters et al. |
| 8,390,456 | B2 | 3/2013 | Puleston et al. |
| 8,395,484 | B2 | 3/2013 | Fullerton |
| 8,410,906 | B1 | 4/2013 | Dacus et al. |
| 8,412,949 | B2 | 4/2013 | Giobbi et al. |
| 8,421,606 | B2 | 4/2013 | Collins et al. |
| 8,424,079 | B2 | 4/2013 | Adams et al. |
| 8,432,262 | B2 | 4/2013 | Talty et al. |
| 8,433,919 | B2 | 4/2013 | Giobbi et al. |
| 8,448,858 | B1 | 5/2013 | Kundu et al. |
| 8,457,672 | B2 | 6/2013 | Brown et al. |
| 8,473,748 | B2 | 6/2013 | Sampas |
| 8,484,696 | B2 | 7/2013 | Gatto et al. |
| 8,494,576 | B1 | 7/2013 | Bye et al. |
| 8,508,336 | B2 | 8/2013 | Giobbi et al. |
| 8,511,555 | B2 | 8/2013 | Babcock et al. |
| 8,519,823 | B2 | 8/2013 | Rinkes |
| 8,522,019 | B2 | 8/2013 | Michaelis |
| 8,558,699 | B2 | 10/2013 | Butler et al. |
| 8,572,391 | B2 | 10/2013 | Golan et al. |
| 8,577,091 | B2 | 11/2013 | Ivanov et al. |
| 8,646,042 | B1 | 2/2014 | Brown |
| 8,659,427 | B2 | 2/2014 | Brown et al. |
| 8,678,273 | B2 | 3/2014 | Mcneal |
| 8,717,346 | B2 | 5/2014 | Claessen |
| 8,738,925 | B1 | 5/2014 | Park et al. |
| 8,799,574 | B2 | 8/2014 | Corda |
| 8,838,993 | B2 | 9/2014 | Giobbi et al. |
| 8,856,539 | B2 | 10/2014 | Weiss |
| 8,857,716 | B1 | 10/2014 | Giobbi et al. |
| 8,886,954 | B1 | 11/2014 | Giobbi |
| 8,907,861 | B2 | 12/2014 | Hirt |
| 8,914,477 | B2 | 12/2014 | Gammon |
| 8,918,854 | B1 | 12/2014 | Giobbi |
| 8,931,698 | B2 | 1/2015 | Ishikawa et al. |
| 8,979,646 | B2 | 3/2015 | Moser et al. |
| 9,020,854 | B2 | 4/2015 | Giobbi |
| 9,037,140 | B1 | 5/2015 | Brown |
| 9,042,819 | B2 | 5/2015 | Dua |
| 9,049,188 | B1 | 6/2015 | Brown |
| 9,113,464 | B2 | 8/2015 | Brown et al. |
| 9,165,233 | B2 | 10/2015 | Testanero |
| 9,189,788 | B1 | 11/2015 | Robinson et al. |
| 9,230,399 | B2 | 1/2016 | Yacenda |
| 9,235,700 | B1 | 1/2016 | Brown |
| 9,251,326 | B2 | 2/2016 | Giobbi et al. |
| 9,251,332 | B2 | 2/2016 | Giobbi |
| 9,265,043 | B2 | 2/2016 | Brown et al. |
| 9,265,450 | B1 | 2/2016 | Giobbi |
| 9,269,221 | B2 | 2/2016 | Brown et al. |
| 9,276,914 | B2 | 3/2016 | Woodward et al. |
| 9,298,905 | B1 | 3/2016 | Giobbi |
| 9,305,312 | B2 | 4/2016 | Kountotsis et al. |
| 9,322,974 | B1 | 4/2016 | Giobbi |
| 9,405,898 | B2 | 8/2016 | Giobbi |
| 9,418,205 | B2 | 8/2016 | Giobbi |
| 9,430,624 | B1 | 8/2016 | Mortensen et al. |
| 9,450,956 | B1 | 9/2016 | Giobbi |

(56) References Cited

U.S. PATENT DOCUMENTS

| | | |
|---|---|---|
| 9,542,542 B2 | 1/2017 | Giobbi et al. |
| 9,613,483 B2 | 4/2017 | Giobbi |
| 9,679,289 B1 | 6/2017 | Brown |
| 9,728,080 B1 | 8/2017 | Giobbi et al. |
| 9,807,091 B2 | 10/2017 | Giobbi |
| 9,830,504 B2 | 11/2017 | Masood et al. |
| 9,892,250 B2 | 2/2018 | Giobbi |
| 9,898,662 B2 | 2/2018 | Tsuda et al. |
| 9,904,816 B1 | 2/2018 | Giobbi et al. |
| 9,990,628 B2 | 6/2018 | Giobbi |
| 10,026,253 B2 | 7/2018 | Giobbi |
| 10,073,960 B1 | 9/2018 | Brown |
| 10,110,385 B1 | 10/2018 | Rush et al. |
| 10,171,460 B2 | 1/2019 | Giobbi |
| 10,217,339 B1 | 2/2019 | Giobbi |
| 10,229,294 B1 | 3/2019 | Giobbi et al. |
| 10,313,336 B2 | 6/2019 | Giobbi |
| 10,334,541 B1 | 6/2019 | Brown |
| 10,362,483 B2 | 7/2019 | Frusina |
| 10,374,795 B1 | 8/2019 | Giobbi et al. |
| 10,383,112 B2 | 8/2019 | Brown et al. |
| 10,403,128 B2 | 9/2019 | Giobbi et al. |
| 10,437,976 B2 | 10/2019 | Giobbi |
| 10,455,533 B2 | 10/2019 | Brown |
| 10,469,456 B1 | 11/2019 | Giobbi |
| 10,567,965 B2 | 2/2020 | Boettcher et al. |
| 10,698,989 B2 | 6/2020 | Giobbi |
| 10,764,044 B1 | 9/2020 | Giobbi et al. |
| 10,769,939 B2 | 9/2020 | Brown et al. |
| 10,817,964 B2 | 10/2020 | Guillama et al. |
| 10,909,229 B2 | 2/2021 | Giobbi |
| 10,943,471 B1 | 3/2021 | Giobbi et al. |
| 11,086,979 B1 | 8/2021 | Giobbi |
| 11,212,797 B2 | 12/2021 | Brown et al. |
| 11,219,022 B2 | 1/2022 | Brown et al. |
| 11,562,644 B2 | 1/2023 | Brown et al. |
| 2001/0000535 A1 | 4/2001 | Lapsley et al. |
| 2001/0021950 A1 | 9/2001 | Hawley et al. |
| 2001/0024428 A1 | 9/2001 | Onouchi |
| 2001/0026619 A1 | 10/2001 | Howard et al. |
| 2001/0027121 A1 | 10/2001 | Boesen |
| 2001/0027439 A1 | 10/2001 | Holtzman et al. |
| 2001/0044337 A1 | 11/2001 | Rowe et al. |
| 2002/0004783 A1 | 1/2002 | Paltenghe et al. |
| 2002/0007456 A1 | 1/2002 | Peinado et al. |
| 2002/0010679 A1 | 1/2002 | Felsher |
| 2002/0013772 A1 | 1/2002 | Peinado |
| 2002/0014954 A1 | 2/2002 | Fitzgibbon et al. |
| 2002/0015008 A1 | 2/2002 | Kishida et al. |
| 2002/0015494 A1 | 2/2002 | Nagai et al. |
| 2002/0019811 A1 | 2/2002 | Lapsley et al. |
| 2002/0022455 A1 | 2/2002 | Salokannel et al. |
| 2002/0023032 A1 | 2/2002 | Pearson et al. |
| 2002/0023217 A1 | 2/2002 | Wheeler et al. |
| 2002/0026424 A1 | 2/2002 | Akashi |
| 2002/0037732 A1 | 3/2002 | Gous et al. |
| 2002/0052193 A1 | 5/2002 | Chetty |
| 2002/0055908 A1 | 5/2002 | Di Giorgio et al. |
| 2002/0056043 A1 | 5/2002 | Glass |
| 2002/0059114 A1 | 5/2002 | Cockrill et al. |
| 2002/0062249 A1 | 5/2002 | Iannacci |
| 2002/0068605 A1 | 6/2002 | Stanley |
| 2002/0069364 A1 | 6/2002 | Dosch |
| 2002/0071559 A1 | 6/2002 | Christensen et al. |
| 2002/0073042 A1 | 6/2002 | Maritzen et al. |
| 2002/0076051 A1 | 6/2002 | Nii |
| 2002/0080969 A1 | 6/2002 | Giobbi |
| 2002/0083178 A1 | 6/2002 | Brothers |
| 2002/0083318 A1 | 6/2002 | Larose |
| 2002/0086690 A1 | 7/2002 | Takahashi et al. |
| 2002/0089890 A1 | 7/2002 | Fibranz et al. |
| 2002/0091646 A1 | 7/2002 | Lake et al. |
| 2002/0095586 A1 | 7/2002 | Doyle et al. |
| 2002/0095587 A1 | 7/2002 | Doyle et al. |
| 2002/0097876 A1 | 7/2002 | Harrison |
| 2002/0098888 A1 | 7/2002 | Rowe et al. |
| 2002/0100798 A1 | 8/2002 | Farrugia et al. |
| 2002/0103027 A1 | 8/2002 | Rowe et al. |
| 2002/0103881 A1 | 8/2002 | Granade et al. |
| 2002/0104006 A1 | 8/2002 | Boate et al. |
| 2002/0104019 A1 | 8/2002 | Chatani et al. |
| 2002/0105918 A1 | 8/2002 | Yamada et al. |
| 2002/0108049 A1 | 8/2002 | Xu et al. |
| 2002/0109580 A1 | 8/2002 | Shreve et al. |
| 2002/0111919 A1 | 8/2002 | Weller et al. |
| 2002/0112183 A1 | 8/2002 | Baird et al. |
| 2002/0116615 A1 | 8/2002 | Nguyen et al. |
| 2002/0124251 A1 | 9/2002 | Hunter et al. |
| 2002/0128017 A1 | 9/2002 | Virtanen |
| 2002/0128057 A1 | 9/2002 | Walker et al. |
| 2002/0129262 A1 | 9/2002 | Kutaragi et al. |
| 2002/0138438 A1 | 9/2002 | Bardwell |
| 2002/0138767 A1 | 9/2002 | Hamid et al. |
| 2002/0140542 A1 | 10/2002 | Prokoski et al. |
| 2002/0141586 A1 | 10/2002 | Margalit et al. |
| 2002/0143623 A1 | 10/2002 | Dayley |
| 2002/0143655 A1 | 10/2002 | Elston et al. |
| 2002/0144116 A1 | 10/2002 | Giobbi |
| 2002/0144117 A1 | 10/2002 | Faigle |
| 2002/0147653 A1 | 10/2002 | Shmueli et al. |
| 2002/0148892 A1 | 10/2002 | Bardwell |
| 2002/0150282 A1 | 10/2002 | Kinsella |
| 2002/0152391 A1 | 10/2002 | Willins et al. |
| 2002/0153996 A1 | 10/2002 | Chan et al. |
| 2002/0158121 A1 | 10/2002 | Stanford-Clark |
| 2002/0158750 A1 | 10/2002 | Almalik |
| 2002/0158765 A1 | 10/2002 | Pape et al. |
| 2002/0160820 A1 | 10/2002 | Winkler |
| 2002/0174348 A1 | 11/2002 | Ting |
| 2002/0177460 A1 | 11/2002 | Beasley et al. |
| 2002/0178063 A1 | 11/2002 | Gravelle et al. |
| 2002/0184208 A1 | 12/2002 | Kato |
| 2002/0187746 A1 | 12/2002 | Cheng et al. |
| 2002/0191816 A1 | 12/2002 | Maritzen et al. |
| 2002/0196963 A1 | 12/2002 | Bardwell |
| 2002/0199120 A1 | 12/2002 | Schmidt |
| 2003/0001016 A1 | 1/2003 | Fraier et al. |
| 2003/0022701 A1 | 1/2003 | Gupta |
| 2003/0024975 A1 | 2/2003 | Rajasekharan |
| 2003/0034877 A1 | 2/2003 | Miller et al. |
| 2003/0036416 A1 | 2/2003 | Pattabiraman et al. |
| 2003/0036425 A1 | 2/2003 | Kaminkow et al. |
| 2003/0046228 A1 | 3/2003 | Berney |
| 2003/0046237 A1 | 3/2003 | Uberti |
| 2003/0046552 A1 | 3/2003 | Hamid |
| 2003/0048174 A1 | 3/2003 | Stevens et al. |
| 2003/0051173 A1 | 3/2003 | Krueger |
| 2003/0054868 A1 | 3/2003 | Paulsen et al. |
| 2003/0054881 A1 | 3/2003 | Hedrick et al. |
| 2003/0055689 A1 | 3/2003 | Block et al. |
| 2003/0055792 A1 | 3/2003 | Kinoshita et al. |
| 2003/0061172 A1 | 3/2003 | Robinson |
| 2003/0063619 A1 | 4/2003 | Montano et al. |
| 2003/0079133 A1 | 4/2003 | Breiter et al. |
| 2003/0087601 A1 | 5/2003 | Agam et al. |
| 2003/0088441 A1 | 5/2003 | McNerney |
| 2003/0105719 A1 | 6/2003 | Berger et al. |
| 2003/0109274 A1 | 6/2003 | Budka et al. |
| 2003/0115351 A1 | 6/2003 | Giobbi |
| 2003/0115474 A1 | 6/2003 | Khan et al. |
| 2003/0117969 A1 | 6/2003 | Koo et al. |
| 2003/0117980 A1 | 6/2003 | Kim et al. |
| 2003/0120934 A1 | 6/2003 | Ortiz |
| 2003/0127511 A1 | 7/2003 | Kelly et al. |
| 2003/0128866 A1 | 7/2003 | Mcneal |
| 2003/0137404 A1 | 7/2003 | Bonneau et al. |
| 2003/0139190 A1 | 7/2003 | Steelberg et al. |
| 2003/0142041 A1 | 7/2003 | Barlow et al. |
| 2003/0146835 A1 | 8/2003 | Carter |
| 2003/0149744 A1 | 8/2003 | Bierre et al. |
| 2003/0156742 A1 | 8/2003 | Witt et al. |
| 2003/0159040 A1 | 8/2003 | Hashimoto et al. |
| 2003/0163388 A1 | 8/2003 | Beane |
| 2003/0167207 A1 | 9/2003 | Berardi et al. |

(56) References Cited

U.S. PATENT DOCUMENTS

| | | |
|---|---|---|
| 2003/0169697 A1 | 9/2003 | Suzuki et al. |
| 2003/0172028 A1 | 9/2003 | Abell et al. |
| 2003/0172037 A1 | 9/2003 | Jung et al. |
| 2003/0174839 A1 | 9/2003 | Yamagata et al. |
| 2003/0176218 A1 | 9/2003 | Lemay et al. |
| 2003/0177102 A1 | 9/2003 | Robinson |
| 2003/0186739 A1 | 10/2003 | Paulsen et al. |
| 2003/0195842 A1 | 10/2003 | Reece |
| 2003/0196084 A1 | 10/2003 | Okereke et al. |
| 2003/0199267 A1 | 10/2003 | Iwasa et al. |
| 2003/0204526 A1 | 10/2003 | Salehi-Had |
| 2003/0204721 A1 | 10/2003 | Barrus et al. |
| 2003/0213840 A1 | 11/2003 | Livingston et al. |
| 2003/0223394 A1 | 12/2003 | Parantainen et al. |
| 2003/0225703 A1 | 12/2003 | Angel |
| 2003/0226031 A1 | 12/2003 | Proudler et al. |
| 2003/0233458 A1 | 12/2003 | Kwon et al. |
| 2004/0002347 A1 | 1/2004 | Hoctor et al. |
| 2004/0015403 A1 | 1/2004 | Moskowitz et al. |
| 2004/0021552 A1 | 2/2004 | Koo |
| 2004/0022384 A1 | 2/2004 | Flores et al. |
| 2004/0029620 A1 | 2/2004 | Karaoguz |
| 2004/0029635 A1 | 2/2004 | Giobbi |
| 2004/0030764 A1 | 2/2004 | Birk et al. |
| 2004/0030894 A1 | 2/2004 | Labrou et al. |
| 2004/0035644 A1 | 2/2004 | Ford et al. |
| 2004/0039909 A1 | 2/2004 | Cheng |
| 2004/0044627 A1 | 3/2004 | Russell et al. |
| 2004/0048570 A1 | 3/2004 | Oba et al. |
| 2004/0048609 A1 | 3/2004 | Kosaka |
| 2004/0059682 A1 | 3/2004 | Hasumi et al. |
| 2004/0059912 A1 | 3/2004 | Zizzi |
| 2004/0064728 A1 | 4/2004 | Scheurich |
| 2004/0068656 A1 | 4/2004 | Lu |
| 2004/0073792 A1 | 4/2004 | Noble et al. |
| 2004/0081127 A1 | 4/2004 | Gardner et al. |
| 2004/0082385 A1 | 4/2004 | Silva et al. |
| 2004/0088558 A1 | 5/2004 | Candelore |
| 2004/0090345 A1 | 5/2004 | Hitt |
| 2004/0098597 A1 | 5/2004 | Giobbi |
| 2004/0103064 A1 | 5/2004 | Howard et al. |
| 2004/0114563 A1 | 6/2004 | Shvodian |
| 2004/0117644 A1 | 6/2004 | Colvin |
| 2004/0123106 A1 | 6/2004 | D'Angelo et al. |
| 2004/0123127 A1 | 6/2004 | Teicher et al. |
| 2004/0127277 A1 | 7/2004 | Walker et al. |
| 2004/0128162 A1 | 7/2004 | Schlotterbeck et al. |
| 2004/0128389 A1 | 7/2004 | Kopchik |
| 2004/0128500 A1 | 7/2004 | Cihula et al. |
| 2004/0128508 A1 | 7/2004 | Wheeler et al. |
| 2004/0128519 A1 | 7/2004 | Klinger et al. |
| 2004/0129787 A1 | 7/2004 | Saito et al. |
| 2004/0132432 A1 | 7/2004 | Moores et al. |
| 2004/0137912 A1 | 7/2004 | Lin |
| 2004/0153649 A1 | 8/2004 | Rhoads et al. |
| 2004/0158746 A1 | 8/2004 | Hu et al. |
| 2004/0166875 A1 | 8/2004 | Jenkins et al. |
| 2004/0167465 A1 | 8/2004 | Mihai et al. |
| 2004/0181695 A1 | 9/2004 | Walker |
| 2004/0193925 A1 | 9/2004 | Safriel |
| 2004/0194133 A1 | 9/2004 | Ikeda et al. |
| 2004/0201755 A1 | 10/2004 | Norskog |
| 2004/0203566 A1 | 10/2004 | Leung |
| 2004/0203923 A1 | 10/2004 | Mullen |
| 2004/0208139 A1 | 10/2004 | Iwamura |
| 2004/0209690 A1 | 10/2004 | Bruzzese et al. |
| 2004/0209692 A1 | 10/2004 | Schober et al. |
| 2004/0214582 A1 | 10/2004 | Lan et al. |
| 2004/0215615 A1 | 10/2004 | Larsson et al. |
| 2004/0217859 A1 | 11/2004 | Pucci et al. |
| 2004/0218581 A1 | 11/2004 | Cattaneo |
| 2004/0222877 A1 | 11/2004 | Teramura et al. |
| 2004/0230488 A1 | 11/2004 | Beenau et al. |
| 2004/0230809 A1 | 11/2004 | Lowensohn et al. |
| 2004/0234117 A1 | 11/2004 | Tibor |
| 2004/0243519 A1 | 12/2004 | Perttila et al. |
| 2004/0246103 A1 | 12/2004 | Zukowski |
| 2004/0246950 A1 | 12/2004 | Parker et al. |
| 2004/0250074 A1 | 12/2004 | Kilian-Kehr |
| 2004/0252012 A1 | 12/2004 | Beenau et al. |
| 2004/0252659 A1 | 12/2004 | Yun et al. |
| 2004/0253996 A1 | 12/2004 | Chen et al. |
| 2004/0254837 A1 | 12/2004 | Roshkoff |
| 2004/0255139 A1 | 12/2004 | Giobbi |
| 2004/0255145 A1 | 12/2004 | Chow |
| 2005/0001028 A1 | 1/2005 | Zuili |
| 2005/0002028 A1 | 1/2005 | Kasapi et al. |
| 2005/0005136 A1 | 1/2005 | Chen et al. |
| 2005/0006452 A1 | 1/2005 | Aupperle et al. |
| 2005/0009517 A1 | 1/2005 | Maes |
| 2005/0020322 A1 | 1/2005 | Ruuska et al. |
| 2005/0021369 A1* | 1/2005 | Cohen .................... G16H 40/20 455/73 |
| 2005/0021561 A1 | 1/2005 | Noonan |
| 2005/0025093 A1 | 2/2005 | Yun et al. |
| 2005/0028168 A1 | 2/2005 | Marcjan |
| 2005/0035897 A1 | 2/2005 | Perl et al. |
| 2005/0039027 A1 | 2/2005 | Shapiro |
| 2005/0040961 A1 | 2/2005 | Tuttle |
| 2005/0044372 A1 | 2/2005 | Aull et al. |
| 2005/0044387 A1 | 2/2005 | Ozolins |
| 2005/0047386 A1 | 3/2005 | Yi |
| 2005/0049013 A1 | 3/2005 | Chang et al. |
| 2005/0050208 A1 | 3/2005 | Chatani |
| 2005/0050324 A1 | 3/2005 | Corbett et al. |
| 2005/0054431 A1 | 3/2005 | Walker et al. |
| 2005/0055242 A1 | 3/2005 | Bello et al. |
| 2005/0055244 A1 | 3/2005 | Mullan et al. |
| 2005/0058292 A1 | 3/2005 | Diorio et al. |
| 2005/0074126 A1 | 4/2005 | Stanko |
| 2005/0076242 A1 | 4/2005 | Breuer |
| 2005/0081040 A1 | 4/2005 | Johnson et al. |
| 2005/0084137 A1 | 4/2005 | Kim et al. |
| 2005/0086115 A1 | 4/2005 | Pearson |
| 2005/0086501 A1 | 4/2005 | Woo et al. |
| 2005/0086515 A1 | 4/2005 | Paris |
| 2005/0089000 A1 | 4/2005 | Bae et al. |
| 2005/0090200 A1 | 4/2005 | Karaoguz et al. |
| 2005/0091338 A1 | 4/2005 | De La Huerga |
| 2005/0091553 A1 | 4/2005 | Chien et al. |
| 2005/0094657 A1 | 5/2005 | Sung et al. |
| 2005/0096053 A1 | 5/2005 | Liu et al. |
| 2005/0097037 A1 | 5/2005 | Tibor |
| 2005/0105600 A1 | 5/2005 | Culum et al. |
| 2005/0105734 A1 | 5/2005 | Buer et al. |
| 2005/0108164 A1 | 5/2005 | Salafi et al. |
| 2005/0109836 A1 | 5/2005 | Ben-Aissa |
| 2005/0109841 A1 | 5/2005 | Ryan et al. |
| 2005/0113070 A1 | 5/2005 | Okabe |
| 2005/0114149 A1 | 5/2005 | Rodriguez et al. |
| 2005/0114150 A1 | 5/2005 | Franklin |
| 2005/0116020 A1 | 6/2005 | Smolucha et al. |
| 2005/0117530 A1 | 6/2005 | Abraham et al. |
| 2005/0119979 A1 | 6/2005 | Murashita et al. |
| 2005/0124294 A1 | 6/2005 | Wentink |
| 2005/0125258 A1 | 6/2005 | Yellin et al. |
| 2005/0136947 A1* | 6/2005 | Llombart-Juan ...... G01C 21/20 455/414.1 |
| 2005/0137827 A1 | 6/2005 | Takamiya |
| 2005/0137977 A1 | 6/2005 | Wankmueller |
| 2005/0138390 A1 | 6/2005 | Adams et al. |
| 2005/0138576 A1 | 6/2005 | Baumert et al. |
| 2005/0139656 A1 | 6/2005 | Arnouse |
| 2005/0141451 A1 | 6/2005 | Yoon et al. |
| 2005/0152394 A1 | 7/2005 | Cho |
| 2005/0154897 A1 | 7/2005 | Holloway et al. |
| 2005/0161503 A1 | 7/2005 | Remery et al. |
| 2005/0165684 A1 | 7/2005 | Jensen et al. |
| 2005/0166063 A1 | 7/2005 | Huang |
| 2005/0167482 A1 | 8/2005 | Ramachandran et al. |
| 2005/0169292 A1 | 8/2005 | Young |
| 2005/0177716 A1 | 8/2005 | Ginter et al. |
| 2005/0180385 A1 | 8/2005 | Jeong et al. |
| 2005/0182661 A1 | 8/2005 | Allard et al. |

(56) References Cited

U.S. PATENT DOCUMENTS

| | | |
|---|---|---|
| 2005/0182975 A1 | 8/2005 | Guo et al. |
| 2005/0187792 A1 | 8/2005 | Harper |
| 2005/0192748 A1 | 9/2005 | Andric et al. |
| 2005/0195975 A1 | 9/2005 | Kawakita |
| 2005/0198208 A1 | 9/2005 | Nystrom |
| 2005/0200453 A1 | 9/2005 | Turner et al. |
| 2005/0201389 A1 | 9/2005 | Shimanuki et al. |
| 2005/0203682 A1 | 9/2005 | Omino et al. |
| 2005/0203844 A1 | 9/2005 | Ferguson et al. |
| 2005/0210270 A1 | 9/2005 | Rohatgi et al. |
| 2005/0212657 A1 | 9/2005 | Simon |
| 2005/0215233 A1 | 9/2005 | Perera et al. |
| 2005/0216313 A1 | 9/2005 | Claud et al. |
| 2005/0216639 A1 | 9/2005 | Sparer et al. |
| 2005/0218215 A1 | 10/2005 | Lauden |
| 2005/0220046 A1 | 10/2005 | Falck et al. |
| 2005/0221869 A1 | 10/2005 | Liu et al. |
| 2005/0229007 A1 | 10/2005 | Bolle et al. |
| 2005/0229240 A1 | 10/2005 | Nanba |
| 2005/0231328 A1 | 10/2005 | Castle et al. |
| 2005/0235364 A1 | 10/2005 | Wilson |
| 2005/0242921 A1 | 11/2005 | Zimmerman et al. |
| 2005/0243787 A1 | 11/2005 | Hong et al. |
| 2005/0249385 A1 | 11/2005 | Kondo et al. |
| 2005/0251688 A1 | 11/2005 | Nanavati et al. |
| 2005/0253683 A1 | 11/2005 | Lowe |
| 2005/0256878 A1 | 11/2005 | Brown et al. |
| 2005/0257102 A1 | 11/2005 | Moyer et al. |
| 2005/0264416 A1 | 12/2005 | Maurer |
| 2005/0268111 A1 | 12/2005 | Markham |
| 2005/0269401 A1 | 12/2005 | Spitzer et al. |
| 2005/0272403 A1 | 12/2005 | Ryu et al. |
| 2005/0277385 A1 | 12/2005 | Daum |
| 2005/0281215 A1 | 12/2005 | Budampati et al. |
| 2005/0281320 A1 | 12/2005 | Neugebauer |
| 2005/0282558 A1 | 12/2005 | Choi et al. |
| 2005/0284932 A1 | 12/2005 | Sukeda |
| 2005/0287985 A1 | 12/2005 | Balfanz et al. |
| 2005/0288015 A1 | 12/2005 | Azizi et al. |
| 2005/0288069 A1 | 12/2005 | Arunan et al. |
| 2005/0289473 A1 | 12/2005 | Gustafson et al. |
| 2006/0001525 A1 | 1/2006 | Nitzan et al. |
| 2006/0009216 A1 | 1/2006 | Welnick et al. |
| 2006/0014430 A1 | 1/2006 | Liang et al. |
| 2006/0022042 A1 | 2/2006 | Smets et al. |
| 2006/0022046 A1 | 2/2006 | Iwamura |
| 2006/0022800 A1 | 2/2006 | Krishna et al. |
| 2006/0025180 A1 | 2/2006 | Rajkotia et al. |
| 2006/0026673 A1 | 2/2006 | Tsuchida |
| 2006/0030279 A1 | 2/2006 | Leabman |
| 2006/0030353 A1 | 2/2006 | Jun |
| 2006/0034250 A1 | 2/2006 | Kim et al. |
| 2006/0041746 A1 | 2/2006 | Kirkup et al. |
| 2006/0046664 A1 | 3/2006 | Paradiso et al. |
| 2006/0058102 A1 | 3/2006 | Nguyen et al. |
| 2006/0063575 A1 | 3/2006 | Gatto et al. |
| 2006/0064605 A1 | 3/2006 | Giobbi |
| 2006/0066441 A1 | 3/2006 | Knadle et al. |
| 2006/0069814 A1 | 3/2006 | Abraham et al. |
| 2006/0072586 A1 | 4/2006 | Callaway et al. |
| 2006/0074713 A1 | 4/2006 | Conry et al. |
| 2006/0076401 A1 | 4/2006 | Frerking |
| 2006/0078176 A1 | 4/2006 | Abiko et al. |
| 2006/0087407 A1 | 4/2006 | Stewart et al. |
| 2006/0089138 A1 | 4/2006 | Smith et al. |
| 2006/0097949 A1 | 5/2006 | Luebke et al. |
| 2006/0110012 A1 | 5/2006 | Ritter |
| 2006/0111955 A1 | 5/2006 | Winter et al. |
| 2006/0113381 A1 | 6/2006 | Hochstein et al. |
| 2006/0116935 A1 | 6/2006 | Evans |
| 2006/0117013 A1 | 6/2006 | Wada |
| 2006/0120287 A1 | 6/2006 | Foti et al. |
| 2006/0129838 A1 | 6/2006 | Chen et al. |
| 2006/0136728 A1 | 6/2006 | Gentry et al. |
| 2006/0136742 A1 | 6/2006 | Giobbi |
| 2006/0143441 A1 | 6/2006 | Giobbi |
| 2006/0144943 A1 | 7/2006 | Kim |
| 2006/0156027 A1 | 7/2006 | Blake |
| 2006/0158308 A1 | 7/2006 | Mcmullen et al. |
| 2006/0163349 A1 | 7/2006 | Neugebauer |
| 2006/0163350 A1 | 7/2006 | Melton et al. |
| 2006/0165060 A1 | 7/2006 | Dua |
| 2006/0169771 A1 | 8/2006 | Brookner |
| 2006/0170530 A1 | 8/2006 | Nwosu et al. |
| 2006/0170565 A1 | 8/2006 | Husak et al. |
| 2006/0172700 A1 | 8/2006 | Wu |
| 2006/0173846 A1 | 8/2006 | Omae et al. |
| 2006/0173991 A1 | 8/2006 | Piikivi |
| 2006/0183426 A1 | 8/2006 | Graves et al. |
| 2006/0183462 A1 | 8/2006 | Kolehmainen |
| 2006/0184531 A1 | 8/2006 | Russlies |
| 2006/0184795 A1 | 8/2006 | Doradla et al. |
| 2006/0185005 A1 | 8/2006 | Graves et al. |
| 2006/0187029 A1 | 8/2006 | Thomas |
| 2006/0190348 A1 | 8/2006 | Ofer et al. |
| 2006/0190413 A1 | 8/2006 | Harper |
| 2006/0194598 A1 | 8/2006 | Kim et al. |
| 2006/0195576 A1 | 8/2006 | Rinne et al. |
| 2006/0198337 A1 | 9/2006 | Hoang et al. |
| 2006/0200467 A1 | 9/2006 | Ohmori et al. |
| 2006/0205408 A1 | 9/2006 | Nakagawa et al. |
| 2006/0208066 A1 | 9/2006 | Finn et al. |
| 2006/0208853 A1 | 9/2006 | Kung et al. |
| 2006/0222042 A1 | 10/2006 | Teramura et al. |
| 2006/0226950 A1 | 10/2006 | Kanou et al. |
| 2006/0229909 A1 | 10/2006 | Kaila et al. |
| 2006/0236373 A1 | 10/2006 | Graves et al. |
| 2006/0237528 A1 | 10/2006 | Bishop et al. |
| 2006/0238305 A1 | 10/2006 | Loving et al. |
| 2006/0268891 A1 | 11/2006 | Heidari-Bateni et al. |
| 2006/0273176 A1 | 12/2006 | Audebert et al. |
| 2006/0274711 A1 | 12/2006 | Nelson et al. |
| 2006/0279412 A1 | 12/2006 | Holland et al. |
| 2006/0286969 A1 | 12/2006 | Talmor et al. |
| 2006/0288095 A1 | 12/2006 | Torok et al. |
| 2006/0288233 A1 | 12/2006 | Kozlay |
| 2006/0290473 A1 | 12/2006 | Mahasenan et al. |
| 2006/0290580 A1 | 12/2006 | Noro et al. |
| 2006/0292986 A1 | 12/2006 | Bitran et al. |
| 2006/0293925 A1 | 12/2006 | Flom |
| 2006/0294388 A1 | 12/2006 | Abraham et al. |
| 2007/0003111 A1 | 1/2007 | Awatsu et al. |
| 2007/0005403 A1 | 1/2007 | Kennedy et al. |
| 2007/0007331 A1 | 1/2007 | Jasper et al. |
| 2007/0008070 A1 | 1/2007 | Friedrich |
| 2007/0008916 A1 | 1/2007 | Haugli et al. |
| 2007/0011724 A1 | 1/2007 | Gonzalez et al. |
| 2007/0016800 A1 | 1/2007 | Spottswood et al. |
| 2007/0019845 A1 | 1/2007 | Kato |
| 2007/0029381 A1 | 2/2007 | Braiman |
| 2007/0032225 A1 | 2/2007 | Konicek et al. |
| 2007/0032288 A1 | 2/2007 | Nelson et al. |
| 2007/0033072 A1 | 2/2007 | Bildirici |
| 2007/0033150 A1 | 2/2007 | Nwosu |
| 2007/0036396 A1 | 2/2007 | Sugita et al. |
| 2007/0038751 A1 | 2/2007 | Jorgensen |
| 2007/0043594 A1 | 2/2007 | Lavergne |
| 2007/0050259 A1 | 3/2007 | Wesley |
| 2007/0050398 A1 | 3/2007 | Mochizuki |
| 2007/0050845 A1 | 3/2007 | Das et al. |
| 2007/0051794 A1 | 3/2007 | Glanz et al. |
| 2007/0051798 A1 | 3/2007 | Kawai et al. |
| 2007/0055630 A1 | 3/2007 | Gauthier et al. |
| 2007/0060095 A1 | 3/2007 | Subrahmanya et al. |
| 2007/0060319 A1 | 3/2007 | Block et al. |
| 2007/0064742 A1 | 3/2007 | Shvodian |
| 2007/0069852 A1 | 3/2007 | Mo et al. |
| 2007/0070040 A1 | 3/2007 | Chen et al. |
| 2007/0072636 A1 | 3/2007 | Worfolk et al. |
| 2007/0073553 A1 | 3/2007 | Flinn et al. |
| 2007/0084523 A1 | 4/2007 | Mclean et al. |
| 2007/0084913 A1 | 4/2007 | Weston |
| 2007/0087682 A1 | 4/2007 | DaCosta |
| 2007/0087834 A1 | 4/2007 | Moser et al. |

(56) References Cited

U.S. PATENT DOCUMENTS

| | | |
|---|---|---|
| 2007/0100507 A1 | 5/2007 | Simon |
| 2007/0100939 A1 | 5/2007 | Bagley et al. |
| 2007/0109117 A1 | 5/2007 | Heitzmann et al. |
| 2007/0112676 A1 | 5/2007 | Kontio et al. |
| 2007/0118891 A1 | 5/2007 | Buer |
| 2007/0120643 A1 | 5/2007 | Lee |
| 2007/0120651 A1 | 5/2007 | Kobayashi et al. |
| 2007/0132586 A1 | 6/2007 | Plocher et al. |
| 2007/0133478 A1 | 6/2007 | Armbruster et al. |
| 2007/0136407 A1 | 6/2007 | Rudelic |
| 2007/0142032 A1 | 6/2007 | Balsillie |
| 2007/0143626 A1 | 6/2007 | Okuda |
| 2007/0147332 A1 | 6/2007 | Lappetelainen et al. |
| 2007/0152826 A1 | 7/2007 | August et al. |
| 2007/0156850 A1 | 7/2007 | Corrion |
| 2007/0157249 A1 | 7/2007 | Cordray et al. |
| 2007/0158411 A1 | 7/2007 | Krieg, Jr. |
| 2007/0159301 A1 | 7/2007 | Hirt et al. |
| 2007/0159994 A1 | 7/2007 | Brown et al. |
| 2007/0164847 A1 | 7/2007 | Crawford et al. |
| 2007/0169121 A1 | 7/2007 | Hunt et al. |
| 2007/0174809 A1 | 7/2007 | Brown et al. |
| 2007/0176756 A1 | 8/2007 | Friedrich |
| 2007/0176778 A1 | 8/2007 | Ando et al. |
| 2007/0180047 A1 | 8/2007 | Dong et al. |
| 2007/0187266 A1 | 8/2007 | Porter et al. |
| 2007/0192601 A1 | 8/2007 | Spain et al. |
| 2007/0194882 A1 | 8/2007 | Yokota et al. |
| 2007/0197261 A1 | 8/2007 | Humbel |
| 2007/0198436 A1 | 8/2007 | Weiss |
| 2007/0204078 A1 | 8/2007 | Boccon-Gibod et al. |
| 2007/0205860 A1 | 9/2007 | Jones et al. |
| 2007/0205861 A1 | 9/2007 | Nair et al. |
| 2007/0207750 A1 | 9/2007 | Brown et al. |
| 2007/0213048 A1 | 9/2007 | Trauberg |
| 2007/0214492 A1 | 9/2007 | Gopi et al. |
| 2007/0218921 A1 | 9/2007 | Lee et al. |
| 2007/0219926 A1 | 9/2007 | Korn |
| 2007/0220272 A1 | 9/2007 | Campisi et al. |
| 2007/0229268 A1 | 10/2007 | Swan et al. |
| 2007/0245157 A1 | 10/2007 | Giobbi et al. |
| 2007/0245158 A1 | 10/2007 | Giobbi et al. |
| 2007/0247366 A1 | 10/2007 | Smith et al. |
| 2007/0258626 A1 | 11/2007 | Reiner |
| 2007/0260883 A1 | 11/2007 | Giobbi et al. |
| 2007/0260888 A1 | 11/2007 | Giobbi et al. |
| 2007/0266257 A1 | 11/2007 | Camaisa et al. |
| 2007/0268862 A1 | 11/2007 | Singh et al. |
| 2007/0271194 A1 | 11/2007 | Walker et al. |
| 2007/0271433 A1 | 11/2007 | Takemura |
| 2007/0277044 A1 | 11/2007 | Graf et al. |
| 2007/0280509 A1 | 12/2007 | Owen et al. |
| 2007/0285212 A1 | 12/2007 | Rotzoll |
| 2007/0285238 A1 | 12/2007 | Batra |
| 2007/0288263 A1 | 12/2007 | Rodgers |
| 2007/0288752 A1 | 12/2007 | Chan |
| 2007/0293155 A1 | 12/2007 | Liao et al. |
| 2007/0294755 A1 | 12/2007 | Dadhia et al. |
| 2007/0296544 A1 | 12/2007 | Beenau et al. |
| 2008/0001783 A1 | 1/2008 | Cargonja et al. |
| 2008/0005432 A1 | 1/2008 | Kagawa |
| 2008/0008359 A1 | 1/2008 | Beenau et al. |
| 2008/0011842 A1 | 1/2008 | Curry et al. |
| 2008/0012685 A1 | 1/2008 | Friedrich et al. |
| 2008/0012767 A1 | 1/2008 | Caliri et al. |
| 2008/0016004 A1 | 1/2008 | Kurasaki et al. |
| 2008/0019578 A1 | 1/2008 | Saito et al. |
| 2008/0028227 A1 | 1/2008 | Sakurai |
| 2008/0028453 A1 | 1/2008 | Nguyen et al. |
| 2008/0040609 A1 | 2/2008 | Giobbi |
| 2008/0046366 A1 | 2/2008 | Bemmel et al. |
| 2008/0046715 A1 | 2/2008 | Balazs et al. |
| 2008/0049700 A1 | 2/2008 | Shah et al. |
| 2008/0061941 A1 | 3/2008 | Fischer et al. |
| 2008/0071577 A1 | 3/2008 | Highley |
| 2008/0072063 A1 | 3/2008 | Takahashi et al. |
| 2008/0088475 A1 | 4/2008 | Martin |
| 2008/0090548 A1 | 4/2008 | Ramalingam |
| 2008/0095359 A1 | 4/2008 | Schreyer et al. |
| 2008/0107089 A1 | 5/2008 | Larsson et al. |
| 2008/0109895 A1 | 5/2008 | Janevski |
| 2008/0111752 A1 | 5/2008 | Lindackers et al. |
| 2008/0127176 A1 | 5/2008 | Lee et al. |
| 2008/0129450 A1 | 6/2008 | Riegebauer |
| 2008/0129463 A1 | 6/2008 | Tuttle |
| 2008/0142588 A1 | 6/2008 | Blum |
| 2008/0148351 A1 | 6/2008 | Bhatia et al. |
| 2008/0149705 A1 | 6/2008 | Giobbi et al. |
| 2008/0150678 A1 | 6/2008 | Giobbi et al. |
| 2008/0156866 A1 | 7/2008 | McNeal |
| 2008/0164997 A1 | 7/2008 | Aritsuka et al. |
| 2008/0169909 A1 | 7/2008 | Park et al. |
| 2008/0180213 A1* | 7/2008 | Flax ................... G16H 10/60 |
| | | 704/E15.047 |
| 2008/0186166 A1 | 8/2008 | Zhou et al. |
| 2008/0188308 A1 | 8/2008 | Shepherd et al. |
| 2008/0195863 A1 | 8/2008 | Kennedy |
| 2008/0201768 A1 | 8/2008 | Koo et al. |
| 2008/0203107 A1 | 8/2008 | Conley et al. |
| 2008/0208016 A1 | 8/2008 | Hughes et al. |
| 2008/0209571 A1 | 8/2008 | Bhaskar et al. |
| 2008/0218416 A1 | 9/2008 | Handy et al. |
| 2008/0222701 A1 | 9/2008 | Saaranen et al. |
| 2008/0223918 A1 | 9/2008 | Williams et al. |
| 2008/0228524 A1 | 9/2008 | Brown |
| 2008/0235144 A1 | 9/2008 | Phillips |
| 2008/0238625 A1 | 10/2008 | Rofougaran et al. |
| 2008/0250388 A1 | 10/2008 | Meyer et al. |
| 2008/0251579 A1 | 10/2008 | Larsen |
| 2008/0278325 A1 | 11/2008 | Zimman et al. |
| 2008/0289030 A1 | 11/2008 | Poplett |
| 2008/0289032 A1 | 11/2008 | Aoki et al. |
| 2008/0303637 A1 | 12/2008 | Gelbman et al. |
| 2008/0313728 A1 | 12/2008 | Pandrangi et al. |
| 2008/0314971 A1 | 12/2008 | Faith et al. |
| 2008/0316045 A1 | 12/2008 | Sriharto et al. |
| 2009/0002134 A1 | 1/2009 | McAllister |
| 2009/0013191 A1 | 1/2009 | Popowski |
| 2009/0016573 A1 | 1/2009 | Mcafee et al. |
| 2009/0024584 A1 | 1/2009 | Dharap et al. |
| 2009/0033464 A1 | 2/2009 | Friedrich |
| 2009/0033485 A1 | 2/2009 | Naeve et al. |
| 2009/0036164 A1 | 2/2009 | Rowley |
| 2009/0041309 A1 | 2/2009 | Kim et al. |
| 2009/0045916 A1 | 2/2009 | Nitzan et al. |
| 2009/0052389 A1 | 2/2009 | Qin et al. |
| 2009/0070146 A1 | 3/2009 | Haider et al. |
| 2009/0076849 A1 | 3/2009 | Diller |
| 2009/0081996 A1 | 3/2009 | Duggal et al. |
| 2009/0085724 A1 | 4/2009 | Naressi et al. |
| 2009/0094681 A1 | 4/2009 | Sadler et al. |
| 2009/0096580 A1 | 4/2009 | Paananen |
| 2009/0121890 A1 | 5/2009 | Brown et al. |
| 2009/0125401 A1 | 5/2009 | Beenau et al. |
| 2009/0140045 A1 | 6/2009 | Evans |
| 2009/0157512 A1 | 6/2009 | King |
| 2009/0165123 A1 | 6/2009 | Giobbi |
| 2009/0176566 A1 | 7/2009 | Kelly |
| 2009/0177495 A1 | 7/2009 | Abousy et al. |
| 2009/0195461 A1 | 8/2009 | Hirt |
| 2009/0199206 A1 | 8/2009 | Finkenzeller et al. |
| 2009/0206992 A1 | 8/2009 | Giobbi et al. |
| 2009/0232362 A1 | 9/2009 | Otsubo et al. |
| 2009/0237245 A1 | 9/2009 | Brinton et al. |
| 2009/0237253 A1 | 9/2009 | Neuwirth |
| 2009/0239667 A1 | 9/2009 | Rowe et al. |
| 2009/0253516 A1 | 10/2009 | Hartmann et al. |
| 2009/0254448 A1 | 10/2009 | Giobbi |
| 2009/0254971 A1 | 10/2009 | Herz et al. |
| 2009/0264712 A1 | 10/2009 | Baldus et al. |
| 2009/0310514 A1 | 12/2009 | Jeon et al. |
| 2009/0313689 A1 | 12/2009 | Nystroem et al. |
| 2009/0319788 A1 | 12/2009 | Zick et al. |
| 2009/0320118 A1 | 12/2009 | Mueller et al. |

(56) References Cited

U.S. PATENT DOCUMENTS

| | | |
|---|---|---|
| 2009/0322510 A1 | 12/2009 | Berger et al. |
| 2009/0328182 A1 | 12/2009 | Malakapalli et al. |
| 2010/0005526 A1 | 1/2010 | Tsuji et al. |
| 2010/0007498 A1 | 1/2010 | Jackson |
| 2010/0022308 A1 | 1/2010 | Hartmann et al. |
| 2010/0023074 A1 | 1/2010 | Powers et al. |
| 2010/0037255 A1 | 2/2010 | Sheehan et al. |
| 2010/0062743 A1 | 3/2010 | Jonsson |
| 2010/0077214 A1 | 3/2010 | Jogand-Coulomb et al. |
| 2010/0091987 A1 | 4/2010 | Takahashi et al. |
| 2010/0117794 A1 | 5/2010 | Adams et al. |
| 2010/0134257 A1 | 6/2010 | Puleston et al. |
| 2010/0169442 A1 | 7/2010 | Liu et al. |
| 2010/0169964 A1 | 7/2010 | Liu et al. |
| 2010/0172567 A1 | 7/2010 | Prokoski |
| 2010/0174911 A1 | 7/2010 | Isshiki |
| 2010/0188226 A1 | 7/2010 | Seder et al. |
| 2010/0214100 A1 | 8/2010 | Page |
| 2010/0277283 A1 | 11/2010 | Burkart et al. |
| 2010/0277286 A1 | 11/2010 | Burkart et al. |
| 2010/0291896 A1 | 11/2010 | Corda |
| 2010/0305843 A1 | 12/2010 | Yan et al. |
| 2010/0328033 A1 | 12/2010 | Kamei |
| 2011/0072034 A1 | 3/2011 | Sly et al. |
| 2011/0072132 A1 | 3/2011 | Shafer et al. |
| 2011/0082735 A1 | 4/2011 | Kannan et al. |
| 2011/0085287 A1 | 4/2011 | Ebrom et al. |
| 2011/0091136 A1 | 4/2011 | Danch et al. |
| 2011/0116358 A9 | 5/2011 | Li et al. |
| 2011/0126188 A1 | 5/2011 | Bernstein et al. |
| 2011/0221568 A1 | 9/2011 | Giobbi |
| 2011/0227740 A1 | 9/2011 | Wohltjen |
| 2011/0238517 A1 | 9/2011 | Ramalingam et al. |
| 2011/0246790 A1 | 10/2011 | Koh et al. |
| 2011/0266348 A1 | 11/2011 | Denniston, Jr. |
| 2011/0307599 A1 | 12/2011 | Saretto et al. |
| 2012/0028609 A1 | 2/2012 | Hruska |
| 2012/0030006 A1 | 2/2012 | Yoder et al. |
| 2012/0069776 A1 | 3/2012 | Caldwell et al. |
| 2012/0086571 A1 | 4/2012 | Scalisi et al. |
| 2012/0182123 A1 | 7/2012 | Butler et al. |
| 2012/0212322 A1 | 8/2012 | Idsoee |
| 2012/0226451 A1 | 9/2012 | Bagot et al. |
| 2012/0226565 A1 | 9/2012 | Drozd |
| 2012/0226907 A1 | 9/2012 | Hohberger et al. |
| 2012/0238287 A1 | 9/2012 | Scherzer |
| 2012/0278188 A1 | 11/2012 | Attar et al. |
| 2012/0300753 A1 | 11/2012 | Brown et al. |
| 2012/0310720 A1 | 12/2012 | Balsan et al. |
| 2013/0019295 A1 | 1/2013 | Park et al. |
| 2013/0019323 A1 | 1/2013 | Arvidsson et al. |
| 2013/0044111 A1 | 2/2013 | Vangilder et al. |
| 2013/0111543 A1 | 5/2013 | Brown et al. |
| 2013/0135082 A1 | 5/2013 | Xian et al. |
| 2013/0179201 A1 | 7/2013 | Fuerstenberg et al. |
| 2013/0219186 A1 | 8/2013 | Giobbi et al. |
| 2013/0276140 A1 | 10/2013 | Coffing et al. |
| 2013/0277425 A1 | 10/2013 | Sharma et al. |
| 2013/0297514 A1 | 11/2013 | Giobbi |
| 2013/0312082 A1 | 11/2013 | Izu et al. |
| 2013/0315210 A1 | 11/2013 | Brown et al. |
| 2013/0331063 A1 | 12/2013 | Cormier et al. |
| 2014/0074696 A1 | 3/2014 | Glaser |
| 2014/0147018 A1 | 5/2014 | Argue et al. |
| 2014/0266604 A1 | 9/2014 | Masood et al. |
| 2014/0266713 A1 | 9/2014 | Sehgal et al. |
| 2014/0337920 A1 | 11/2014 | Giobbi |
| 2015/0026480 A1 | 1/2015 | Giobbi et al. |
| 2015/0039451 A1 | 2/2015 | Bonfiglio |
| 2015/0138330 A1 | 5/2015 | Krishnamoorthi |
| 2015/0294293 A1 | 10/2015 | Signarsson |
| 2015/0310385 A1 | 10/2015 | King et al. |
| 2015/0310440 A1 | 10/2015 | Hynes et al. |
| 2016/0005020 A1 | 1/2016 | Fernando et al. |
| 2016/0093081 A1 | 3/2016 | Kim et al. |
| 2016/0133123 A1 | 5/2016 | Giobbi et al. |
| 2016/0171200 A1 | 6/2016 | Giobbi |
| 2016/0203349 A1 | 7/2016 | Giobbi |
| 2016/0205682 A1 | 7/2016 | Brown et al. |
| 2016/0210614 A1 | 7/2016 | Hall |
| 2016/0300236 A1 | 10/2016 | Wiley et al. |
| 2016/0306956 A1 | 10/2016 | Giobbi |
| 2017/0041315 A1 | 2/2017 | Giobbi |
| 2017/0085564 A1 | 3/2017 | Giobbi et al. |
| 2017/0091548 A1 | 3/2017 | Agrawal et al. |
| 2017/0270738 A1 | 9/2017 | Giobbi |
| 2017/0309165 A1 | 10/2017 | Brown et al. |
| 2017/0353500 A1 | 12/2017 | Jacobsen et al. |
| 2018/0019998 A1 | 1/2018 | Giobbi |
| 2018/0129799 A1 | 5/2018 | Giobbi |
| 2018/0322718 A1 | 11/2018 | Qian et al. |
| 2018/0357475 A1 | 12/2018 | Honda et al. |
| 2019/0065721 A1 | 2/2019 | Giobbi |
| 2019/0172281 A1 | 6/2019 | Einberg et al. |
| 2019/0260724 A1 | 8/2019 | Hefetz et al. |
| 2019/0289562 A1 | 9/2019 | Brown |
| 2020/0351873 A1 | 11/2020 | Brown et al. |
| 2021/0219869 A1 | 7/2021 | Ryu et al. |
| 2022/0210643 A1 | 6/2022 | Hynds et al. |

FOREIGN PATENT DOCUMENTS

| | | |
|---|---|---|
| WO | 99/56429 A1 | 11/1999 |
| WO | 00/62505 A1 | 10/2000 |
| WO | 01/22724 A1 | 3/2001 |
| WO | 01/35334 A1 | 5/2001 |
| WO | 01/75876 A1 | 10/2001 |
| WO | 01/77790 A1 | 10/2001 |
| WO | 2004/010774 A1 | 2/2004 |
| WO | 2004/038563 A2 | 5/2004 |
| WO | 2005/031663 A2 | 4/2005 |
| WO | 2005/050450 A1 | 6/2005 |
| WO | 2005/086802 A2 | 9/2005 |
| WO | 2007/087558 A2 | 8/2007 |

OTHER PUBLICATIONS

Machine translation of JPH10049604, 27 pages.

Mciver et al., "Identification and Verification Working Together," Bioscrypt, White Paper: Identification and Verification Working Together, Aug. 27, 2004, retrieved from www.ibia.org/membersadmin/whitepapers/pdf/15/Identification%20and%20Verification%20Working%20Together.pdf on Jan. 7, 2007, 5 pgs.

Micronas, "Micronas and Thomson Multimedia Showcase a New Copy Protection System that Will Drive the Future of Digital Television," www.micronas.com: Jan. 8, 2002, 3 pgs.

Muller, "Desktop Encyclopedia of the Internet," 1999, Artech House Inc., Norwood, MA, all pages.

National Criminal Justice Reference Service, "Antenna Types," Dec. 11, 2006, online at http://ncjrs.gov/pdfffiles1/nij/185030b.pdf, retrieved from http://web.archive.erg/web/*/http://www.ncjrs.gov/pdffiles1/nij/185030b.pdf on Jan. 12, 2011, 1 pg.

Nel et al., "Generation of Keys for use with the Digital Signature Standard (DSS)," Communications and Signal Processing, Proceedings of the 1993 IEEE South African Symposium, Aug. 6, 1993, pp. 6-11.

Nerd Vitiles, "magicJack: Could It Be the Asterisk Killer?" Aug. 1, 2007, retrieved from http://nerdvittles.com/index.php?p=187 on or before Oct. 11, 2011, 2 pgs.

Nilsson et al., "Match-on-Card for Java Cards," Precise Biometrics, white paper, Apr. 2004, retrieved from www.ibia.org/membersadmin/whitepapers/pdf/17/Precise%20Match-on-Card%20for%20Java%20Cards.pdf on Jan. 7, 2007, 5 pgs.

Noore, "Highly Robust Biometric Smart Card Design." IEEE Transactions on Consumer Electronics, vol. 46, No. 4, Nov. 2000, pp. 1059-1063.

Nordin, "Match-on-Card Technology," Precise Biometrics, white paper, Apr. 2004, retrieved from www.ibia.org/membersadmin/whitepapers/pdf/17/Precise%20Match-on-Card%20technology.pdf on Jan. 7, 2007, 7 pgs.

(56) References Cited

OTHER PUBLICATIONS

Paget, "The Security Behind Secure Extranets," Enterprise Systems Journal, vol. 14, No. 12, Dec. 1999, 4 pgs.
Pash, "Automate proximity and location-based computer actions," Jun. 5, 2007, retrieved from http://lifehacker.com/265822/automate-proximity-and-location+based-computer-actionson or before Oct. 11, 2011, 3 pgs.
Pope et al., "Oasis Digital Signature Services: Digital Signing without the Headaches," IEEE Internet Computing, vol. 10, Sep./Oct. 2006, pp. 81-84.
Saflink Corporation, "SAFModule (Trademark): A Look Into Strong Authentication," white paper, retrieved from www.ibia.org/membersadmin/whilepapers/pdf/6/SAFmod_WP.pdf on Jan. 7, 2007, 8 pgs.
Sapsford, "E-Business: Sound Waves Could Help Ease Web-Fraud Woes," Wall Street Journal, Aug. 14, 2000, p. B1.
Singh et al. "A Constraint-Based Biometric Scheme on ATM and Swiping Machine." 2016 International Conference on Computational Techniques in Information and Communication Technologies (ICCTICT), Mar. 11, 2016, pp. 74-79.
Smart Card Alliance, "Alliance Activities: Publications: Identity: Identity Management Systems, Smart Cards and Privacy," 1997-2007, retrieved from www smartcardalliance.org/pages/publications-identity on Jan. 7, 2007, 3 pgs.
Smart Card Alliance, "Contactless Technology for Secure Physical Access: Technology and Standards Choices," Smart Card Alliance, Oct. 2002, pp. 1-48.
Smart Card Alliance, "Smart Cards and Biometrics White Paper: Smart Card Alliance," May 2002, retrieved from http://www.securitymanagement.com/library/smartcard faqtech0802.pdf on Jan. 7, 2007, 7 pgs.
Splashid, "SplashID—Secure Password Manager for PDA's and Smartphones," Mar. 8, 2007, retrieved from http://www.splashdata/com/splashid/ via http://www.archive.org/ on or before Oct. 11, 2011, 2 pgs.
Srivastava, "Is internet security a major issue with respect to the slow acceptance rate of digital signatures," Jan. 2, 2005, Computer Law & Security Report, pp. 392-404.
Thomson Multimedia, "Thomson multimedia unveils copy protection proposal designed to provide additional layer of digital content security," retrieved from www.thompson-multimedia.com/gb/06/c01/010530.htm on Mar. 4, 2002, May 30, 2001, 2 pgs.
Unixhelp, "What is a file?" Apr. 30, 1998, retrieved from unixhelp.ed.ac.uk/editors/whatisafile.html accessed Mar. 11, 2010 via http://waybackmachine.org/19980615000000*/http://unixhelp.ed.ac.uk/editors/whatisafile.html on Mar. 11, 2011, 1 pg.
Vainio, "Bluetooth Security," Helsinki University of Technology, May 25, 2000, 17 pgs.
Van Winkle, "Bluetooth: The King of Connectivity," Laptop Buyer's Guide and Handbook, Jan. 2000, pp. 148-153.
Wade, "Using Fingerprints to Make Payments at POS Slowly Gaining Popularity," Credit Union Journal, International Biometric Group, Apr. 21, 2003, retrieved from http://www.biometricgroup.com/in_the_news/04.21.03.html on Jan. 7, 2007, 3 pgs.
Wallace, "The Internet Unplugged," InformationWeek, vol. 765, No. 22, Dec. 13, 1999, pp. 22-24.
Weber, "In the Age of Napster, Protecting Copyright is a Digital Arms Race," Wall Street Journal, Eastern ed., Jul. 24, 2000, p.B1.
White, "How computers Work," Millennium Edition, 1999, Que Corporation, Indianapolis, IN, all pages.
Yoshida, "Content Protection Plan Targets Wireless Home Networks," EE Times, Jan. 11, 2002, retrieved from www.eetimes.com/story/OEG20020111S0060 on Mar. 4, 2002, 2 pgs.
Thongthammachart et al., "Bluetooth Enables In-door Mobile Location Services," Proceedings of the 57th IEEE Semiannual Vehicular Technology Conference, Apr. 22-25, 2003, 5 pgs.
University of Birmingham, "PRISM: Probabilistic Symbolic Model Checker," at least as early as Aug. 3, 2004, 3 pgs., archived at https://web.archive.org/web/20040803193058/http://www.cs.bham.ac.uk/~dxp/prism/casestudies/index.html.
Weissman, "Indoor Location," Tadlys Ltd. white paper, at least as early as Oct. 31, 2004, 15 pgs., archived at https://web.archive.org/web/20041031125859/http:/www.tadlys.com/media/downloads/Indoors_Location_Systems.pdf.
Zigbee Alliance, "Welcome to the ZigBeeTM Alliance," exemplary web page, at least as early as Sep. 24, 2004, 2 pgs., archived at https://web.archive org/web/20040924045517/http://zigbee org/.
Zigbee Alliance, "ZigBee Specification," ZigBee Document 053474r06, Version 1.0, Dec. 14, 2004, 378 pgs.
Zigbee Alliance, "The ZigBeeTM Buzz Is Growing: New Low-Power Wireless Standard Opens Powerful Possibilities," Electronic Design, Jan. 12, 2004, 12 pgs., archived at https://web.archive.org/web/20040411172015/http:/www.elecdesign.com/Files/29/7186/7186_01.pdf.
Zigbee Alliance, "ZigBeeTM Positioned to Drive Wireless Networking in Building Automation, Industrial and Residential Control and Sensors Markets in 2004," press release, Feb. 17, 2004, 3 pgs., archived at https://web.archive.org/web/20040423220244/http/www.zigbee.org/documents/04036r5ZB_MWG-Momentum-Release_FINAL.pdf.
Agourare et al., "Authentication and location control via RFID analysis,"2009 IEEE Conference on Emerging Technologies & Factory Automation, Sep. 1, 2009, 8 pgs.
Labrou et al., "Wireless Wallet," Proceedings of the First Annual International Conference on Mobile and Ubiquitous Systems: Networking and Services (MobiQuitos '04), IEEE, Aug. 22-26, 2004, 10 pgs.
Anonymous, "Applying Biometrics to Door Access," Security Magazine, Sep. 26, 2002, retrieved from http://www.securitymagazine.com/CDA/Articles/Technologies/3ae610eaa34d8010VgnVCM100000f932a8cO on Jan. 7, 2007, 5 pgs.
Anonymous, "Firecrest Shows How Truly Commercially-Minded Companies Will Exploit the Internet," Computergram International, Jan. 18, 1996, 2 pgs.
Anonymous, "IEEE 802.15.4-2006—Wikipedia, the free encyclopedia," Wikipedia, last modified Mar. 21, 2009, retrieved from http://en.wikipedia.org/wiki/IEEE_802.15.4-2006 on Apr. 30, 2009, 5 pgs.
Antonoff, "Visiting Video Valley," Sound & Vision, Nov. 2001, pp. 116, 118-119.
Apple et al., "Smart Card Setup Guide," 2006, downloaded from http://manuals.info.apple.com/en_US/Smart_Card_Setup_Guide.pdf on or before May 3, 2012, 16 pgs.
Balanis, "Antenna Theory: A Review," Jan. 1992, Proceedings of the IEEE, vol. 80, No. 1, p. 13.
Beaufour, "Personal Servers as Digital Keys," Proceedings of the Second IEEE Annual Conference on Pervasive Computing and Communications (PERCOM'04), Mar. 14-17, 2004, pp. 319-328.
Biopay, LLC, "Frequently Asked Questions (FAQs) About BioPay," retrieved from http://www.biopay.com/faqs-lowes.asp on Jan. 7, 2007, 5 pgs.
Blueproximity, "BlueProximity—Leave it—it's locked, come back, it's back too . . . " Aug. 26, 2007, retrieved from http://blueproximity.sourceforge.net/viahttp://www.archive.org/ on or before Oct. 11, 2011, 1 pg.
Bluetooth Sig, Inc., "Bluetooth," www.bluetooth.com, Jun. 1, 2000, 8 pgs.
Bluetooth Sig, Inc., "Say Hello to Bluetooth," retrieved from www.bluetooth.com, at least as early as Jan. 14, 2005, 4 pgs.
Blum, "Digital Rights Management May Solve the Napster 'Problem,'" Technology Investor, Oct. 2000, pp. 24-27.
Bohrsatom et al., "Automatically unlock PC when entering proximity," Dec. 7, 2005, retrieved from http://salling.com/forums/viewtopic.php?t=3190 on or before Oct. 11, 2011, 3 pgs.
Brown, "Techniques for Privacy and Authentication in Personal Communication Systems," Personal Communications, IEEE, Aug. 1995, vol. 2, No. 4, pp. 6-10.
Chen et al., "On Enhancing Biometric Authentication with Data Protection," KES2000, Fourth International Conference on Knowledge-Based Intelligent Engineering Systems and Allied Technologies, Proceedings (Cat. No. OOTH8516), vol. 1, Aug. 1, 2000, pp. 249-252.

(56) References Cited

OTHER PUBLICATIONS

Cisco Systems, Inc., "Antenna Patterns and Their Meaning," 1992-2007, p. 10.
Costa, "Imation USB 2.0 Micro Hard Drive," Nov. 22, 2005, retrieved from http://www.pcmag.com/article2/0,281 7,1892209,00 asp on or before Oct. 11, 2011, 2 pgs.
Dagan, "Power over Ethernet (PoE) Midspan—The Smart Path to Providign Power for IP Telephony," Product Manager, Systems, Aug. 2005, Power Dsine Inc., 28 pgs.
Dai et al., "Toward Blockchain-Based Accounting and Assurance," Journal of Information Systems, vol. 31, No. 3, Fall 2017, pp. 5-21.
Debow, "Credit/Debit Debuts in Midwest Smart Card Test," Computers in Banking, vol. 6, No. 11, Nov. 1989, pp. 10-13.
Dennis, "Digital Passports Need Not Infringe Civil Liberties," Newsbytes, NA, Dec. 2, 1999, 2 pgs.
Derfler, "How Networks Work," Bestseller Edition, 1996, Ziff-Davis Press, Emeryville, CA, all pages.
Farouk et al., "Authentication Mechanisms in Grid Computing Environment: Comparative Study," IEEE, Oct. 2012, p. 1-6.
Fasca, "S3, via Formalize Agreement," Electronic News, The Circuit, 45(45, Nov. 8, 1999), p. 20.
Giobbi, Specification of U.S. Appl. No. 60/824,758, filed Sep. 6, 2006, all pages.
Govindan et al. "Real Time Security Management Using RFID, Biometric and Smart Messages." 2009 3rd International Conference on Anti-Counterfeiting, Security, and Identification in Communication, Aug. 20, 2009, pp. 282-285.
Gralla, "How the Internet works," Millennium Edition, 1999, Que Corporation, Indianapolis, IN, all pages.
Hendron, "File Security, Keychains, Encryption, and More with Mac OS X (10.3+)" Apr. 4, 2005, downloaded from http://www.johnhendron.net/documents/OSX_Security.pdf on or before May 3, 2012, 30 pgs.
IEEE Computer Society, "IEEE Std 802.15.4 (Trade Mark)—Part 15.4: Wireless Medium Access Control (MAC) and Physical Layer (PHY) Specifications for Low-Rate Wireless Personal Area Networks (LR-WPANs)," The Institute of electrical and Electronics Engineers, Inc., New York, NY, Oct. 1, 2003, 679 pgs.
International Search Report and Written Opinion for International Application No. PCT/US04/38124, dated Apr. 7, 2005, 10 pgs.
International Search Report and Written Opinion for International Application No. PCT/US05/00349, dated Mar. 19, 2008, 10 pgs.
International Search Report and Written Opinion for International Application No. PCT/US05/07535, dated Dec. 6, 2005, 6 pgs.
International Search Report and Written Opinion for International Application No. PCT/US05/43447, dated Feb. 22, 2007, 7 pgs.
International Search Report and Written Opinion for International Application No. PCT/US05/46843, dated Mar. 1, 2007, 10 pgs.
International Search Report and Written Opinion for International Application No. PCT/US07/11102, dated Oct. 3, 2008, 11 pgs.
International Search Report and Written Opinion for International Application No. PCT/US07/11103, dated Apr. 23, 2008, 9 pgs.
International Search Report and Written Opinion for International Application No. PCT/US07/11104, dated Jun. 26, 2008, 9 pgs.
International Search Report and Written Opinion for International Application No. PCT/US07/11105, dated Oct. 20, 2008, 10 pgs.
International Search Report and Written Opinion for International Application No. PCT/US08/83060, dated Dec. 29, 2008, 9 pgs.
International Search Report and Written Opinion for International Application No. PCT/US08/87835, dated Feb. 11, 2009, 8 pgs.
International Search Report and Written Opinion for International Application No. PCT/US09/34095, dated Mar. 25, 2009, 11 pgs.
International Search Report and Written Opinion for International Application No. PCT/US2009/039943, dated Jun. 1, 2009, 9 pgs.
International Search Report and Written Opinion for International Application No. PCT/US2014/037609, dated Dec. 9, 2014, 13 pgs.
International Search Report for International Application No. PCT/US2001/049916, dated Apr. 25, 2002, 1 pg.
Jeyaprakash et al., "Secured Smart Card Using Palm Vein Biometric On-Card-Process," 2008 International Conference on Convergence and Hybrid Information Technology, 2008, pp. 548-551.
Katz et al., "Smart Cards and Biometrics in Privacy-Sensitive Secure Personal Identification System," May 2002, Smart Card Alliance, p. 1-29.
Kontzer, "Thomson Bets on Smart Cards for Video Encryption," www.informationweek.com, Jun. 7, 2001, 1 pg.
Lake, "Downloading for Dollars: Who said buying music off the Net would be easy?" Sound & Vision, Nov. 2000, pp. 137-138.
Lee et al., "Effects of dielectric superstrales on a two-layer electromagnetically coupled patch antenna," Antennas and Propagation Society International Symposium, Jun. 1989, AP-S. Digest, vol. 2, pp. 26-30, found at http://ieeexplore.ieee.org/stamp/stamp.jsp?tp=&arnumber=1347.
Lewis, "Sony and Visa in On-Line Entertainment Venture," New York Times, vol. 145, Thurs. Ed., Nov. 16, 1995, 1 pg.
Serrao et al., "Protecting Digital Music Delivery and Consumption using the OCCAMM Project Framework," Proceedings of the Second International Conference on Web Delivering of Music, 2002, pp. 38-45, doi: 10.1109/WDM.2002.1176192.
David et al., Security Issues for Contactless Smart Cards, Sep. 1, 1997, conference paper, available online at https://link.springer.com/chapter/10.1007/BFb0054029, 6 pgs.
Kuhn et al., Introduction to Public Key Technology and the Federal PKI Infrastructure, Feb. 26, 2001, National Institute of Standards and Technology, 54 pgs.
Petition for Inter Partes Review of U.S. Pat. No. 9,049,188, Aug. 26, 2021, 800 pgs.
Petition for Inter Partes Review of U.S. Pat. No. 9,235,700, Aug. 26, 2021, 466 pgs.
Request for Ex Parte Reexamination of U.S. Pat. No. 10,698,989, Jun. 8, 2022, 1505 pgs.
Request for Ex Parte Reexamination of U.S. Pat. No. 8,352,730, Jun. 8, 2022, 1401 pgs.
Request for Ex Parte Reexamination of U.S. Pat. No. 9,298,905, Jun. 8, 2022, 1123 pgs.
Smart Card Alliance, Contactless Payment and the Retail Point of Sale: Applications, Technologies and Transaction Models, Mar. 1, 2003, a Smart Card Alliance Report, 50 pgs.
Smart Card Alliance, Smart Card Alliance—The Alliance, Jan. 22, 2001, http://www.smartcardalliance.org, 1 pg.
Beaufour et al., "Personal servers as digital keys," Proceedings of the Second IEEE Annual Conference on Pervasive Computing and Communications, 2004, pp. 319-328, doi: 10.1109/PERCOM.2004.1276869.
Callaway, Wireless Sensor Networks: Architectures and Protocols, Jan. 1, 2004, Auerbach Publications, 366 pgs.
Dvorak, IEEE 802.15.4 and Zigbee Overview, Sep. 27, 2005, Motorola, 26 pgs.
Hester et al., "neuRFon(TM) Netform: A Self-Organizing Wireless Sensor Network", Oct. 14, 2002, Proceedings of the Eleventh International Conference on Computer Communications and Networks, pp. 364-369.
Honkanen et al., "Low End Extension for Bluetooth", Sep. 19, 2004, Proceedings of the 2004 IEEE Radio and Wireless Conference, Atlanta, GA, pp. 199-202.
Jonker et al., "Digital rights management in consumer electronics products," IEEE Signal Processing Magazine, vol. 21, No. 2, pp. 82-91, Mar. 2004, doi: 10.1109/MSP.2004.1276116.
Schneier, Applied Cryptography, Second Edition: Protocols, Algorithms, and Source Doe in C, Jan. 1, 1996, John Wiley & Sons, Inc., 1027 pgs.
Adams, "Designing with 802.15.4 and Zigbee," presented at Industrial Wireless Applications Summit, San Diego, California, Mar. 9, 2004, 22 pgs.
Adams, "Meet the ZigBee Standard," Sensors Online, Jun. 2003, 7 pgs., archived at https://web.archive.org/web/20031008191032/http://sensorsmag.com/articles/0603/14/pf_main.shtml.
Adams, "Zigbee vital in industrial applications," EE Times, Jul. 29, 2003, 3 pgs., archived at https://web.archive.org/web/20031013062940/http:/www.eetimes.com/story/OEG20030727S0002.

(56) References Cited

OTHER PUBLICATIONS

Blip Systems, "Mar. 8, 2004—Bluetooth at the office?" at least as early as Oct. 11, 2004, archived at https://web.archive.org/web/20041011094320/http:/www.blipsystems.com/Default.asp?ID=16&M=News&PID=25&NewsID=9.
Blip Systems, "BlipManager," at least as early as May 17, 2004, 1 pg., archived at https://web.archive.org/web/20040517050728/http:/www.blipsystems.com/Default.asp?ID=11.
Blip Systems, "BlipMobility," at least as early as Apr. 7, 2004, archived at https://web.archive.org/web/20040407212934/http:/www.blipsystems.com/Default.asp?ID=118.
Blip Systems, "BlipNet API," at least as early as May 18, 2004, 1 pg., archived at https://web.archive.org/web/20040518060132/http:/www.blipsystems.com/Default.asp?ID=92.
Blip Systems, "BlipNet Explore a wireless world . . . of great opportunities," brochure available Sep. 2002, 6 pgs., availabe online at https://web.archive.org/web/20031012184406/http:/www.blipsystems.com/products_blipnet.shtml.
Blip Systems, "BlipNet Technical Overview," Mar. 2003, 30 pgs., archived at https://web.archive.org/web/20031012184406/http:/www.blipsystems.com/products_blipnet.shtml.
Blip Systems, "BlipNode," at least as early as May 16, 2004, 1 pg., archived at https://web.archive.org/web/20040516001554/http:/www.blipsystems.com/Default.asp?ID=10.
Blip Systems, "BlipServer," at least as early as May 17, 2004, 1 pg., archived at https://web.archive.org/web/20040517044955/http:/www.blipsystems.com/Default.asp?ID-9.
Blip Systems, "Bluetooth Networks: Products: Bluetooth infracture," product description, at least as early as Oct. 2003, archived at https://web.archive.org/web/20031012184406/http:/www.blipsystems.com/products_blipnet.shtml.
Blip Systems, "Product Information—BlipNet—Presentation of BlipNet 1.0—A Bluetooth Access System," Aug. 2002,2 pgs., archived at https://web.archive.org/web/20031012184406/http:/www.blipsystems.com/products_blipnet.shtml.
Bluetooth Sig, Inc. "Specification of the Bluetooth System," Version 1.2, Nov. 5, 2003, 82 pgs., archived at https://web.archive.org/web/20031119092849/http:/www.bluetooth.com/dev/spec.v12.asp.
Callaway, "Wireless Sensor Networks: Architectures and Protocols," book description, Motorola Labs, Auerbach Publications, Aug. 26, 2003, 3 pgs., archived at https://web.archive.org/web/20031023101953/http:/www.crcpress.com/shopping_cart/products/product_detail.asp?sku=AU1823.
Chi et al., "Industrial Wireless Sensor Networking: A Market Dynamics Study," ON World, Jun. 28, 2004, 5 pgs., archived at https://web.archive.org/web/20040710182216/http:/onworld.com:80/html/industrialwirelesssensor.htm.
Disclosed Anonymously (Method and Apparatus for Mobile Identity Authentication)., An IP.com Prior Art Database Technical IP.com No. IPCOM000194545D., IP.com Electronic Publication Date: Mar. 29, 2010 (Year: 2010).
Duflot et al., "A Formal Analysis of Bluetooth Device Discovery," presented at the 1st International Symposium on Leveraging Applications of Formal Methods (ISOLA'04), Oct. 30-Nov. 2, 2004, Paphos, Cyprus, and published in the International Journal on Software Tools for Technology Transfer 8, pp. 621-632, 16 pgs., https://doi.org/10.1007/s10009-006-0014-x.
Eshed, "Bluetooth Wireless Technology Application for the Retail Market," published at www.tadlys.com on May 2001, 8 pgs.
Freescale Semicondcutor, Inc., "Freescale Events," see ZigBee Open House Event, Aug. 18, 2004, 6 pgs., archived at https://web.archive.org/web/20040909082726/https://www.freescale.com/webapp/sps/site/overview.jsp?nodeId=02XPgQ7JgbBqJQ#zigbee_openhouse_04.
Freescale Semiconductor, Inc., "Overview," ZigBee General Information, at least as early as Aug. 17, 2004, 1 pg., archived at https://web.archive.org/web/20040817210006/http:/www.freescale.com/webapp/sps/site/overview.jsp?nodeId=02XPgQhHPRjdyB37087725.

Freescale Semiconductor, Inc., "ZigBeeTM," Freescale Semiconductor Wireless Standards, at least as early as Aug. 18, 2004, 2 pgs., archived at https://web.archive.org/web/20040818075046/http:/www.freescale.com/webapp/sps/site/overview.jsp?nodeId=02XPgQhHPRjdyB.
Freescale Semiconductor, Inc., "ZigBeeTM," Freescale Semiconductor Wireless Standards, at least as early as Jun. 11, 2004, 2 pgs., archived at https://web.archive.org/web/20040611051834/http:/e-www.motorola.com/webapp/sps/site/overview.jsp?nodeId=02XPgQhHPRjdyB.
Freescale Semiconductor, Inc., "Freescale's ZigBeeTM-ready Platform Wins Sensors Magazine Best of Sensors Expo Award," Freescale Semiconductor Wireless, at least as early as Aug. 17, 2004, 1 pg., archived at https://web.archive.org/web/20040817203409mp_/http:/www.freescale.com/webapp/sps/site/overview.jsp?nodeId=02XPgQ6988.
Freescale Semiconductor, Inc., "ZigBee Alliance Successfully Concludes First Multi-node Network Test," press release, Jul. 6, 2004, 2 pgs., archived at https://web.archive.org/web/20040717113733/http:/www.zigbee.org/documents/First-Multi-Node_Testing_FINAL_000.pdf.
Freescale Semiconductor, Inc., "ZigBeeTM Technology from Freescale," Freescale Semiconductor, Inc. white paper, 2004, 4 pgs., archived at https://web.archive.org/web/20050513024652/http:/www.freescale.com/files/wireless_comm/doc/brochure/BRZIGBEETECH.pdf.
Freescale Semiconductor, Inc., "ZRP-1 : ZigBee-ready Platform," at least as early as Oct. 19, 2005, 6 pgs., archived at https://web.archive.org/web/20051019122919/http://www.freescale.com/webapp/sps/site/prod_summary.jsp?code=ZRP-1&nodeId=02XPgQhCQ6m6cy7103.
Freescale Semiconductor, Inc., M68HC08 microcontroller ordering web page, at least as early as Aug. 17, 2004, 5 pgs., archived at https://web.archive.org/web/20040817014804/http:/www.freescale.com/webapp/sps/site/taxonomy.jsp?nodeId=01624684498634.
IBM Corporation, "Tadlys' Bluetooth Wireless Local Network for Corporate," Wireless e-business, at least as early as May 6, 2004, 2 pgs., archived at https://web.archive.org/web/20040621130525/http://www.tadlys.com/media/downloads/Corporate%20PVDEE01005-3.pdf.
IBM Corporation, "Tadlys' Bluetooth Wireless Local Network for Hotspots," Wireless e-business, at least as early as May 6, 2004, 2 pgs., archived at https://web.archive.org/web/20040508123915/http://www.tadlys.com/media/downloads/Hotspots%20PVDEE01006-3.pdf.
IEEE, "IEEE 802.15 WPANTM Task Group 4 (TG4)" exemplary web page, Aug. 24, 2004, 2 pgs., archived at https://web.archive.org/web/20040824085452/http:/www.ieee802.org/15/pub/TG4.html.
Korzeniowski, "First Intelligent, Wireless Consumer Devices About to Hit Market," TechNewsWorld, Jul. 28, 2004, 3 pgs., archived at https://web.archive.org/web/20040821061130/http:/www.technewsworld.com/story/35376.html%20com/.
Malan, "Here come Wireless Sensors," Machine Design, Jun. 10, 2004, 3 pgs., archived at https://web.archive.org/web/20040610131354/http:/www.machinedesign.com/ASP/viewSelectedArticle.asp?strArticleId=56796&strSite=MDSite&Screen=CURRENTISSUE.
MIT Computer Science and Artificial Intelligence Laboratory, "Cricket v2 User Manual," Cricket Project, MIT Computer Science and Artificial Intelligence Lab, Cambridge, MA, Jan. 2005, 57 pgs., available online at https://web.archive.org/web/20041206144922/http:/cricket.csail.mit.edu/v2man.html.
MIT Computer Science and Artificial Intelligence Laboratory, "The Cricket Indoor Location System," at least as early as Nov. 19, 2004, 6 pgs., archived at https://web.archive.org/web/20041119183049/http:/cricket.csail.mit.edu/.
Motorola, Inc., "Motorola First to Demonstrate ZigBee 2.4 GHz Wireless Networking Technology," press release, Mar. 27, 2003, 2 pgs., archived at https://web.archive.org/web/20050205053308/http:/www.motorola.com/mediacenter/news/detail/0, 1958,2743_2228_23,00.html.
Priyantha, "The Cricket Indoor Location System," Ph.D. thesis submitted to Department of Electrical Engineering and Computer Science, Massachusetts Institute of Technology, Jun. 2005, 199 pgs.

(56) References Cited

OTHER PUBLICATIONS

Rodriguez et al., "In-building location using Bluetooth," Proceedings of the International Workshop on Wireless Ad-Hoc Networks (IWWAN 2005), May 23-26, 2005, London, England, 7 pgs.

Tadlys Ltd., "'Hotspot' Gaming Arcade," at least as early as Dec. 9, 2004, 2 pgs., archived at https://web.archive.org/web/20041209234518/http://www.tadlys.com/media/downloads/Tadlys_gaming_arcade.pdf.

Tadlys Ltd., "About Tadlys," at least as early as Apr. 5, 2001, 1 pg., archived at https://web.archive.org/web/20010405044249/http:/www.tadlys.com/about.html.

Tadlys Ltd., "An Advertisers' Dream—From direct marketing to sales," Nov. 2004, 2 pgs., archived at https://web.archive.org/web/20041101092944/http://www.tadlys.com/media/downloads/m-commerce_app.pdf.

Tadlys Ltd., "Bluetooth Glossary," at least as early as Jun. 2004, 12 pgs., archived at https://web.archive.org/web/20040531082349/http://www.tadlys.com/pages/Downloads_content.asp?intGlobalId=1.

Tadlys Ltd., "First Demo of Distribution and Redemption of e-Coupons over Bluetooth," Tadlys Company News and Events, Jun. 5, 2001, 1 pg., archived at https://web.archive.org/web/20040601051516/http://tadlys.com/Pages/news_content.asp?iGlobalID=17.

Tadlys Ltd., "Indoor Location Networks," at least as early as Apr. 3, 2004, 1 pg., archived at https://web.archive.org/web/20040403200221/http:/www.tadlys.com/Pages/Product_content.asp?iGlobalId=2.

Tadlys Ltd., "Operator Systems," at least as early as Nov. 1, 2004, 2 pgs., archived at https://web.archive.org/web/20041101101402/http://www.tadlys.com/media/downloads/operator_network.pdf.

Tadlys Ltd., "Tadlys Announces Range of Bluetooth Access Network Solutions," Tadlys Company News and Events, Jan. 22, 2001, 1 pg., archived at https://web.archive.org/web/20040624122319/http://www.tadlys.com/Pages/news_content.asp?iGlobalID=16.

Tadlys Ltd., "Tadlys' Wire free networking solutions," Feb. 2001, 2 pgs., archived at https://web.archive.org/web/20010204012700/http:/www.tadlys.com/solutions.html.

Tadlys Ltd., "Wireless hospital network," at least as early as Jul. 1, 2004, 2 pgs., archived at https://web.archive.org/web/20040701105046/http://www.tadlys.com/media/downloads/tadlys_hospital_wireless_network.pdf.

Tadlys Ltd., "Wireless Museum Information," at least as early as Dec. 12, 2005, 2 pgs., archived at https://web.archive.org/web/20051212162456/http://www.tadlys.com/media/downloads/Tadlys_wireless_museum_network.pdf.

Tadlys Ltd., "Corporate Systems," at least as early as Nov. 1, 2004, 2 pgs., archived at https://web.archive.org/web/20041101095441/http://www.tadlys.com/media/downloads/Corporate_network.pdf.

Zhang et al., "A User-Centric M-Payment Solution," The ISG-Smart Card Centre and the Information Security Group, Royal Holloway, University of London, Egham, Surrey, TW20 0EX, UK, 2005, 8 pgs.

Petition for Inter Partes Review of U.S. Pat. No. 10,698,989, Aug. 26, 2021, 3356 pgs.

Petition for Inter Partes Review of U.S. Pat. No. 8,352,730, Aug. 26, 2021, 2450 pgs.

Petition for Inter Partes Review of U.S. Pat. No. 9,298,905, Aug. 26, 2021, 1941 pgs.

\* cited by examiner

PROXIMITY-BASED HEALTHCARE MANAGEMENT SYSTEM WITH AUTOMATIC ACCESS TO PRIVATE INFORMATION

CROSS-REFERENCE TO RELATED APPLICATIONS

This application is a continuation of U.S. patent application Ser. No. 13/942,549, titled "Proximity-Based Healthcare Management System with Automatic Access to Private Information," filed Jul. 15, 2013, which is a continuation of and claims priority under 35 U.S.C. § 120 to U.S. patent application Ser. No. 12/371,170, titled "Proximity-Based Healthcare Management System with Automatic Access to Private Information," filed Feb. 13, 2009, which claims the benefit of U.S. Patent Application No. 61/028,847, entitled "ProxMediSys," filed Feb. 14, 2008; U.S. Patent Application No. 61/075,117, entitled "ProxMed," filed Jun. 24, 2008; U.S. Patent Application No. 61/090,234, entitled "ProxMed," filed Aug. 20, 2008; U.S. Patent Application No. 61/090,878, entitled "ProxMed Integrated Proximity-Based Systems for Healthcare," filed Aug. 21, 2008; and U.S. Patent Application No. 61/102,987, entitled "ProxMed," filed Oct. 6, 2008, the entire contents of all of which are incorporated herein by reference.

BACKGROUND

1. Field of Art

This disclosure generally relates to the field of radio frequency identification (RFID) and electronic authentication, and more specifically, to systems and methods for automatic and secure authentication and identification for healthcare.

2. Description of the Related Art

Optimizing patient care is an ever-changing and challenging endeavor. Ensuring quality patient care that is safe, efficient and cost-effective is very important to patients, as well as healthcare providers. Conventional technologies used in the healthcare industry for aiding provider patient care, monitoring patient treatment, receiving and retrieving patient data and monitoring provider activity have not yet provided optimal features to meet these needs. Recently, software application systems have been developed in an attempt to improve patient care and provider performance.

These days, most healthcare facilities utilize electronic software and applications to securely store and efficiently access private patient information. In order to access the patient information, a patient must provide a certain amount of information at each provider visit. The information provided is an attempt to confirm the patient's identity and that the patient's current information is up to date. For example, each time a patient visits his or her doctor for a check-up, he or she typically walks up to the registration table and is greeted by a receptionist or other healthcare provider. The patient must then provide his or her name, the time of the appointment, and the name of the patient's doctor. Often, the receptionist or other healthcare provider must also confirm that the patient's insurance and address information in the system is still correct and up to date. Typically, the patient is then given a medical history form to complete. The patient typically completes a form while waiting for his or her appointment in the waiting room.

Yet another problem in the prior art is the management of and access to electronic records of patients. In most healthcare institutions, healthcare providers can gain access to a patient's electronic records with authorized entry into the healthcare software application system. In order to prove authorization, providers are equipped with a unique username and password. Each time a provider needs to access patient information, they must log in to the system using their unique name and password. Further, each time they are done accessing the electronic records, they must log out of the system to ensure that unauthorized use does not occur. The process of logging in and logging off each time may prove to be quite time-consuming given the number of patients a provider visits in a given day.

Another problem in the prior art is the utilization of equipment in medical facilities and making sure they are deployed in a matter that maximizes their usage and availability. For example, in many hospitals the location of equipment is not tracked and monitored other than by conducting an annual inventory of the equipment. Thus, the medical staff is not aware if some the equipment is not being used or located in an area where it is not required. Thus, tracking of the location of equipment continues to be a problem.

Another problem in the prior art is the monitoring of provider performance to ensure optimal quality patient care. Typically, in many healthcare facilities, an admitted patient is treated by multiple healthcare providers. During the patient's stay, the patient may be seen by multiple healthcare providers and each healthcare provider attends to the patient at multiple times during the day. Further, each provider treats multiple patients while on duty. Current healthcare software applications have been developed to help establish clear and consistent communication between the various providers and ensure optimal record keeping. Given these dynamics, monitoring provider performance and ensuring consistent, safe and effective patient care can be challenging.

Yet another problem in the prior art is the monitoring of patient health status, minimizing response time and ensuring effective and optimal patient care. For example, when a patient is resting in his or her room, she is monitored specialized equipment that is usually wired to a corresponding area of the patient's body. Therefore, the patient can only be monitored while the patient is in his or her hospital room. Further, information about the patient monitored is only displayed at the monitoring equipment itself, or at the nurse's station. These conditions present limitations on the effective monitoring of patients.

The above-defined issues represent serious impediments to quality patient care as well as increasing the cost and adding inefficiency to the delivery of medical services.

BRIEF SUMMARY OF THE INVENTION

A healthcare management system and method provide efficient and secure access to private information. A portable physical device, referred to herein as a Personal Digital Key or "PDK", stores one or more profiles (e.g., a biometric profile) in a tamper-proof memory. The biometric profile is acquired in a secure trusted process and is uniquely associated with an individual that is authorized to use and is associated with the PDK. The PDK can wirelessly transmit the identification information including a unique PDK identification number and the biometric profile over a secure wireless channel for use in an authentication process. The PDK is configured to wirelessly communicate with a reader. A provider interface coupled to the reader, and the reader is further configured to receive profile information from the PDK. The healthcare management system also includes an auto login server configured to communicate with the provider interface to allow access to information in a patient database.

Typically, the reader wirelessly receives the profile from the PDK in order to access private information. In one embodiment, the reader acquires a biometric input from the individual carrying the PDK at the point of request for access. The biometric input can be acquired by, for example, a fingerprint scan, iris scan, retinal scan, palm scan, face scan, DNA analysis, signature analysis, voice analysis or any other input mechanism that provides physical or behavioral characteristics uniquely associated with the individual. The reader compares the biometric profile received from the PDK to the biometric input obtained at the point of the request for access to determine if access should be authorized.

In one embodiment, the auto login server of the healthcare management system is configured to receive profile information from a second PDK while access for the first PDK is being allowed. The received profile information of the second PDK is associated with the first PDK.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Figure 1:
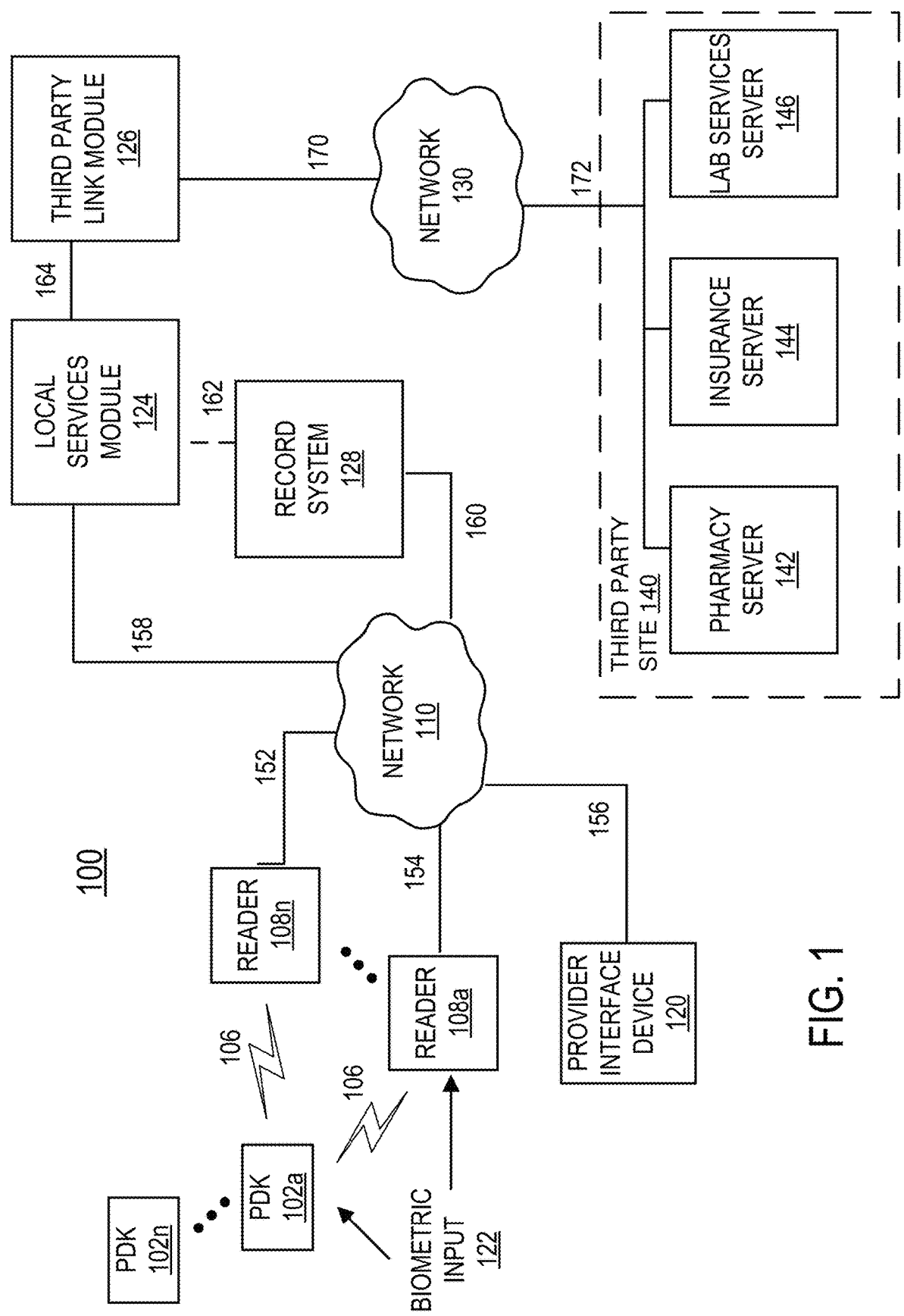
FIG. 1 is a high level block diagram illustrating a system for secure electronic authentication for medical services and applications.

FIG. 1 is a high level block diagram illustrating a system for securely authenticating an individual for transaction-processing and/or access control applications for medical services and applications. The system 100 comprises a Personal Digital Key (PDK) 102, a Reader 108, a network 110, a provider interface device 120, a local services module 124, a third party link module 126, a record system 128, a network 130 and a remote services site 140, which includes pharmacy services 142, insurance services 144 and lab services 146. The Reader 108 is coupled to PDK 102 by a wireless link 106 and coupled to a network 110 by either a wired or wireless link represented by lines 152 and 154. The Reader 108 is also adapted to receive a biometric input 122 from a user and is capable of displaying status to a user. The PDK 102 is also adapted to receive biometric input 122 from a user. The network 110 couples the local services module 124 and third party link module 126 to the Reader 108. The network 110 also couples the local servers 124 and third party link module 126 to the record system 128 via signal lines 158 and 160. In alternative embodiments, different or additional external services, registries or databases (not shown) are coupled to the network 110. In another embodiment, the Reader 108 operates as a standalone device without a connection to the network 110. The network 130 couples the third party link module 126 to the third party site 140 and associated third party services such as the pharmacy server 142, insurance server 144 and lab services server 146.

The system 100 addresses applications where it is important to ensure a specific individual is authorized to perform a given transaction. A transaction as used herein include executing a purchase or financial dealing, enabling access to physical and/or digital items, providing identification or personal information or executing other tasks where it is important to authenticate an individual for use. In one embodiment, the Reader 108 wirelessly receives information stored in the PDK 102 that uniquely identifies the PDK 102 and the individual carrying the PDK 102. In another embodiment, the Reader 108 can also receive a biometric input 122 from the individual. The PDK 102 can also receive biometric input 122 from the individual. Based on the received information, the Reader 108 determines if the transaction should be authorized. Beneficially, the system 100 provides comprehensive authentication without the need for PINs or passwords. Moreover, personal biometric information need not be stored in any local or remote storage database and is only stored on the user's own PDK. Furthermore, in one embodiment, purchase transactions can be efficiently completed without requiring the use of physical credit cards, tokens or other user action beyond initiating the transaction.

The PDK 102 is a compact, portable uniquely identifiable wireless device typically carried by an individual or affixed to an object or device. The PDK 102 stores digital information in a tamper-proof format that uniquely associates the PDK 102 with an individual. Example embodiments of PDKs are described in more detail in U.S. patent application Ser. No. 11/292,330, entitled "Personal Digital Key And Receiver/Decoder Circuit System And Method" filed on Nov. 30, 2005; U.S. patent application Ser. No. 11/620,581 entitled "Wireless Network Synchronization Of Cells And Client Devices On A Network" filed on Jan. 5, 2007; and U.S. patent application Ser. No. 11/620,577 entitled "Dynamic Real-Time Tiered Client Access" filed on Jan. 5, 2007, the entire contents of which are all incorporated herein by reference.

To establish the trust, credibility and confidence of the authentication system, information stored in the PDK 102 is acquired by a process that is trusted, audited and easily verified. The process is ensured by a trusted third-party system, referred to herein as a Notary, that administers the acquisition and storage of information in the PDK 102 according to defined security protocols. In one embodiment, the Notary is a system and/or a trusted individual that witnesses the acquisition and storage either in person or remotely. In another embodiment, the Notary comprises trusted hardware that administers the initialization process by an automated system. Thus, once initialized by the trusted process, the PDK 102 can prove that the information it stores is that of the individual. Example embodiments of the initialization process are described in U.S. patent application Ser. No. 11/744,832 to John Giobbi, et al., entitled "Personal Digital Key Initialization and Registration For Secure Transaction" filed on May 5, 2007, the entire contents of which are incorporated herein by reference.

The Reader 108 wirelessly communicates with the PDK 102 when the PDK 102 is within a proximity zone of the Reader 108. The proximity zone can be, for example, several meters in radius and can be adjusted dynamically by the Reader 108. Thus, in contrast to many conventional RF ID devices, the Reader 108 can detect and communicate with the PDK 102 without requiring the owner to remove the PDK 102 from his/her pocket, wallet, purse, etc. Generally, the Reader 108 receives uniquely identifying information from the PDK 102 and initiates an authentication process for the individual carrying the PDK 102. In one embodiment, the Reader 108 is adapted to receive a biometric input 122 from the individual. The biometric input 122 comprises a representation of physical or behavioral characteristics unique to the individual. For example, the biometric input 122 can include a fingerprint, a palm print, a retinal scan, an iris scan, a photograph, a signature, a voice sample or any other biometric information such as DNA, RNA or their derivatives that can uniquely identify the individual. The Reader 108 compares the biometric input 122 to information received from the PDK 102 to determine if a transaction should be authorized. Alternatively, the biometric input 122 can be obtained by a biometric reader 470 (FIG. 4) on the PDK 102 and transmitted to the Reader 108 for authentication. In additional alternative embodiment, some or all of the authentication process can be performed by the PDK 102 instead of the Reader 108.

Figure 2:
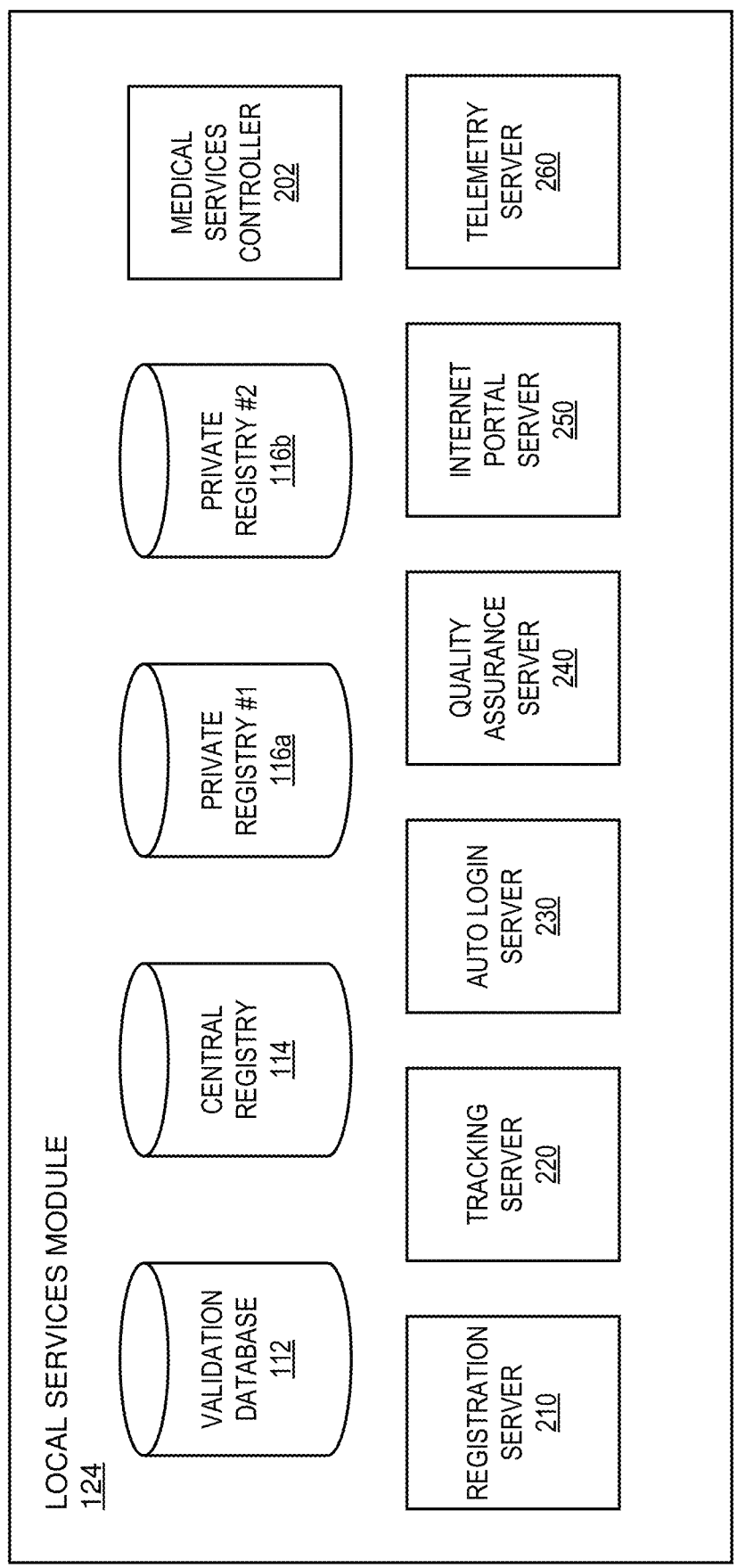
FIG. 2 is a block diagram illustrating one embodiment of a local services module.

The Reader 108 is further communicatively coupled to the network 110 in order to receive and/or transmit information to remote databases for remote authentication. In an alternative embodiment, the Reader 108 includes a non-volatile data storage that can be synchronized with one or more remote databases 112 or registries 114, 116a, 116b (FIG. 2). Such an embodiment alleviates the need for a continuous connection to the network 110 and allows the Reader 108 to operate in a standalone mode and for the local data storage to be updated when a connection is available. For example, a standalone Reader 108 can periodically download updated registry entries and perform authentication locally without any remote lookup.

The record system 128 stores complete personal health records of individuals. An example of a record system 128 is a server or servers of the Google™ Health website, provided by Google Inc. of Mountain View, Calif. and found at www.google.com/health. Another example of a record system 128 is the server or servers of the Microsoft® HealthVault™ provided by Microsoft® Corporation of Redmond, Wash. and found at www.healthvault.com.

The network 110 provides communication between the Reader 108 and the provider interface device 120, local services module 124, and third party link module 126. In alternative embodiments, one or more of these connections may not be present or different or additional network connections may be present. In one embodiment, the network 110 uses standard communications technologies and/or protocols. Thus, the network 110 can include links using technologies such as Ethernet, 802.11, 802.16, integrated services digital network (ISDN), digital subscriber line (DSL), asynchronous transfer mode (ATM), etc. Similarly, the networking protocols used on the network 110 can include the transmission control protocol/Internet protocol (TCP/IP), the hypertext transport protocol (HTTP), the simple mail transfer protocol (SMTP), the file transfer protocol (FTP), etc. The data exchanged over the network 110 can be represented using technologies and/or formats including the hypertext markup language (HTML), the extensible markup language (XML), etc. In addition, all or some of links can be encrypted using conventional encryption technologies such as the secure sockets layer (SSL), Secure HTTP and/or virtual private networks (VPNs). In another embodiment, the entities can use custom and/or dedicated data communications technologies instead of, or in addition to, the ones described above.

Similarly, the network 130 provides communication between the third party link module 126 and third party site 140. In alternative embodiments, one or more of these connections may not be present or different or additional network connections may be present. In one embodiment, the network 130 uses standard communications technologies and/or protocols. Thus, the network 130 can include links using technologies such as Ethernet, 802.11, 802.16, integrated services digital network (ISDN), digital subscriber line (DSL), asynchronous transfer mode (ATM), etc. Similarly, the networking protocols used on the network 110 can include the transmission control protocol/Internet protocol (TCP/IP), the hypertext transport protocol (HTTP), the simple mail transfer protocol (SMTP), the file transfer protocol (FTP), etc. The data exchanged over the network 110 can be represented using technologies and/or formats including the hypertext markup language (HTML), the extensible markup language (XML), etc. In addition, all or some of links can be encrypted using conventional encryption technologies such as the secure sockets layer (SSL), Secure HTTP and/or virtual private networks (VPNs). In another embodiment, the entities can use custom and/or dedicated data communications technologies instead of, or in addition to, the ones described above.

FIG. 2 is a block diagram illustrating a local services module 124, which includes one or more external databases including a validation database 112, a Central Registry 114 and one or more private registries 116a, 116b. The local services module 124 also includes a medical services controller 202, a registration server 210, a tracking server 220, an auto login server 230, a quality assurance server 240, and an internet portal server 250.

The validation database 112 stores additional information that may be used for authorizing a transaction to be processed at the Reader 108. For example, in purchase transactions, the validation database 112 is a credit card validation database that is separate from the merchant providing the sale. Alternatively, a different database may be used to validate different types of purchasing means such as a debit card, ATM card, or bank account number. As another example in healthcare systems, the validation database 112 is a medical record number validation database that separate from the healthcare institution providing the patient care, which provides confirmation of the patient's identification.

The registries 114, 116a, 116b are securely-accessible databases coupled to the network 110 that store, among other items, PDK, Notary, and Reader information. In one embodiment, the registries 114, 116a, 116b do not store biometric information. In an alternative embodiment, the registries 114, 116a, 116b store biometric information in an encoded format that can only be recovered using an algorithm or encoding key stored in the PDK 102. Information stored in the registries 114, 116a, 116b can be accessed by the Reader 108 via the network 110 for use in the authentication process. There are two basic types of registries 114, 116a, 116b illustrated: private registries 116a, 116b and the Central Registry 114. Private registries 116a, 116b are generally established and administered by their controlling entities (e.g., a health care provider, business authority, or other entity administering authentication). Private registries 116a, 116b can be custom configured to meet the specialized and independent needs of each controlling entity. The Central Registry 114 is a single highly-secured, centrally-located database administered by a trusted third-party organization. In one embodiment, all PDKs 102 are registered with the Central Registry 114 and may be optionally registered with one or more selected private registries 116a, 116b. In alternative embodiments, a different number or different types of registries 114, 116a, 116b may be coupled to the network 110.

The medical services controller 202 enables communication between the servers and modules of the local services module 124 and third party link module 126 with the provider interface device 120. In one embodiment, the medical services controller 202 receives information and requests from the provider interface device 120 via the network 110. In another embodiment, the medical services controller 202 coordinates the operation of the various servers and modules of the local services module 124 and third party link module 126. For example, when a patient registration request is received from the Reader 108, the medical services controller 202 routes the request to the registration server 210 and forwards registration confirmation to the appropriate destination, such as the provider interface device 120.

The registration server 210 automates the process of registering new patients and ensures that a patient never needs to register more than once. In one embodiment, the registration server 210 resides in the local services module 124, which is couple to the network via signal line 158. In one embodiment, the registration server 210 is coupled to the validation database 112, central registry 114 and private registries 116a, 116b. The registration server 210 receives patient registration requests from Readers 108 via the network 110 and sends information to the provider interface device 120 also via the network 110. One embodiment of the registration server 210 is described in more detail below with reference to FIG. 16.

The tracking server 220 enables real-time tracking of individuals, equipment and supplies. In one embodiment, the tracking server 220 resides in the local services module 124, which is coupled to the network 110 via signal line 158. The tracking server 220 receives information from the Readers 108 and sends information back to the Readers 108 and PDK 102. One embodiment of the tracking server 220 is described in more detail below with reference to FIG. 18.

The auto login server 230 allows for automated logging in of providers into the healthcare computer system. In one embodiment, the auto login server 230 resides in the local services module 124 and is coupled to the validation database 112, central registry 114 and private registries 116a, 116b. The auto login server receives login requests from the Readers 108 and sends login authorization to the provider interface device 120. One embodiment of the auto login server 230 is described in more detail below with reference to FIG. 20.

The quality assurance server 240 provides recommendations for improving patient care by monitoring treatment and provider activity. In one embodiment, the quality assurance server 240 resides in the local services module. The quality assurance server 240 receives information from the Readers 108 and sends information to the PDK 102 via the Readers 108. The quality assurance server 240 also sends information to the provider interface device 120. The quality assurance server 240 also determines provider salary adjustments by monitoring provider activity. One embodiment of the quality assurance server 240 is described in more detail below with reference to FIG. 22.

The internet portal server 250 provides a consistent interface to the third party link module 126. In one embodiment, the internet portal server 250 resides in the local services module 124. The internet portal server 250 is coupled to the third party link module 126 to allow communication between the third party link module 126 and related third party services, and local services module 124 and provider interface device 120. One embodiment of the internet portal server 250 is described in more detail below with reference to FIG. 24. Such third party services may include accessing a patient's virtual database records or insurance information or sending prescription requests to remote pharmacies. More detailed information describing the components and functions of these servers is described in more detail below.

The telemetry server 260 provides automatic updates and alerts for monitored patients. The telemetry server 260 receives information from Readers 108 and sends information to the provider interface device 120. In one embodiment, the telemetry server 260 resides in the local services module 124. One embodiment of the telemetry server 260 is described in more detail below with reference to FIG. 36.

Figure 3:
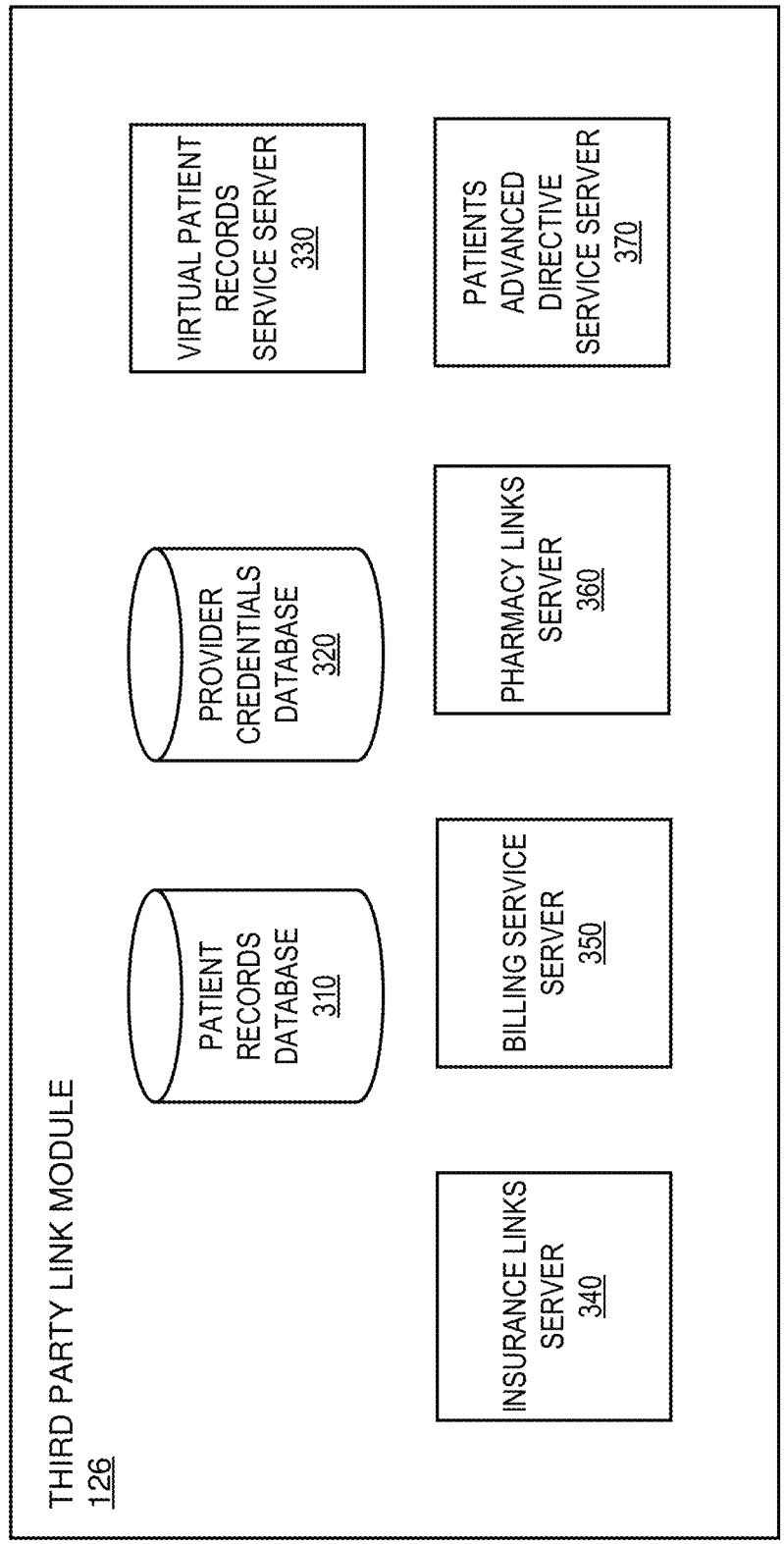
FIG. 3 is a block diagram illustrating one embodiment of a third party link module.

FIG. 3 is a block diagram illustrating a third party link module 126, which includes a patient records database 310, a provider credentials database 320, a virtual patient records service server 330, an insurance links server 340, a billing service server 350, a pharmacy links server 360 and a patient's advanced directive service server 370.

The patient records database 310 stores private patient information. Such information includes a patient's name, medical record number, address, insurance information, prescribed medication, medical and personal history, family information and picture as well as other information related to the patient's health. The patient records database 310 receives requests for patient information and sends patient data to the requesting entity. In one embodiment, the patient records database 310 resides in the third party link module 126 and is coupled to some or all of the modules within the third party link module 126.

The provider credentials database 320 stores information identifying provider information. Such information includes the provider's name, employee number, license number and picture, as well as other information unique to the specific provider. The provider credentials database 320 receives provider authentication requests from the Readers 108 and 720 and sends authentication confirmation to the provider interface device 120. In one embodiment, the provider credentials database 320 resides in the third party link module 126 and is coupled to some or all of the modules within the third party link module 126.

The virtual patient records service server 330 provides a virtual database of a complete record of a patient's medical files by automatically creating links to participating providers' records and enabling centralized and automated access to those records. The virtual patient records service server 330 receives requests for patient information from the provider interface device 120 and retrieves information from the record system 128. In one embodiment, the virtual patient records service server 330 receives request for patient information from the provider interface device 120 via the network 110 and signal lines 156, 158 and retrieves information from the record system 128 via signal line 162. In one embodiment, the record system 128 resides within the local services module 124 and the virtual patient records service server 330 retrieves information from the record system 128 via signal line 164. One embodiment of the virtual patient records service server 330 is described in more detail below with reference to FIG. 26.

The insurance links server 340 provides a portal of communication between the providers and patients' insurance providers and acts in conjunction with the billing services server 350 to update and report patients' billing statements. In one embodiment, the insurance links server 340 resides in the third party link module 126 and is coupled to and communicates with the insurance server 144 to send requests to and receive information from the insurance server 144. The insurance links server 340 is also coupled to the billing services server 350. In one embodiment, the insurance link server 340 is coupled to the internet portal server 250 and communicates with the provider interface device 120 via the internet portal server 250. One embodiment of the insurance links server 340 is described in more detail below with reference to FIG. 28.

The billing service server 350 works in cooperation with the insurance link sever 340 to update patient billing information. In one embodiment, the billing service server 350 resides in the third party link module 126 and is coupled to the insurance links server 340 and patient records database 310. The billing services server receives insurance information from the insurance links server 340 and sends billing information to the patient records database 310. One embodiment of the billing service server 350 is described in more detail below with reference to FIG. 30.

The pharmacy links server 360 provides a portal of communication between health care providers and patients pharmacies. In one embodiment, the pharmacy links server 360 resides in the third party link module 126 is coupled to and communicates with the pharmacy server 142 to send requests to and receive information from the pharmacy server 142. In one embodiment, the pharmacy links server 360 is coupled to the internet portal server 250 and communicates with the provider interface device 120 via the internet portal server 250. One embodiment of the pharmacy links server 360 is described in more detail below with reference to FIG. 32.

The patient's advanced directive service server 370 provides storage for and secure access to patients' advanced directives. An advanced directive is a legal document that allows a person to convey their decisions about end-of-life care. In one embodiment, the patient's advanced directive service server 370 resides in the third party link module 126. The patient's advanced directive service server 370 receives requests from and sends retrieved documents to the provider interface device 120. One embodiment of the patient's advanced directive service server 370 is described in more detail below with reference to FIG. 34. More detailed information describing the components and functions of the aforementioned servers is described in more detail below.

Figure 4:
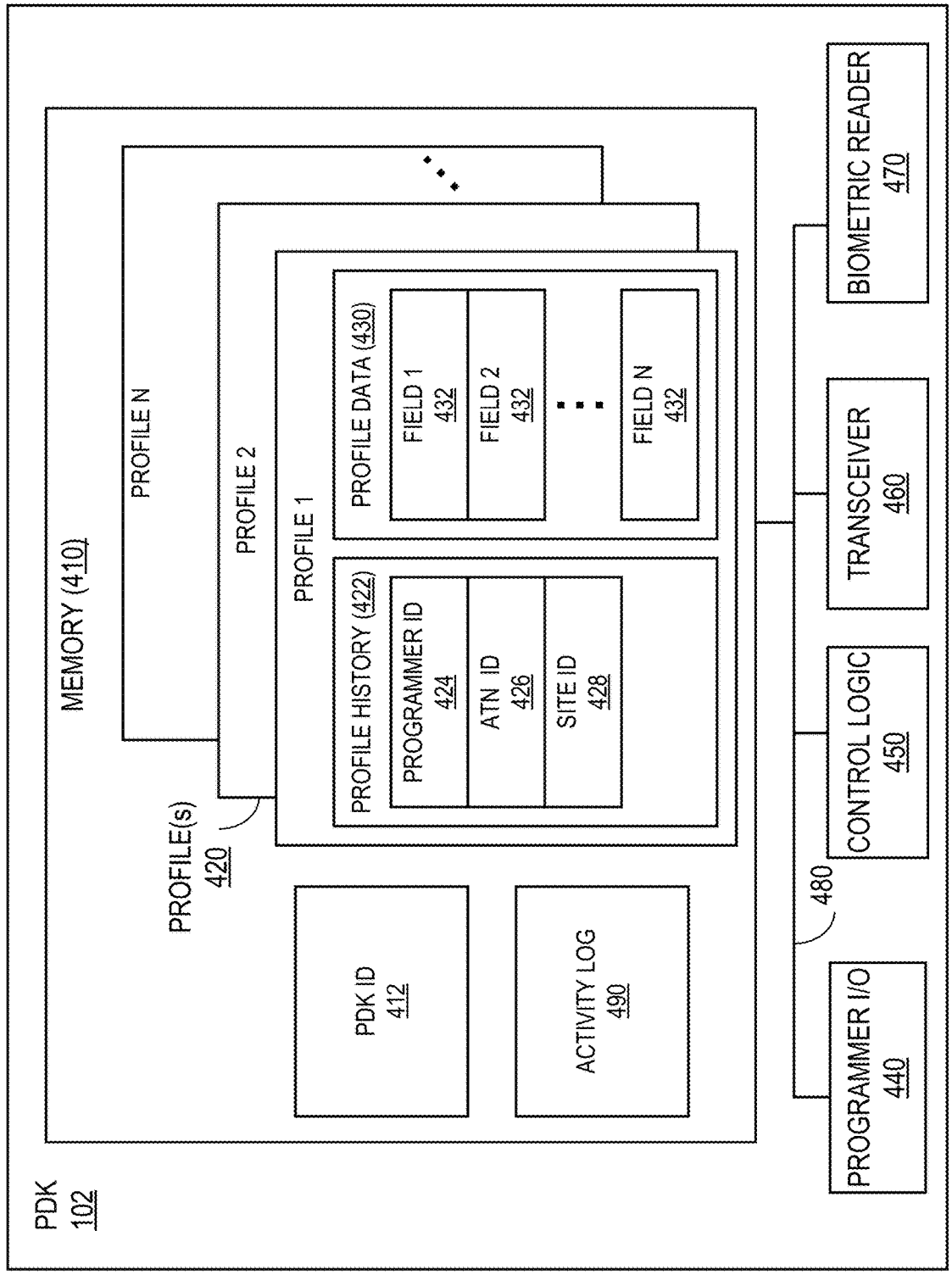
FIG. 4 is a block diagram illustrating one embodiment of a Personal Digital Key (PDK).

Turning now to FIG. 4, an example embodiment of a PDK 102 is illustrated. The PDK 102 comprises a memory 410, a programmer I/O 440, control logic 450, a transceiver 460 and a biometric reader 470 coupled by a bus 480. The PDK 102 can be standalone as a portable, physical device or can be integrated into commonly carried items. For example, a PDK 102 can be integrated into a portable electronic device such as a cell phone, Personal Digital Assistant (PDA), or GPS unit, an employee identification tag or badge, clothing, or jewelry items such as watches, rings, necklaces or bracelets. In one embodiment, the PDK 102 can be, for example, about the size of a Subscriber Identity Module (SIM) card and be as small as a square inch in area or less. In another embodiment, the PDK 102 can be easily contained in a pocket, on a keychain, or in a wallet. In yet another embodiment, a PDK 102 can be integrated into a sticker, tag or other item attachable to various items or equipment. In other embodiments, the PDK 102 can be integrated into a clipboard, patient wristband or other patient identification tags or badges. In some embodiments, where the PDK 102 is attached to equipment for tracking purposes, the PDK 102 also includes a button or switch that can be activated or deactivated to indicate whether the equipment is in use.

The memory 410 can be a read-only memory, a once-programmable memory, a read/write memory or any combination of memory types including physical access secured and tamperproof memories. The memory 410 typically stores a unique PDK ID 412, a activity log 490 and one or more profiles 420. The PDK ID 412 comprises a public section and a private section of information, each of which can be used for identification and authentication. In one embodiment, the PDK ID 412 is stored in a read-only format that cannot be changed subsequent to manufacture. The PDK ID 412 is used as an identifying feature of a PDK 102 and distinguishes between PDKs 102 in private 116 or Central 114 registry entries. In an alternative embodiment, the registries can identify a PDK 102 by a different ID than the PDK ID 412 stored in the PDK 102, or may use both the PDK ID 412 and the different ID in conjunction. The PDK ID 412 can also be used in basic PDK authentication to ensure that the PDK 102 is a valid device.

The activity log 490 stores information associated with various activities of the PDK. For example, if the PDK 102 is a patient's PDK, the activity log 490 stores information identifying the patient's location throughout various times. In one embodiment, the activity log 490 keeps track of each time the patient visits the healthcare facility. In another embodiment, the activity log 490 stores the patient's location throughout various points as the patient is in the provider's facility. Similarly, the if PDK 102 is attached to a piece of equipment or a cart of supplies, the activity log 490 stores location information as well. In another embodiment, if the PDK 102 is that of a provider, the activity log 490 stores information associated with the provider's rounds, i.e. each time a provider visits a certain patient or uses a particular medical device.

The profile fields 420 can be initially empty at the time of manufacture but can be written to by authorized individuals (e.g., a Notary) and/or hardware (e.g., a Programmer). In one embodiment, each profile 420 comprises a profile history 422 and profile data 430. Many different types of profiles 420 are possible. A biometric profile, for example, includes profile data 430 representing physical and/or behavioral information that can uniquely identify the PDK owner. A PDK 102 can store multiple biometric profiles, each comprising a different type of biometric information. In one embodiment, the biometric profile 420 comprises biometric information transformed by a mathematical operation, algorithm, or hash that represents the complete biometric information (e.g., a complete fingerprint scan). In one embodiment, a mathematical hash is a "one-way" operation such that there is no practical way to re-compute or recover the complete biometric information from the biometric profile. This both reduces the amount of data to be stored and adds an additional layer of protection to the user's personal biometric information. In one embodiment, the biometric profile is further encoded using an encoding key and/or algorithm that is stored with the biometric profile data. Then, for authentication, both the biometric profile data and the encoding key and/or algorithm are passed to the Reader 108.

In one embodiment the PDK 102 also stores one or more biometric profile "samples" associated with each biometric profile. The biometric profile sample is a subset of the complete profile that can be used for quick comparisons of biometric data. In one embodiment, the profile samples can be transmitted over a public communication channel or transmitted with reduced level of encryption while the full biometric profiles are only transmitted over secure channels. In the case of fingerprint authentication, for example, the biometric profile sample may represent only small portion area of the full fingerprint image. In another embodiment, the fingerprint profile sample is data that describes an arc of one or more lines of the fingerprint. In yet another embodiment, the fingerprint profile sample can be data representing color information of the fingerprint.

In another embodiment, the stored profiles 420 include a PIN profile that stores one or more PINs or passwords associated with the PDK owner. Here, the number or password stored in the PIN profile can be compared against an input provided by the user at the point of transaction to authenticate the user. In one embodiment, a PIN profile sample is also stored with the PIN profile that comprises a subset of the full PIN. For example, a PIN profile sample can be only the first two numbers of the PIN that can be used to quickly compare the stored PIN profile to a PIN obtained at the point of transaction.

In yet another embodiment, the PDK 102 stores a picture profile that includes one or more pictures of the PDK owner. In a picture profile authentication, the picture stored in the PDK 102 is transmitted to a display at the point of transaction to allow an administrator (e.g., a clerk or security guard) to confirm or reject the identity of the individual requesting the transaction. In another embodiment, an image is captured of the individual at the point of transaction and compared to the picture profile by an automated image analysis means. Furthermore, picture profiles could be used, for example, in place of conventional passports or drivers licenses to authenticate the identity of an individual and allow for remote identification of individuals. For example, a police officer following a vehicle could obtain an image and identity of the driver while still maintaining a safe distance from the vehicle. In the hospitality industry, a host could greet a guest at the door of a hotel, casino or restaurant and easily recognize the guest by obtaining the guest's picture profile as he/she enters. In healthcare, a doctor or nurse can ensure that he or she is administering the correct medication to the right patient by looking at the profile picture associated with that patient.

A registry or database profile typically stores information associating the user with a registry. The registry profile can be used to determine if the individual is associated with the controlling entity for that registry and if different types of transactions are authorized for the individual. A registry profile can further include additional user information for use with the registry. For example, a private registry profile associated with a particular merchant may include a credit card number that the user has selected as a default for that merchant. In one embodiment, a profile can further include spending limits that limits the amount of purchases a user can make with a particular vendor or using a particular profile.

A profile can further include personal identification information such as name, address, phone number, etc., insurance information, credit/debit card information, or information regarding visited providers. This information can be useful for certain types of transactions. For example, patient office visits, a PDK 102 can automatically transmit address, insurance and billing information to the Reader 108 at the conclusion of the office visit.

Generally, some types of profile information (e.g., a biometric profile) can only be acquired during a trusted initialization process that is administered by a trusted Notary. In one embodiment, other secure information such as medical conditions are also stored to the PDK 102 in the presence of a Notary. Alternatively, certain types of low-risk information can be added by the user without a Notary, such as, for example a change of address. In another embodiment, once an initial profile has been stored to the PDK 102, a user can add information to the PDK 102 using a Programmer without a Notary through self-authentication. For example, in one embodiment, a PDK 102 that has a stored biometric profile can be "unlocked" by providing a matching biometric input. Then, once unlocked, the user can add or remove additional profiles, insurance cards, personal information, etc. to the PDK 102 using a Programmer. For example, in one embodiment, a user that has unlocked his/her own PDK 102 can store additional biometric information (such as fingerprint information for other fingers) in his/her PDK 102. In another example, a user that cancels an insurance card, can unlock his/her PDK 102 to remove the insurance card information. In another embodiment, the user can make copies of the PDK 102 or move profiles from one PDK 102 to another once the PDK 102 is unlocked.

The profile history 422 includes a programmer ID field 424, a Notary ID 426, and a site ID field 428. The profile history 422 relates to the specific hardware, Notary, and site used at the time the profile data was created and stored to the PDK. Typically each profile 420 stores its specific profile history 422 along with the profile data 430. The profile history 422 can be recalled for auditing purposes at a later time to ensure the credibility of the stored data. In one embodiment, transaction history can also be stored to the PDK memory 410. Here, the PDK 102 stores information associated with any transactions made with the PDK 102 such as the healthcare provider, reason for office visit and insurance used, etc.

The PDK 102 also includes a programmer I/O 440 that provides an interface to a trusted Programmer (not shown). The Programmer comprises trusted hardware that is used to program the memory 410 of the PDK 102. An example embodiment of a Programmer is described in U.S. patent application Ser. No. 11/744,832 to John Giobbi, et al., entitled "Personal Digital Key Initialization and Registration For Secure Transaction" filed on May 5, 2007, the entire contents of which are incorporated herein by reference. The programmer I/O 440 can be, for example, a USB interface, serial interface, parallel interface, or any other direct or wireless link for transferring information between the PDK 102 and the Programmer. When coupled to the Programmer, the programmer I/O 440 receives initialization data, registration data or other information to be stored in the memory 410.

The control logic 450 coordinates between functions of the PDK 102. In one embodiment, the control logic 450 facilitates the flow of information between the programmer I/O 440, transceiver 460 and memory 410. The control logic 450 can further process data received from the memories 410, programmer I/O 440 and transceiver 460. Note that the control logic 450 is merely a grouping of control functions in a central architecture, and in other embodiments, the control functions can be distributed between the different modules of the PDK 102. The operation of the control logic will be understood to those skilled in the art based on the description below corresponding to FIGS. 8-11D.

The transceiver 460 is a wireless transmitter and receiver for wirelessly communicating with a Reader 108 or other wireless device. The transceiver 460 sends and receives data as modulated electromagnetic signals. Moreover, the data can be encrypted by the transceiver 460 and transmitted over a secure link. Further, the transceiver 460 can actively send connection requests, or can passively detect connection requests from another wireless source. In one embodiment, the transceiver 460 is used in place of a separate programmer I/O 440 and is used to wirelessly communicate with the Programmer for programming. In one embodiment, the transceiver 460 is adapted to communicate over a range of up to around 5 meters.

Optionally, the PDK 102 can also include a built in biometric reader 470 to acquire a biometric input from the user. The biometric reader 470 is configured to obtain a representation of physical or behavioral characteristics derived from the individual. The biometric input can be used to unlock the PDK 102 for profile updates, or for various types of authentication. For example, in one embodiment, a biometric input is received by the PDK 102 and compared to stored biometric information. Then, if the user is authenticated, the PDK 102 can indicate to the Reader 108 that the user is authenticated and transmit additional information (e.g., a credit card number) needed to complete a transaction.

Figure 5:
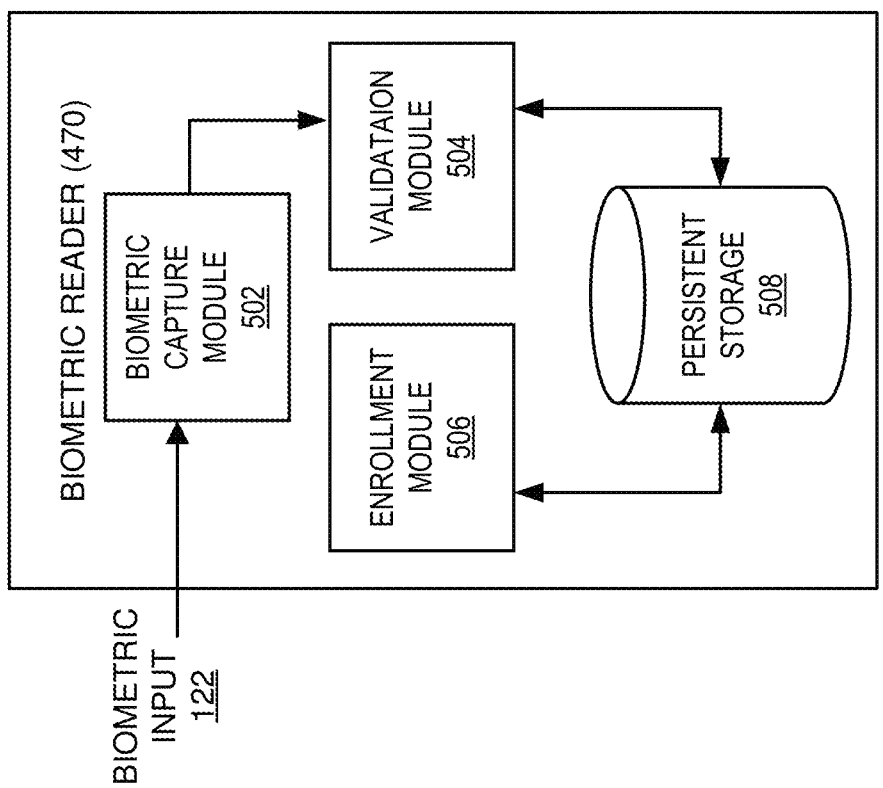
FIG. 5 is a block diagram illustrating one embodiment of a biometric reader of a PDK.

FIG. 5 is a block diagram illustrating one embodiment of a biometric reader 470 of a PDK 102. The biometric reader 470 includes a biometric capture module 502, a validation module 504, an enrollment module 506 and persistent storage 508. In one embodiment, the enrollment module 506 registers a user with a PDK 102 by persistently storing biometric data associated with the user. Further, enrollment module 506 registers PDK 102 with a trusted authority by providing the code (e.g., device ID) to the trusted authority.

Or conversely, the trusted authority can provide the code to PDK 102 to be stored therein.

The biometric capture module 502 comprises a scan pad to capture scan data from a user's fingerprint (e.g., a digital or analog representation of the fingerprint). Other embodiments of the biometric capture module 502 includes retinal scanners, iris scanners, facial scanner, palm scanners, DNA/RNA analyzers, signature analyzers, cameras, microphones, and voice analyzers to capture other identifying biometric data. Using the biometric data, validation module 504 determines whether the user's fingerprint, or other biometric data, matches the stored biometric data from enrollment. Conventional techniques for comparing fingerprints can be used. For example, the unique pattern of ridges and valleys of the fingerprints can be compared. A statistical model can be used to determine comparison results. Validation module 504 can send comparison results to control logic 450 of the PDK 102.

In other embodiments, validation module 504 can be configured to capture biometric data for other human characteristics. For example, a digital image of a retina, iris, and/or handwriting sample can be captured. In another example, a microphone can capture a voice sample.

Persistent storage 508 persistently stores biometric data from one or more users which can be provided according to specific implementations. In one embodiment, at least some of persistent storage 508 is a memory element that can be written to once but cannot subsequently be altered. Persistent storage 508 can include, for example, a ROM element, a flash memory element, or any other type of non-volatile storage element. Persistent storage 508 is itself, and stores data in, a tamper-proof format to prevent any changes to the stored data. Tamper-proofing increases reliability of authentication because it does not allow any changes to biometric data (i.e., allows reads of stored data, but not writes to store new data or modify existing data). Furthermore, data can be stored in an encrypted form.

In one embodiment, persistent storage 508 also stores the code that is provided by the PDK 102 responsive to successful verification of the user. Further, in some embodiments persistent storage 508 stores other data utilized during the operation of PDK 102. For example, persistent storage 508 can store encryption/decryption keys utilized to establish secure communications links.

An example embodiment of PDK with a biometric reader is described in U.S. patent application Ser. No. 11/314,199 to John Giobbi, et al., entitled "Biometric Personal Data Key (PDK) Authentication", the entire contents of which are incorporated herein by reference.

Figure 6:
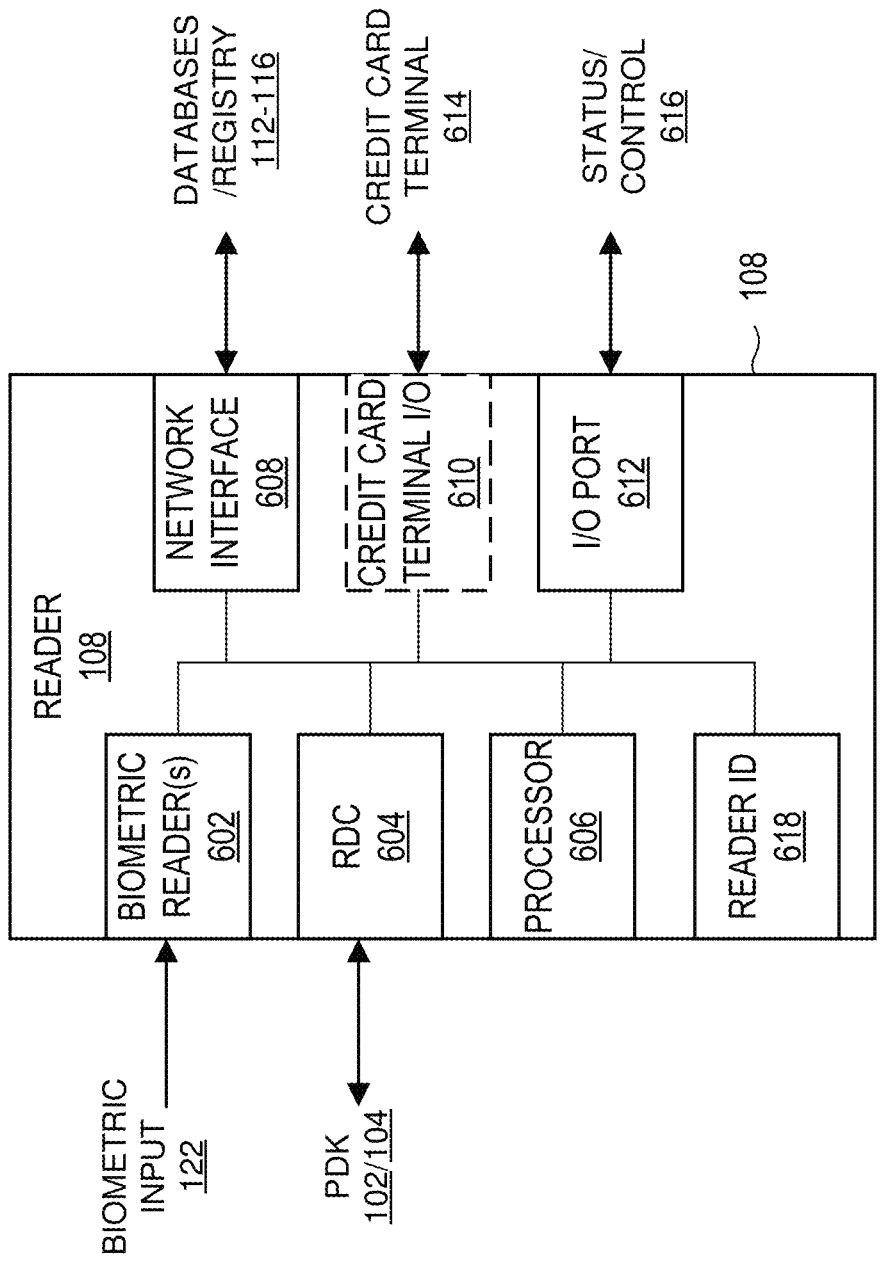
FIG. 6 is a block diagram illustrating one embodiment of a reader.

Turning now to FIG. 6, an example embodiment of a Reader 108 is illustrated. The embodiment includes one or more biometric readers 602, a receiver-decoder circuit (RDC) 604, a processor 606, a network interface 608, an I/O port 612, optionally a credit card terminal I/O 610 and a reader ID 618. In alternative embodiments, different or additional modules can be included in the Reader 108.

The RDC 604 provides the wireless interface to the PDK 102. Generally, the RDC 604 wirelessly receives data from the PDKs 102 in an encrypted format and decodes the encrypted data for processing by the processor 306. An example embodiment of an RDC is described in U.S. patent application Ser. No. 11/292,330 entitled "Personal Digital Key And Receiver/Decoder Circuit System And Method", the entire contents of which are incorporated herein by reference. Encrypting data transmitted between the PDK 102 and Reader 108 minimizes the possibility of eavesdropping or other fraudulent activity. In one embodiment, the RDC 604 is also configured to transmit and receive certain types of information in an unencrypted or public format.

The biometric reader 602 receives and processes the biometric input 122 from an individual and is configured to obtain a representation of physical or behavioral characteristics derived from the individual. In one embodiment, the biometric reader 602 is a fingerprint scanner. Here, the biometric reader 602 includes an image capture device adapted to capture the unique pattern of ridges and valleys in a fingerprint also known as minutiae. Other embodiments of biometric readers 602 include retinal scanners, iris scanners, facial scanner, palm scanners, DNA/RNA analyzers, signature analyzers, cameras, microphones, and voice analyzers. Furthermore, the Reader 108 can include multiple biometric readers 602 of different types. In one embodiment, the biometric reader 602 automatically computes mathematical representations or hashes of the scanned data that can be compared to the mathematically processed biometric profile information stored in the PDK 102.

The processor 606 can be any general-purpose processor for implementing a number of processing tasks. Generally, the processor 606 processes data received by the Reader 108 or data to be transmitted by the Reader 108. For example, a biometric input 122 received by the biometric reader 602 can be processed and compared to the biometric profile 420 received from the PDK 102 in order to determine if a transaction should be authorized. In different embodiments, processing tasks can be performed within each individual module or can be distributed between local processors and a central processor. The processor 606 further includes a working memory for use in various processes such as performing the method of FIGS. 8-11D.

The network interface 608 is a wired or wireless communication link between the Reader 108 and one or more external databases such as, for example, a validation database 112, the Central Registry 114 or a private registry 116_a_, 116_b_. For example, in one type of authentication, information is received from the PDK 102 at the RDC 604, processed by the processor 606, and transmitted to an external database 112-116 through the network interface 608. The network interface 608 can also receive data sent through the network 110 for local processing by the Reader 108. In one embodiment, the network interface 608 provides a connection to a remote system administrator to configure the Reader 108 according to various control settings.

The I/O port 612 provides a general input and output interface to the Reader 108. The I/O port 612 may be coupled to any variety of input devices to receive inputs such as a numerical or alphabetic input from a keypad, control settings, menu selections, confirmations, and so on. Outputs can include, for example, status LEDs, an LCD, or other display that provides instructions, menus or control options to a user.

The credit card terminal I/O 610 optionally provides an interface to an existing credit card terminal 614. In embodiments including the credit card terminal I/O 610, the Reader 108 supplements existing hardware and acts in conjunction with a conventional credit card terminal 614. In an alternative embodiment, the functions of an external credit card terminal 614 are instead built into the Reader 108. Here, a Reader 108 can completely replace an existing credit card terminal 614.

In one embodiment, a Reader 108 is adapted to detect and prevent fraudulent use of PDKs that are lost, stolen, revoked, expired or otherwise invalid. For example, the Reader 108 can download lists of invalid PDKs IDs 412 from a remote database and block these PDKs 102 from use with the Reader 108. Furthermore, in one embodiment, the Reader 108 can update the blocked list and/or send updates to remote registries 114,116*a*, 116*b* or remote Readers 108 upon detecting a fraudulently used PDK 102. For example, if a biometric input 122 is received by the Reader 108 that does not match the biometric profile received from the PDK 102, the Reader 108 can obtain the PDK ID 412 and add it to a list of blocked PDK IDs 412. In another embodiment, upon detecting fraudulent use, the Reader 108 can send a signal to the PDK 102 that instructs the PDK 102 to deactivate itself. The deactivation period can be, for example, a fixed period of time, or until the rightful owner requests re-activation of the PDK 102. In yet another embodiment, the Reader 108 can send a signal instructing the fraudulently obtained PDK 102 to send alarm signals indicating that the PDK 102 a stolen device. Here, a stolen PDK 102 can be tracked, located and recovered by monitoring the alarm signals. In one embodiment, the Reader 108 stores biometric or other identifying information from an individual that attempts to fraudulently use a PDK 102 so that the individual's identity can be determined.

The reader ID 618 is memory that stores the reader's unique identification number. The memory can be a read-only memory, a once-programmable memory, a read/write memory or any combination of memory types including physical access secured and tamperproof memories. The reader ID 618 plays an integral role in the process for tracking equipment, supplies and individuals as will be explained in more detail below.

Generally, the Reader 108 is configured to implement at least one type of authentication prior to enabling a transaction. In many cases, multiple layers of authentication are used. A first layer of authentication, referred to herein as "device authentication," begins any time a PDK 102 moves within range of a Reader 108. In device authentication, the Reader 108 and the PDK 102 each ensure that the other is valid based on the device characteristics, independent of any profiles stored in the PDK 102. In some configurations, when fast and simple authentication is desirable, only device authentication is required to initiate the transaction. For example, a Reader 108 may be configured to use only device authentication for office visit check-ins. The configuration is also useful in other types of low risk transactions where speed is preferred over additional layers of authentication.

Other configurations of the Reader 108 require one or more additional layers of authentication, referred to herein as "profile authentication" based on one or more profiles stored in the PDK 102. Profile authentication can include, for example, a biometric authentication, a PIN authentication, a photo authentication, a registry authentication, etc. or any combination of the above authentication types. Profile authentications are useful when a more exhaustive authentication process is desired, for example, for invasive patient treatments or drug administration.

Figure 7:
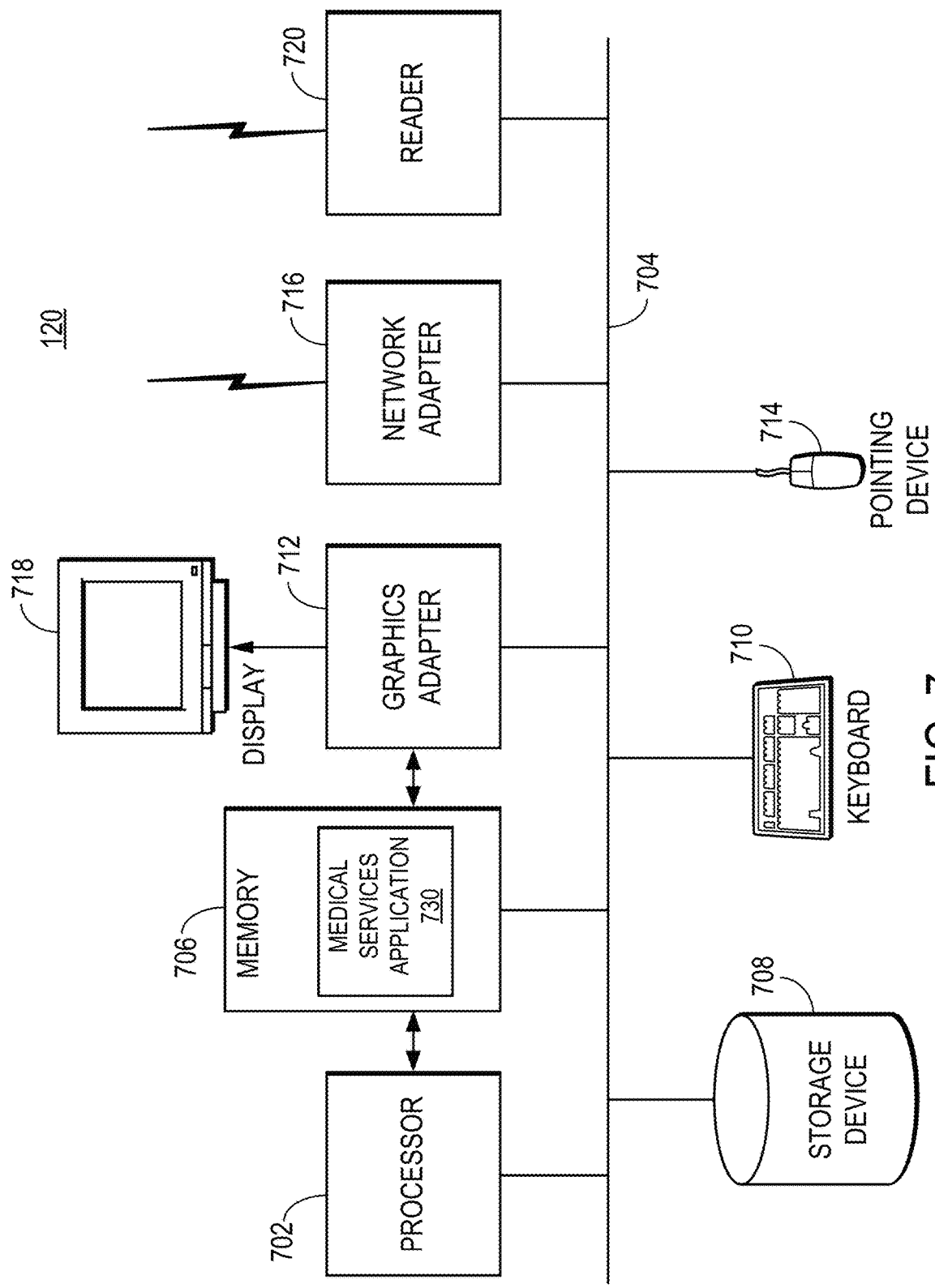
FIG. 7 is a block diagram illustrating one embodiment of a provider interface device.

FIG. 7 is a high-level block diagram of one embodiment of a provider interface device 120. In one embodiment, the provider interface device 120 is a personal computer. In another embodiment, the provider interface device 120 is a smart phone or other mobile computing and communication device. Illustrated are at least one processor 702 coupled to a bus 704. Also coupled to the bus 704 are a memory 706, a storage device 708, a keyboard 710, a graphics adapter 712, a pointing device 714, a network adapter 716 and a reader 720. In one embodiment, the functionality of the bus 704 is provided by an interconnecting chipset. A display 718 is coupled to the graphics adapter 712.

The memory 706 includes a medical services application 730. In one embodiment, the medical services application 730 enables the provider interface device 120 to communicate with the local services 124 and third party link module 126. In another embodiment, the medical services application 730 processes information and data received from the readers 720 and various modules and servers of the local services 124 and third party link module 126.

The storage device 708 is any device capable of holding data, like a hard drive, compact disk read-only memory (CD-ROM), DVD, or a solid-state memory device. The memory 706 holds instructions and data used by the processor 702. The pointing device 714 may be a mouse, track ball, or other type of pointing device, and is used in combination with the keyboard 710 to input data into the provider interface device 120. The graphics adapter 712 displays images and other information on the display 718. The network adapter 716 couples the provider interface device 120 to a local or wide area network.

As is known in the art, a provider interface device 120 can have different and/or other components than those shown in FIG. 7. In addition, the provider interface device 120 can lack certain illustrated components. In one embodiment, a provider interface device 120 lacks a keyboard 710, pointing device 714, graphics adapter 712, and/or display 718. Moreover, the storage device 708 can be local and/or remote from provider interface device 120 (such as embodied within a storage area network (SAN)). The reader 720 includes all or some of the same components as the Reader 108 as shown in FIG. 6.

As is known in the art, the provider interface device 120 is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device 708, loaded into the memory 706, and executed by the processor 702.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

Figure 8:
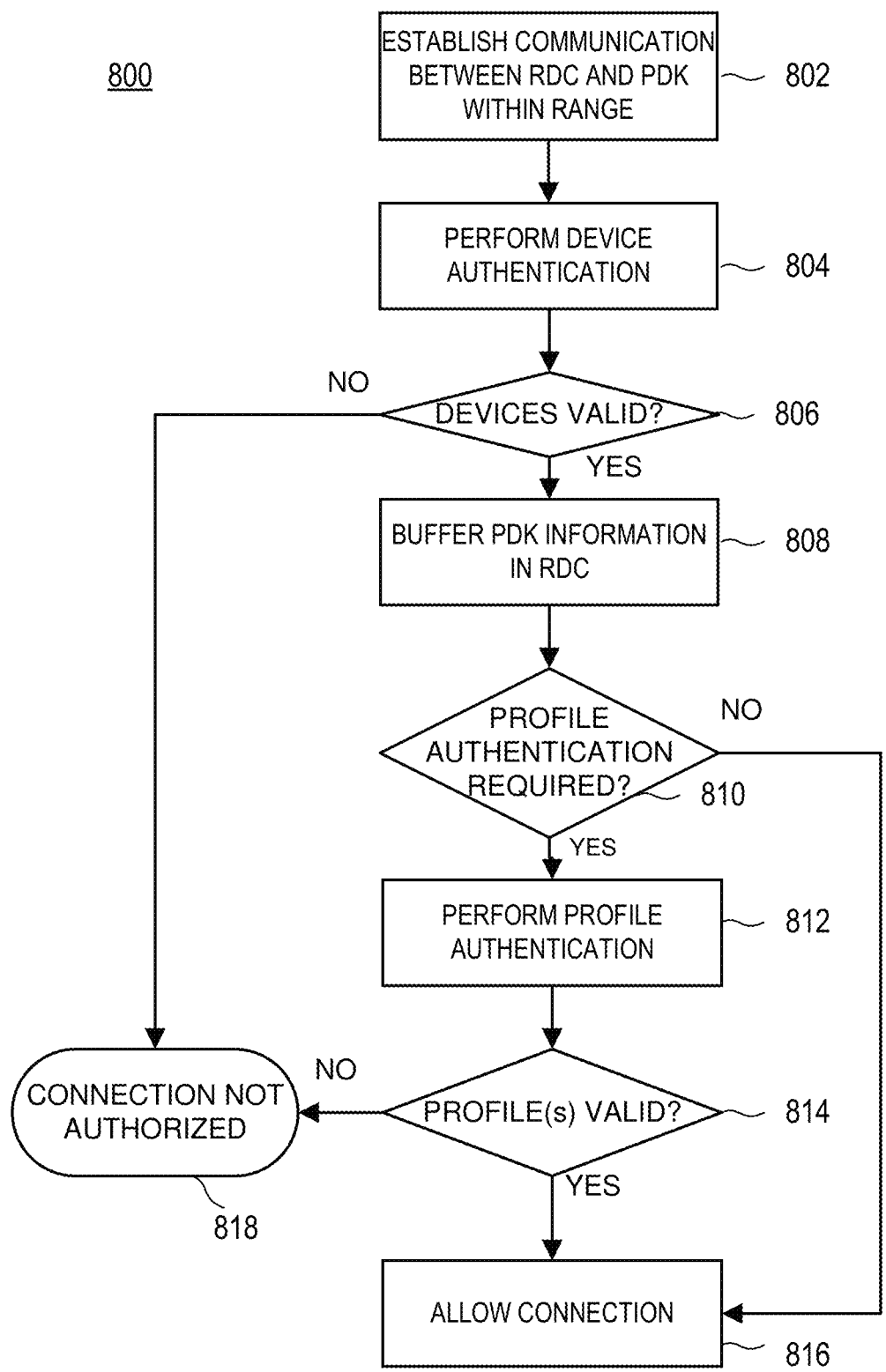
FIG. 8 is a flowchart illustrating one embodiment of a process for authorizing a communication connection using secure authentication.

FIG. 8 is a flowchart illustrating one embodiment of a process for authorizing a communication connection using secure authentication. When a PDK 102 comes within range of a Reader 108, communication is automatically established 802 between the RDC 604 of the Reader 108 and the PDK 102. It should be noted that the processes described herein with regards to Reader 108 may be also performed with reader 720 of the provider interface device 120.

In one embodiment, the RDC 604 continually transmits beacons that are detected by the PDK 102 when it enters a proximity zone of the Reader 108. In an alternative embodiment, the communication is instead initiated by the PDK 102 and acknowledged by the Reader 108. Generally, initial communication between the Reader 108 and the PDK 102 is not encrypted in order to provide faster and more power efficient communication.

In step 804, a device authentication is performed. Here, the Reader 108 establishes if the PDK 102 is a valid device and PDK 102 establishes if the Reader 108 is valid. Furthermore, device authentication determines if the PDK 102 is capable of providing the type of authentication required by the Reader 108.

Figure 9:
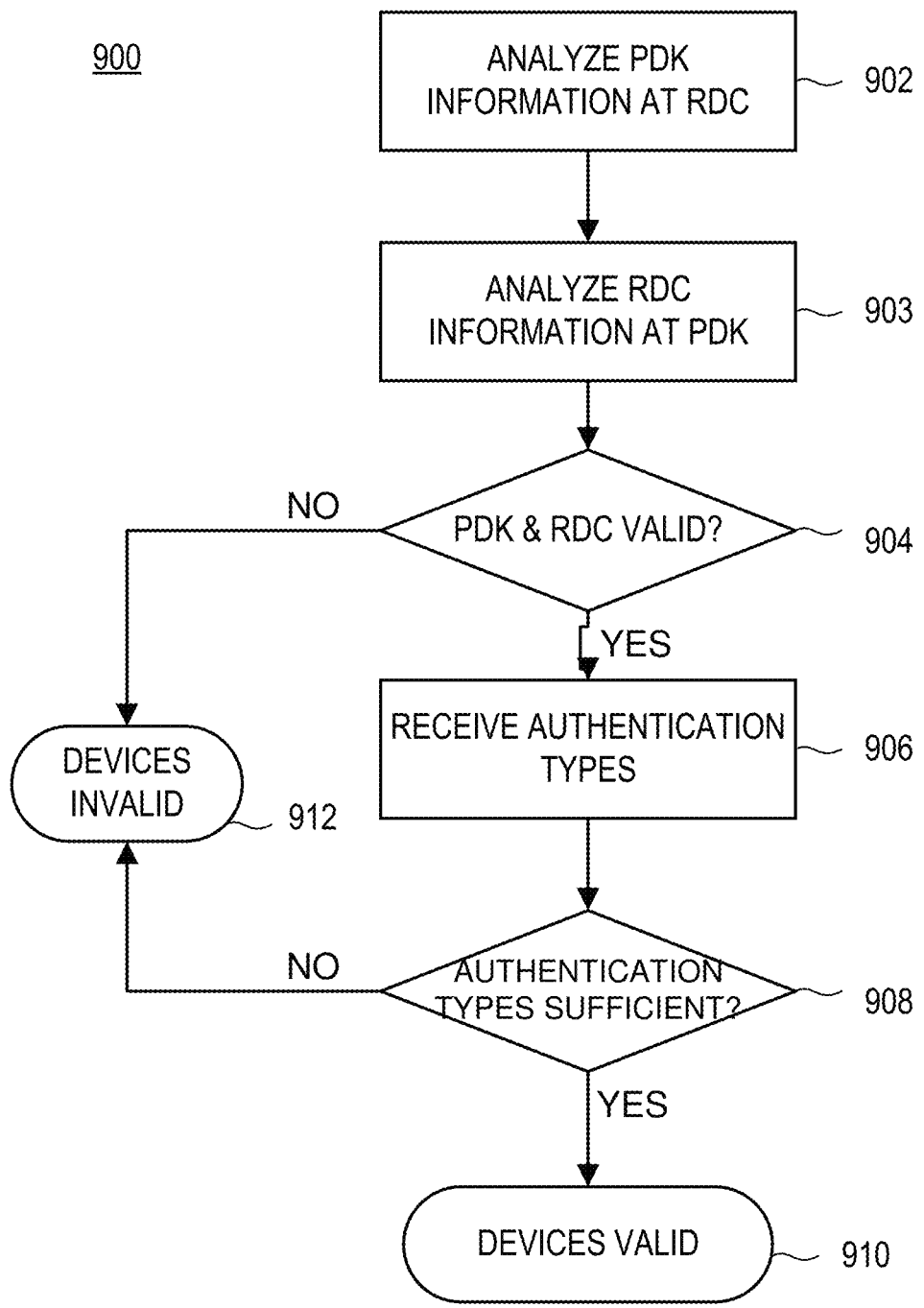
FIG. 9 is a flowchart illustrating one embodiment of a process for device authentication by a reader.

An example embodiment of a method for performing 804 device authentication is illustrated in FIG. 9. The RDC 604 receives and analyzes 902 information from the PDK 102; and the PDK 102 receives and analyzes 902 information received from the RDC 604. Generally, this initial information is transmitted over a public communication channel in an unencrypted format. Based on the received information, each device 102, 604 determines 904 if the other is valid. As will be apparent to one of ordinary skill in the art, a number of different protocols can be used for this type of authentication such as, for example, a challenge-response authentication or a challenge handshake authentication protocol (CHAP). If either of the devices 102, 604 is invalid 912, the process ends. If both the PDK 102 and the RDC 604 are determined by the other to be valid, the Reader 108 requests and receives 906 authentication type information from the PDK 102 indicating the different types of authentication the PDK 102 is capable of satisfying based on the types of profiles the PDK 102 stores. The available profile types in the PDK 102 are compared against the authentication types that can be used by the Reader 108. For example, a particular Reader 108 may be configured to perform only a fingerprint authentication and therefore any PDK without a fingerprint biometric profile cannot be used with the Reader 108. In one embodiment, the Reader 108 can allow more than one type of profile to be used. In another embodiment, the Reader 108 requires more than one type of profile for authentication, while in yet further embodiments no profile authentications are required. Next, the method determines 908 whether the PDK 102 has one or more profiles sufficient for authentication. If the PDK 102 does not have one or more profiles sufficient for authentication with the Reader 108, the devices 102, 604 are determined to be invalid 912 because they cannot be used with each other. If the PDK 102 does have one or more sufficient types of profiles, the devices are valid 910.

Turning back to FIG. 8, if either the PDK 102 or RDC 604 is not found valid during device authentication 804, the connection is not authorized 818 and the process ends. If the devices are valid, the RDC 604 temporarily buffers 808 the received PDK information. It is noted that in one embodiment, steps 802-808 are automatically initiated each time a PDK 102 enters the proximity zone of the Reader 108. Thus, if multiple PDKs 102 enter the proximity zone, the Reader 108 automatically determines which PDKs 102 are valid and buffers the received information from each valid PDK 102.

The method next determines 810 whether profile authentication is required based on the configuration of the Reader 108, the type of transaction desired or by request of a merchant or other administrator. If the Reader 108 configuration does not require a profile authentication in addition to the PDK authentication, then the Reader 108 proceeds to complete the transaction for the PDK 102. If the Reader 108 does require profile authentication, the profile authentication is performed 812 as will be described below with references to FIGS. 10-11D. If a required profile is determined 814 to be valid, the Reader 108 allows 816 the connection. Otherwise, the Reader 108 indicates that the connection is not authorized 818. In one embodiment, allowing 816 the connection includes enabling access to secure patient records. In another embodiment, allowing 816 the connection includes enabling the automatic logging in and out of software and system applications. Patient or provider name or medical record number (typically stored in a profile memory field 432) can be transmitted by the PDK 102 for identification purposes. In one embodiment, the PDK 102 is configured with multiple purchasing means and a default is configured for different types of transactions. In another embodiment, each insurance card or medical billing information is displayed to the customer by the Reader 108 and the customer is allowed to select which to apply to the office visit.

Figure 10:
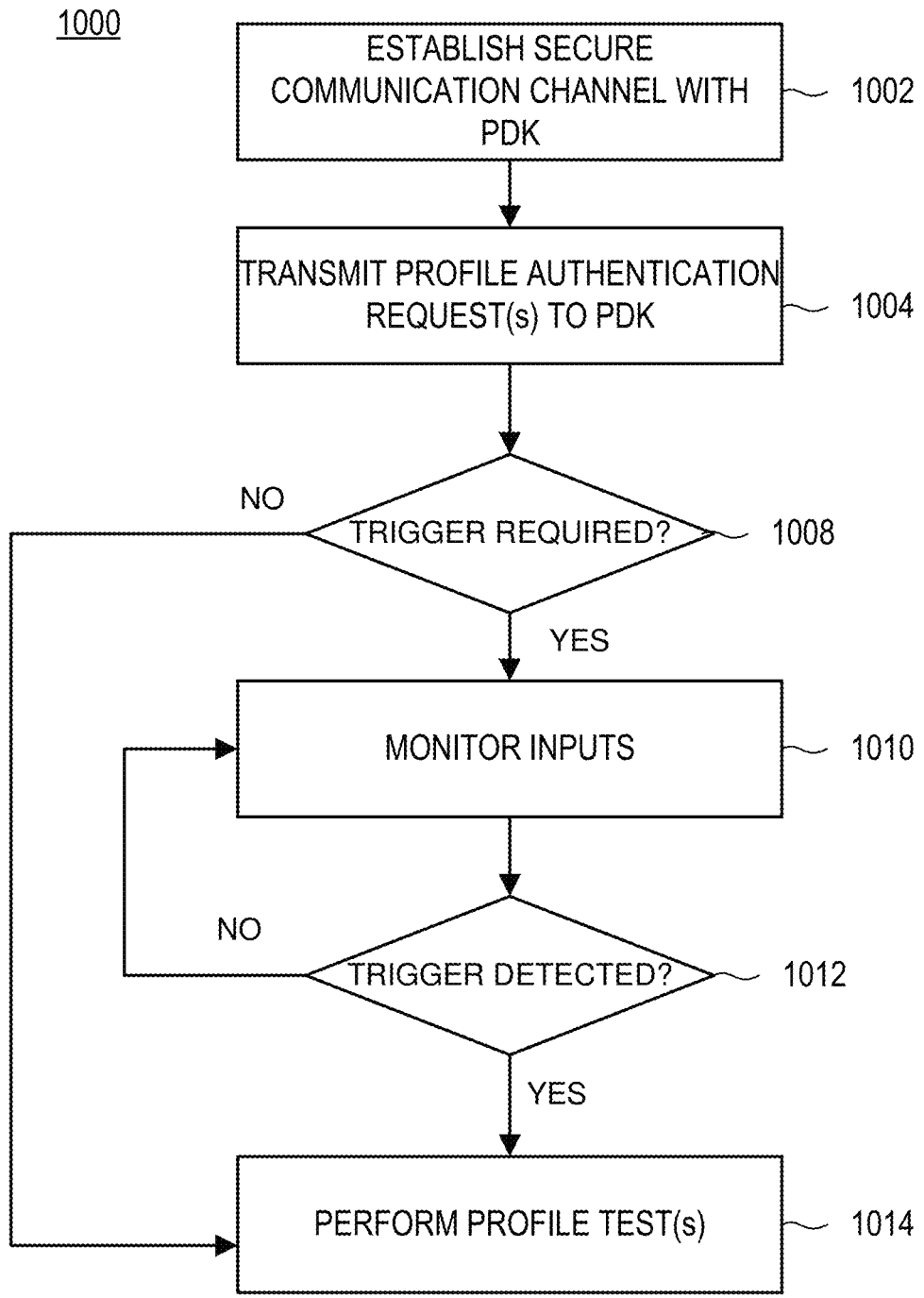
FIG. 10 is a flowchart illustrating one embodiment of a process for profile authentication by a reader.

Turning now to FIG. 10, an embodiment of a process for profile authentication is illustrated. In step 1002, a secure communication channel is established between the RDC 604 and the PDK 102. Information sent and received over the secure channel is in an encrypted format that cannot be practically decoded, retransmitted, reused, or replayed to achieve valid responses by an eavesdropping device. The Reader 108 transmits 1004 profile authentication requests to the PDK 102 requesting transmission of one or more stored profiles over the secure channel. At 1008, the process determines whether a "trigger" is required for authentication. The requirement for a trigger depends on the configuration of the Reader 108, the specific type of transaction to be executed and the type of authentication requested.

In a first configuration, a trigger is required to continue the process because of the type of authentication being used. For example, in biometric authentication, the authentication process cannot continue until the Reader detects a biometric contact and receives biometric information. It is noted that biometric contact is not limited to physical contact and can be, for example, the touch of a finger to a fingerprint scanner, the positioning of a face in front of a facial or retinal scanner, the receipt of a signature, the detection of a voice, the receipt of a DNA sample, RNA sample, or derivatives or any other action that permits the Reader 108 to begin acquiring the biometric input 122. By supplying the biometric contact, the user indicates that the authentication and transaction process should proceed. For example, a PDK holder that wants log in to the healthcare software application system via the provider interface device 120 initiates the logon process by touching a finger to the reader 720 of the provider interface device 120. The provider interface device 120 then displays confirmation of the user's login.

In a second configuration, some other user action is required as a trigger to proceed with the transaction even if the authentication process itself doesn't necessarily require any input. This can be used for many purchasing transactions to ensure that the purchase is not executed until intent to purchase is clear. For example, a Reader 108 at a gas station can be configured to trigger the transaction when a customer begins dispensing gas. At a supermarket, a Reader 108 can be configured to trigger the transaction when items are scanned at a checkout counter. Similarly, a user may log in to healthcare software application system via the provider interface device 120 by simply being in the proximity zone of the reader 720 of a provider interface device 120 and beginning to use the keyboard 710 or pointing device 714 of the provider interface device 120.

In a third configuration, no trigger is used and the Reader 108 automatically completes the remaining authentication/transaction with no explicit action by the user. This configuration is appropriate in situations where the mere presence of a PDK 102 within range of the Reader 108 is by itself a clear indication of the person associated with the PDK 102 desires to complete a transaction. For example, a Reader 108 can be positioned inside the entrance to a doctor's office or clinic. When a patient having an associated PDK walks through the entrance, the Reader 108 detects the PDK 102 within range, authenticates the user, and notifies the receptionist that the patient has arrived for his or her appointment. Thus, if no trigger is required, the process next performs 1014 the requested profile authentication tests.

If a trigger is required, the Reader 108 monitors 1010 its inputs (e.g., a biometric reader, key pad, etc.) and checks for the detection 1012 of a trigger. If the required trigger is detected, the process continues to perform 1014 one or more profile authentication test. FIGS. 11A-11D illustrate various embodiments of profile authentication tests. According to different configurations of the Reader 108, one or more of the illustrated authentication processes may be used. Further, in some embodiments, one or more of the processes may be repeated (e.g., for different types of biometric inputs).

Figures 11A, 11B:
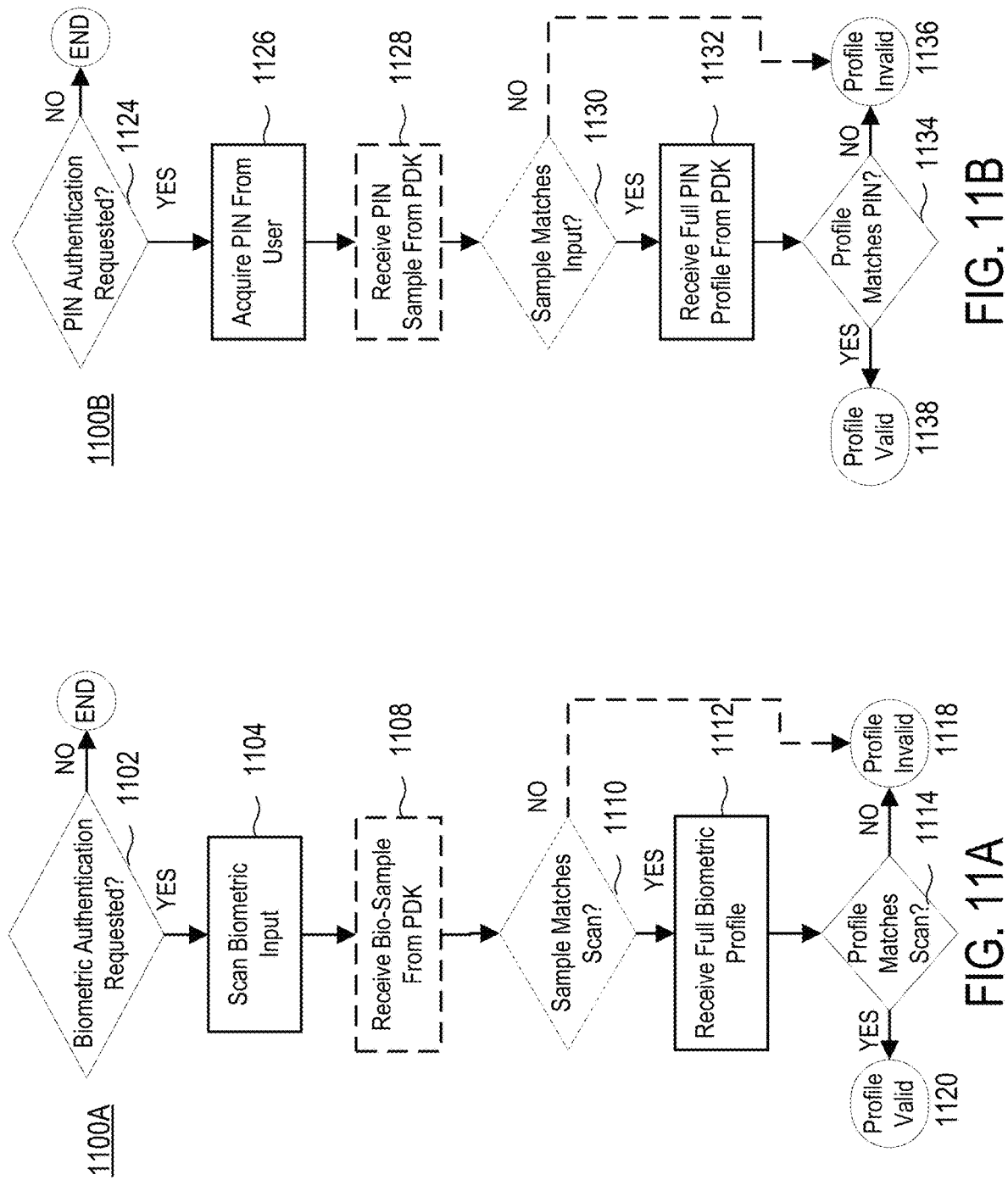
FIG. 11A is a flowchart illustrating one embodiment of a process for profile testing using a biometric input.
FIG. 11B is a flowchart illustrating one embodiment of a process for profile testing using a personal identification number.

Referring first to FIG. 11A, it illustrates a process for biometric authentication. In biometric authentication, a Reader 108 compares a biometric profile stored in the PDK 102 to the biometric input 122 acquired by the biometric reader 602. Advantageously, the biometric input 122 is not persistently stored by the Reader 108, reducing the risk of theft or fraudulent use. If 1102 biometric authentication is requested, the Reader 108 scans 1104 the biometric input 122 supplied by the user. In one embodiment, scanning 1104 includes computing a mathematical representation or hash of the biometric input 122 that can be directly compared to the biometric profile.

Furthermore, in one embodiment, scanning 1104 also includes obtaining a biometric input sample from the biometric input according to the same function used to compute the biometric profile sample stored in the PDK 102. Optionally, the Reader 108 receives 1108 a biometric profile sample from the PDK 102 and determines 1110 if the biometric profile sample matches the biometric input sample. If the biometric profile sample does not match the input sample computed from the scan, the profile is determined to be invalid 1118. If the biometric profile sample matches, the full biometric profile 1112 is received from the PDK 102 to determine 1114 if the full biometric profile 1112 matches the complete biometric input 122. If the profile 1112 matches the scan, the profile 1112 is determined to be valid 1120, otherwise the profile 1112 is invalid 1118. It is noted that in one embodiment, steps 1108 and 1110 are skipped and only a full comparison is performed. In one embodiment, the biometric profile and/or biometric profile sample is encoded and transmitted to the Reader 108 along with an encoding key and/or algorithm. Then, the Reader 108 uses the encoding key and/or algorithm to recover the biometric profile and/or biometric profile sample. In another alternative embodiment, only the encoding key and/or algorithm is transmitted by the PDK 102 and the biometric profile data is recovered from a remote database in an encoded form that can then be decoded using the key and/or algorithm.

It will be apparent to one of ordinary skill that in alternative embodiments, some of the steps in the biometric profile authentication process can be performed by the PDK 102 instead of the Reader 108 or by an external system coupled to the Reader 108. For example, in one embodiment, the biometric input 122 can be scanned 1104 using a biometric reader built into the PDK 102. Furthermore, in one embodiment, the steps of computing the mathematical representation or hash of the biometric input and/or the steps of comparing the biometric input to the biometric profile can be performed by the PDK 102, by the Reader 108, by an external system coupled to the Reader 108, or by any combination of the devices. In one embodiment, at least some of the information is transmitted back and forth between the PDK 102 and the Reader 108 throughout the authentication process. For example, the biometric input 122 can be acquired by the PDK 102, and transmitted to the Reader 108, altered by the Reader 108, and sent back to the PDK 102 for comparison. Other variations of information exchange and processing are possible without departing from the scope of the invention. The transfer of data between the PDK 102 and the Reader 108 and/or sharing of processing can provide can further contribute to ensuring the legitimacy of each device.

FIG. 11B illustrates a process for PIN authentication. If PIN authentication is requested 1124, a PIN is acquired 1126 from the user through a keypad, mouse, touch screen or other input mechanism. Optionally, the Reader 108 receives 1128 a PIN sample from the PDK 102 comprising a subset of data from the full PIN. For example, the PIN sample can comprise the first and last digits of the PIN. If the Reader 108 determines 1130 that the PIN sample does not match the input, the profile is immediately determined to be invalid 1136. If the PIN sample matches, the full PIN profile is received 1132 from the PDK and compared to the input. If the Reader 108 determines 1134 that the profile matches the input, the profile is determined to be valid and is otherwise invalid 1136. It is noted that in one embodiment, steps 1128 and 1130 are skipped.

Figure 11D:
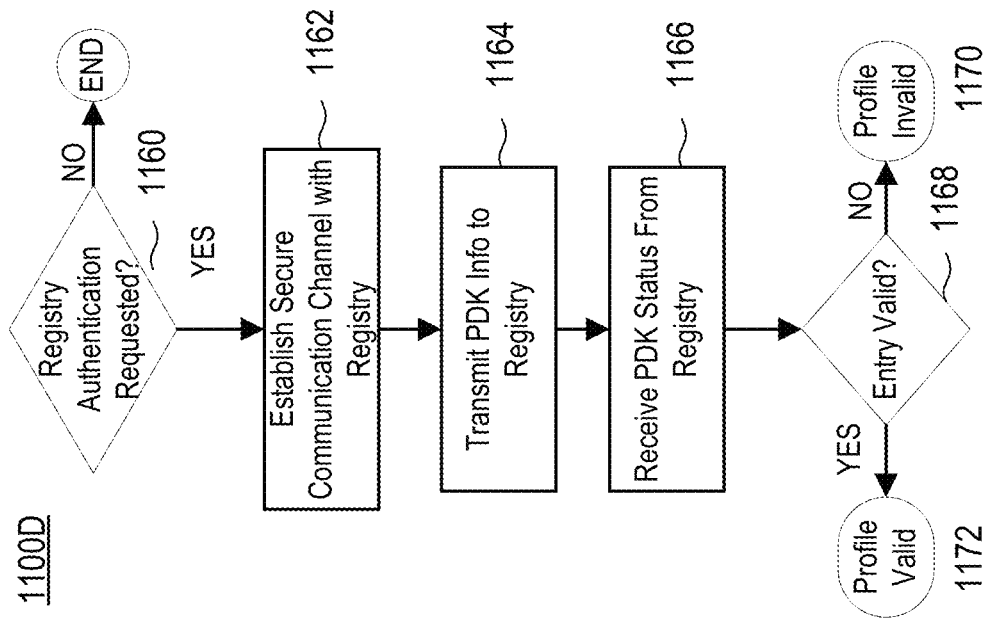
FIG. 11D is a flowchart illustrating one embodiment of a process for profile testing using a private or central registry.
Figure 11C:
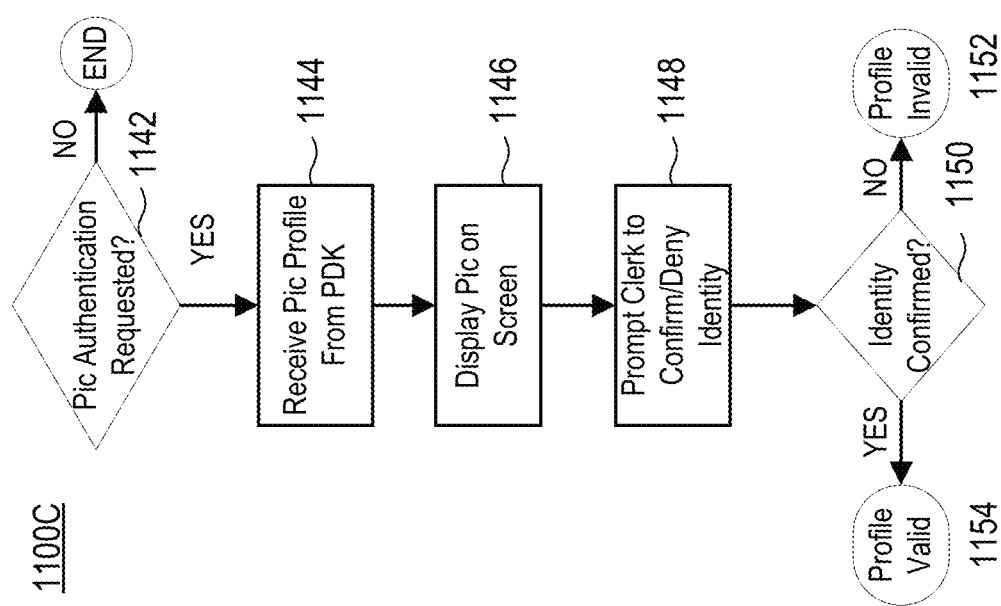
FIG. 11C is a flowchart illustrating one embodiment of a process for profile testing using a picture profile.

FIG. 11C illustrates a process for a picture authentication. If the Reader 108 determines 1124 that picture authentication is requested, a picture profile is received 1144 from the PDK 102 by the Reader 108 and displayed 1146 on a screen. An administrator (e.g., a clerk, security guard, etc.) is prompted 1148 to compare the displayed picture to the individual and confirms or denies if the identities match. If the administrator confirms that the identities match, the picture profile is determined to be valid 1164 and is otherwise invalid 1152. In an alternative embodiment, the process is automated and the administrator input is replaced with a process similar to that described above with reference to FIG. 11A. Here, an image of the user is captured and face recognition is performed by comparing picture profile information received from the PDK 102 to the captured image.

FIG. 11D illustrates a process for authentication with a private registry 116a, 116b or the Central Registry 114. If the Reader 108 determines that registry authentication is requested, a secure communication channel is established 1162 over the network 110 between the Reader 108 and one or more registries (e.g., the Central Registry 114, any private registry 116a, 116b, or other validation database 112). If any additional information is needed to process the registry authentication (e.g., an insurance policy number), the Reader 108 requests and receives the additional information from the PDK 102. Identification information is transmitted 1164 from the Reader 108 to the registry 114, 116a, 116b through the network interface 608. The PDK status is received 1166 from the registry to determine 1168 if the status is valid 1172 or invalid 1170. In one embodiment, the information is processed remotely at the registry 114, 116a, 116b and the registry 114, 116a, 116b returns a validation decision to the Reader 108. In another embodiment, the Reader 108 queries the private 116a, 116b or Central registry 114 for information that is returned to the Reader 108. The information is then analyzed by the Reader 108 and the authorization decision is made locally. In one embodiment, the process involves transmitting credit card (or other purchasing information) to a validation database 112 to authorize the purchase and receive the status of the card. Status information may include, for example, confirmation that the card is active and not reported lost or stolen and that sufficient funds are present to execute the purchase.

Figure 12:
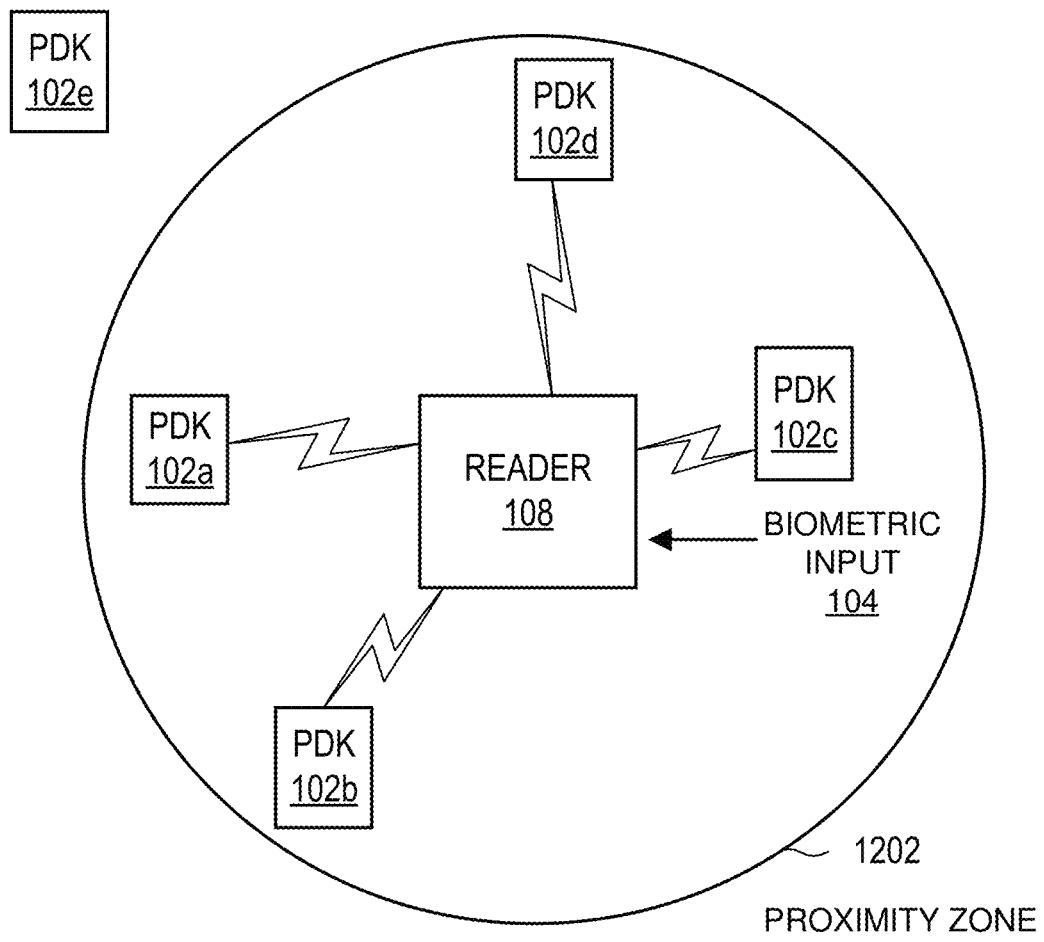
FIG. 12 illustrates an example scenario of a reader operating in a congested area with multiple PDKs within its proximity zone.

Turning now to FIG. 12 a scenario is illustrated where multiple PDKs 102a-e are present near a Reader 108. This scenario is common when a Reader 108 is located in a high occupancy area such as, for example, a hospital lobby or waiting area. Here, the Reader 108 can communicate with PDKs 102*a-d* within the proximity zone 1202 and does not communicate with PDKs 102*e-f* outside the proximity zone 1202. In one embodiment, the Reader 108 receives the unique PDK ID from a PDK 102 when it enters the proximity zone 1202 and records its time of arrival. In one embodiment, the Reader 108 further initiates a device authentication of the PDK 102 after a predefined period of time (e.g., 5 seconds) that the PDK 102 is within the proximity zone 1202. For profile authentication, the Reader 108 automatically determines which PDK 102 should be associated with an authentication test and the transaction. For example, if the Reader 108 receives a biometric input 122 from an individual, the Reader 108 automatically determines which PDK 102*a-d* is associated with the individual supplying the biometric input 122. In another embodiment, a different trigger is detected (e.g., a PIN input) to initiate the differentiation decision. In yet another embodiment, the differentiation decision is initiated without any trigger. It is noted that in some embodiments, where no trigger is required (such as a registry authentication), no differentiation decision is made and authentications are instead performed for each PDK 102 within the proximity zone 1202.

Figure 13:
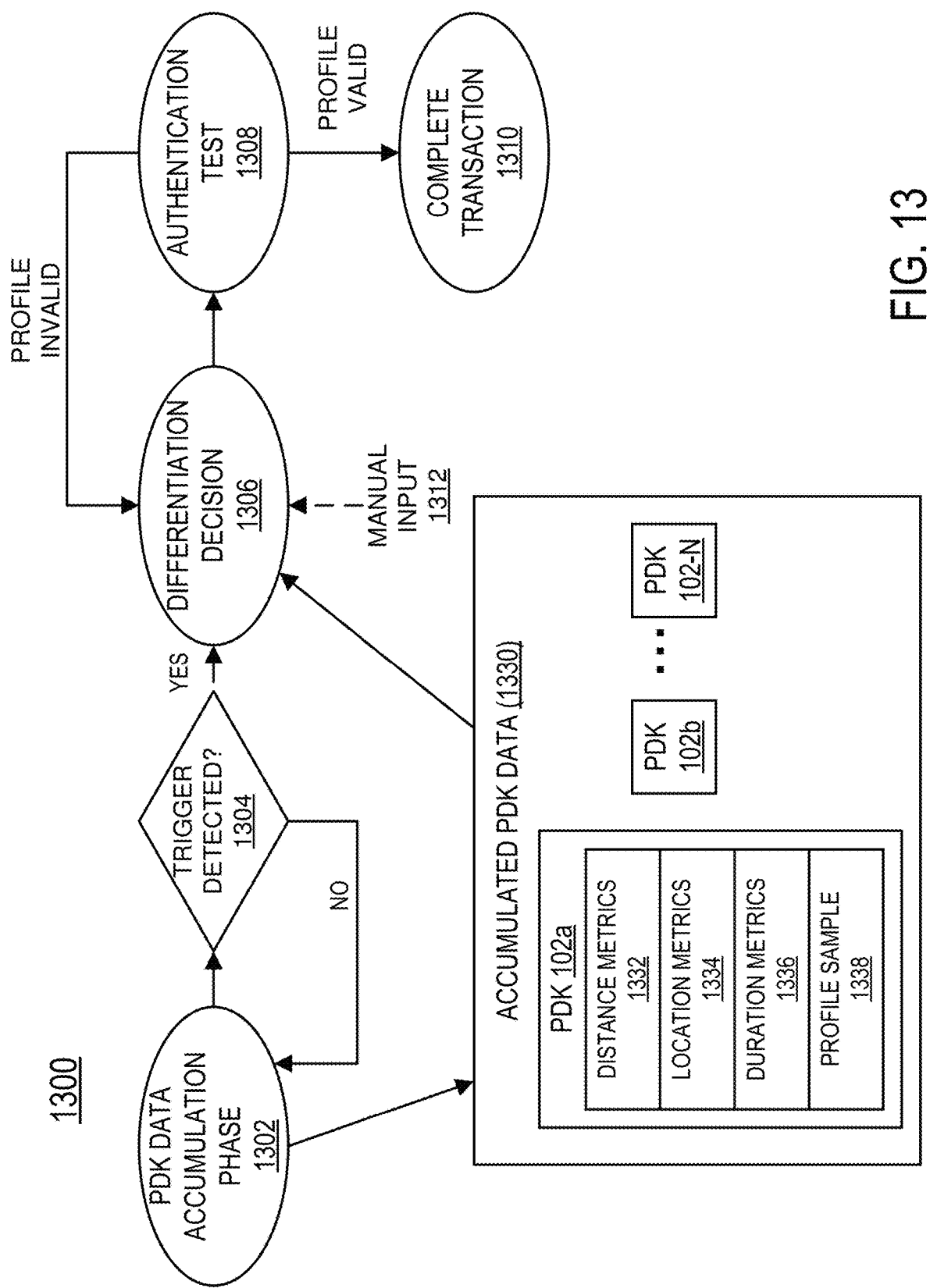
FIG. 13 is a flowchart illustrating one embodiment of a process for differentiating between multiple PDKs in completing a secure authentication process.

FIG. 13 illustrates an embodiment of an authentication process 1300 for the scenario where multiple PDKs 102 are present within the proximity zone 1202 of the Reader 108. In a PDK data accumulation phase 1302, PDK data 1330 is accumulated and buffered in the Reader 108 for any valid PDKs 102 that enter the proximity zone 1202. In one embodiment, the accumulation phase 1302 begins for a PDK 102 after it has been within the proximity zone 1202 for a predetermined period of time. In one embodiment, the PDK data accumulation phase 1302 is similar to the steps 802-808 described above in detail with reference to FIG. 8 for each PDK 102*a-d* in the proximity zone 1202.

As illustrated, the accumulated PDK data 1330 includes one or more differentiation metrics from each valid PDK 102 within range of the Reader 108. The differentiation metrics can include any information that can be used by the Reader 108 to determine which PDK 102 should be associated with the authentication and/or transaction request. According to various embodiments, differentiation metrics can include one or more of distance metrics 1332, location metrics 1334 and duration metrics 1336.

In one embodiment, a distance metric 1332 indicates the relative distance of a PDK 102 to the Reader 108. This information is useful given that a PDK 102 having the shortest distance to the Reader 108 is generally more likely to be associated with a received authentication trigger (e.g., a biometric input, a PIN input or a transaction request). The distance metrics 1332 can include, for example, bit error rates, packet error rates and/or signal strength of the PDKs 102. These communication measurements can be obtained using a number of conventional techniques that will be apparent to those of ordinary skill in the art. Generally, lower error rates and high signal strength indicate the PDK 102 is closer to the Reader 108.

Location metrics 1334 can be used to determine a location of a PDK 102 and to track movement of a PDK 102 throughout an area. This information can be useful in determining the intent of the PDK holder to execute a transaction. For example, a PDK holder that moves in a direct path towards a cashier and then stops in the vicinity of the cashier is likely ready to make a purchase (or may be waiting in line to make a purchase). On the other hand, if the PDK moves back and forth from the vicinity of a cashier, that PDK holder is likely to be browsing and not ready to make a purchase. Examples of systems for determining location metrics are described in more detail below with reference to FIGS. 14-15.

The differentiation metrics can also include duration metrics 1336 that tracks the relative duration a PDK 102 remains within the proximity zone 1202. Generally, the PDK 102 with the longest time duration within the proximity zone 1202 is most likely to be associated with the authentication request. For example, if the Reader 108 is busy processing a purchasing transaction at a cashier and another PDK 102 has a long duration within the proximity zone 1202, it is likely that the user is waiting in line to make a purchase. In one embodiment, the Reader 108 tracks duration 1336 by starting a timer associated with a PDK 102 when the PDK 102 enters the proximity zone 1202 and resetting the time to zero when the PDK exists. As another example, the Reader 108 tracks the duration when a PDK of a doctor enters the proximity zone of a patient's room. A long duration of the doctor's PDK within the proximity zone can provide evidence that the doctor is spending an adequate amount of time examining the patient. On the other hand, a short duration of the doctor's PDK within the proximity zone can provide evidence that the doctor just merely stopped by and did not perform any thorough examination. This information is useful in monitoring patient treatment and provider performance to help ensure quality patient care.

In one embodiment, the Reader 108 can also receive and buffer profile samples 1338 prior to the start of a profile authentication instead of during the authentication process as described in FIG. 11A-11B. In one embodiment, the Reader 108 determines which types of biometric profile samples 1338 to request based on, for example, the configuration of the Reader 108, the type of transactions performed by the Reader 108, or manual requests from a clerk, security guard, etc. In one embodiment, the PDK 102 transmits one or more of the requested sample types based on profiles available in the PDK 102 and/or user preferences. In another embodiment, the PDK 102 transmits one or more samples 1338 it has available and only samples that match the authentication types configured for the Reader 108 are buffered. For example, if a Reader 108 is configured for fingerprint authentication, a PDK 102 may transmit samples 1338 for several different fingerprint profiles (each corresponding to a different finger, for example). It will be apparent to one of ordinary skill in the art that other variations are possible to provide flexibility in both the configuration of the Reader 108 for various types of authentication and flexibility for the PDK owner to determine which types of authentication to use.

Because profile samples 1338 only comprise a subset of the profile information, in one embodiment, the samples can be safely transmitted over a public channel without needing any encryption. In another embodiment, the profile samples 1338 are transmitted with at least some level of encryption. In yet another embodiment, some of the data is transmitted over a public communication channel and additional data is transmitted over a secure communication channel. In different configurations, other types of profile information can be accumulated in advance. For example, in one embodiment, a photograph from a picture profile can be obtained by the Reader 102 during the data accumulation phase 1302. By accumulating the profile sample 1338 or other additional information in advance, the Reader 108 can complete the authentication process more quickly because it does not wait to receive the information during authentication. This efficiency becomes increasingly important as the number of PDKs 102 within the proximity zone 1202 at the time of the transaction becomes larger.

The PDK accumulation phase 1302 continues until a trigger (e.g., detection of a biometric input) is detected 1304 to initiate a profile authentication process. If a biometric input is received, for example, the Reader 108 computes a mathematical representation or hash of the input that can be compared to a biometric profile and computes one or more input samples from the biometric input. It is noted that in alternative embodiments, the process can continue without any trigger. For example, in one embodiment, the transaction can be initiated when a PDK 102 reaches a predefined distance from the Reader 108 or when the PDK 102 remains within the proximity zone 1202 for a predetermined length of time.

The process then computes a differentiation decision 1306 to determine which PDK 102*a-d* should be associated with the authentication. In one embodiment, the Reader 108 computes a differentiation result for each PDK using one or more of the accumulated data fields 1330. For example, in one embodiment, the differentiation result is computed as a linear combination of weighted values representing one or more of the differentiation metrics. In another embodiment, a more complex function is used. The differentiation results of each PDK 102 are compared and a PDK 102 is selected that is most likely to be associated with the transaction.

In another embodiment, for example, in a photo authentication, the differentiation decision can be made manually by a clerk, security guard, or other administrator that provides a manual input 1312. In such an embodiment, a photograph from one or more PDKs 102 within the proximity zone 1202 can be presented to the clerk, security guard, or other administrator on a display and he/she can select which individual to associate with the transaction. In yet another configuration, the decision is made automatically by the Reader 108 but the clerk is given the option to override the decision.

An authentication test 1308 is initiated for the selected PDK 102. The authentication test 908 can include one or more of the processes illustrated in FIGS. 11A-11D. Note that if profile samples 1338 are acquired in advance, they need not be acquired again in the authentication steps of FIGS. 11A-11B. It is additionally noted that in one embodiment, the Reader 108 compares the profile samples 1338 of the PDKs 102 to the computed input sample until a match is found before performing a full profile comparison. In one embodiment, the Reader first compares samples from the selected PDK 102 until a match is found. For example, a Reader 108 may have accumulated multiple fingerprint profiles samples 1338 (e.g., corresponding to different fingers) for the selected PDK 102. The Reader 108 receives a fingerprint input from, for example, the left index finger, computes the input sample, and does a quick comparison against the accumulated samples 1338 for the selected PDK 102 to efficiently determine a matching profile. The Reader 108 then performs the full comparison using the matching profile. In an alternative embodiment, the Reader 108 performs a comparison of a first sample from each PDK 102 and if no match is found, performs comparisons of second samples from each PDK 102. It will be apparent to one of ordinary skill in the art that samples can be compared in a variety of other orders without departing from the scope of the invention.

If the authentication test 1308 indicates a valid profile, the transaction is completed 1310 for the matching PDK 102. If the authentication test 1308 determines the profile is invalid, a new differentiation decision 1306 is made to determine the next mostly likely PDK 102 to be associated with the transaction. The process repeats until a valid profile is found or all the PDKs 102 are determined to be invalid.

Figure 14:
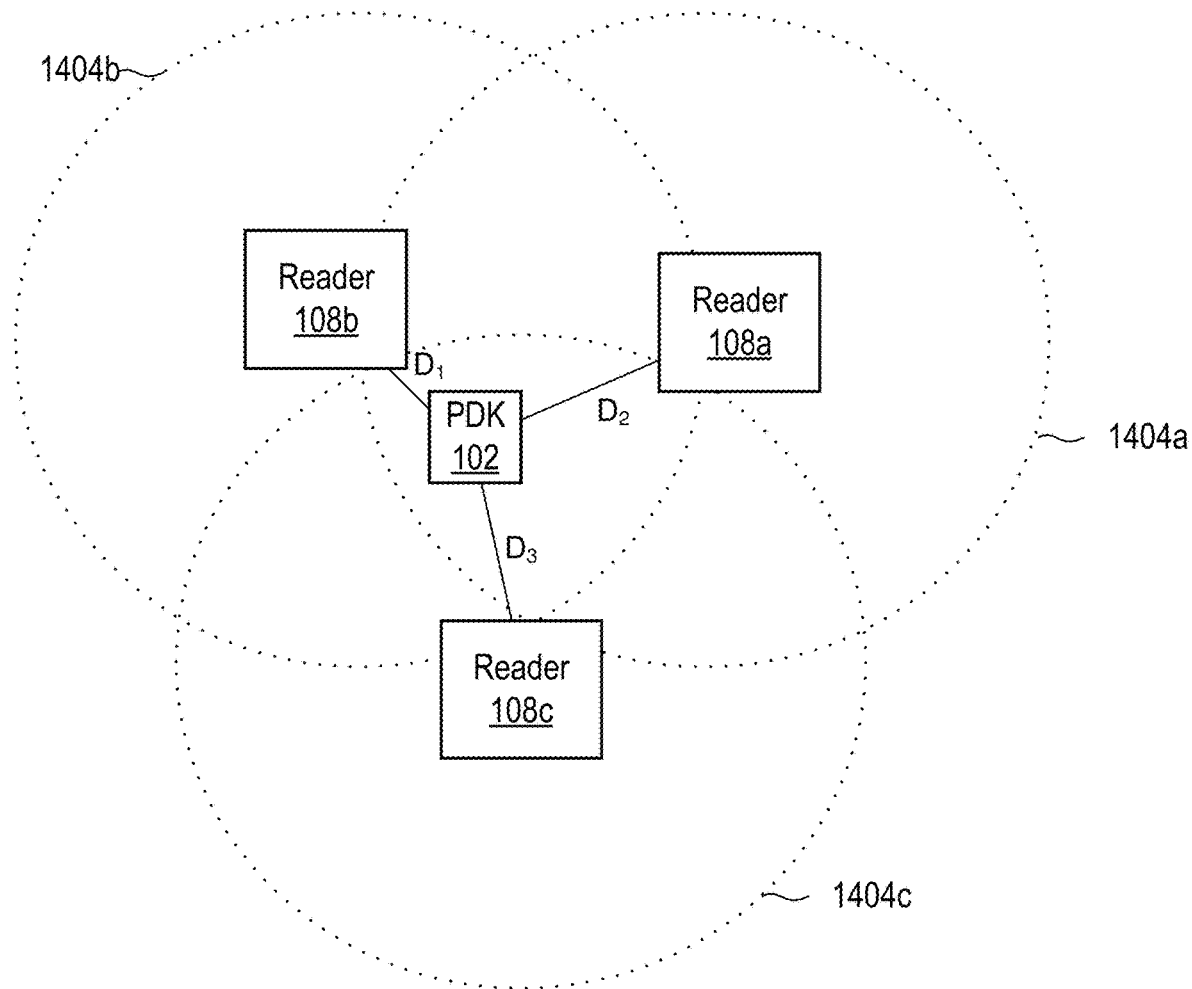
FIG. 14 is a block diagram illustrating an embodiment of a system for estimating location of a PDK using coordinate triangulation.

Turning now to FIG. 14, an example system is illustrated for determining a location metric 1334 of a PDK 102 using a coordinate triangulation technique. In one embodiment of coordinate triangulation, multiple transmitting devices (e.g., Readers 108*a-c*) are spaced throughout an area. In one embodiment, the Readers 108*a*-care coupled by a network. Each Reader 108*a-c* has a range 1404 and the ranges 1404 overlap. Each Reader 108*a-c* determines a distance D1-D3 between the Reader 108 and the PDK 102. Distance may be estimated, for example, by monitoring signal strength and/or bit error rate as previously described. Then using conventional trigonometry, an approximate location of the PDK 102 can be calculated from D1-D3. Although only three transmitters are illustrated, it will be apparent that any number of transmitters can be used to sufficiently cover a desired area. Location information can be computed at predetermined time intervals to track the movement of PDKs throughout a facility.

Figure 15:
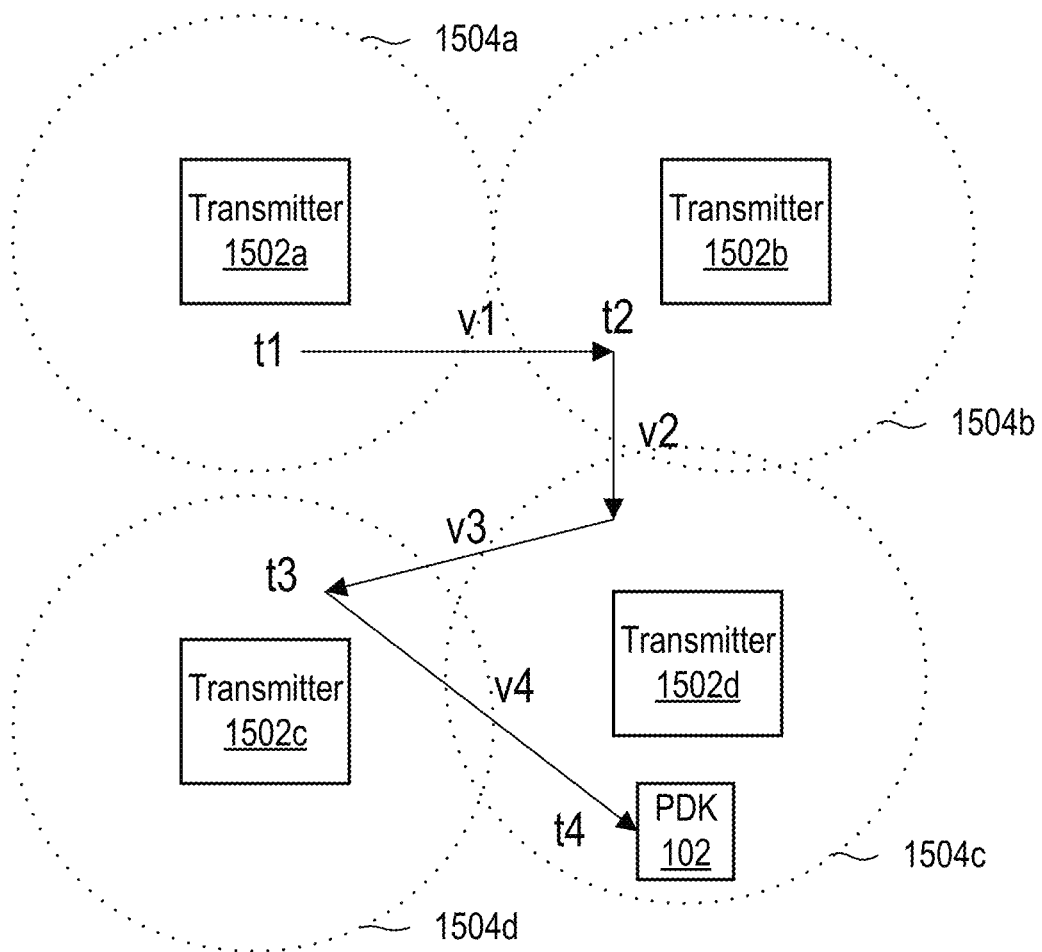
FIG. 15 is a block diagram illustrating an embodiment of a system for location tracking of a PDK.

Another embodiment of location tracking is illustrated in FIG. 15. Here, transmitters 1502 having ranges 1504 are distributed throughout an area. The ranges 1504 can vary and can be overlapping or non-overlapping. In this embodiment, each transmitter 1502 can detect when a PDK 102 enters or exists its range boundaries 1504. By time-stamping the boundary crossings, a location vector can be determined to track the PDK's movement. For example, at a first time, t1, the PDK 102 is detected within the range of transmitter 1502*a*. At a second time, t2, the PDK 102 is detected within the range of transmitter 1502*b*. At a third time, t3, the PDK 102 is within the range of transmitter 1502*c* and at a fourth time, t4, the PDK 102 is within the range of transmitter 1502*d*. Using the location and time information, approximate motion vectors, v1, v2, v3, and v4 can be computed to track the motion of the PDK 102 without necessarily computing exact distance measurements.

Figure 16:
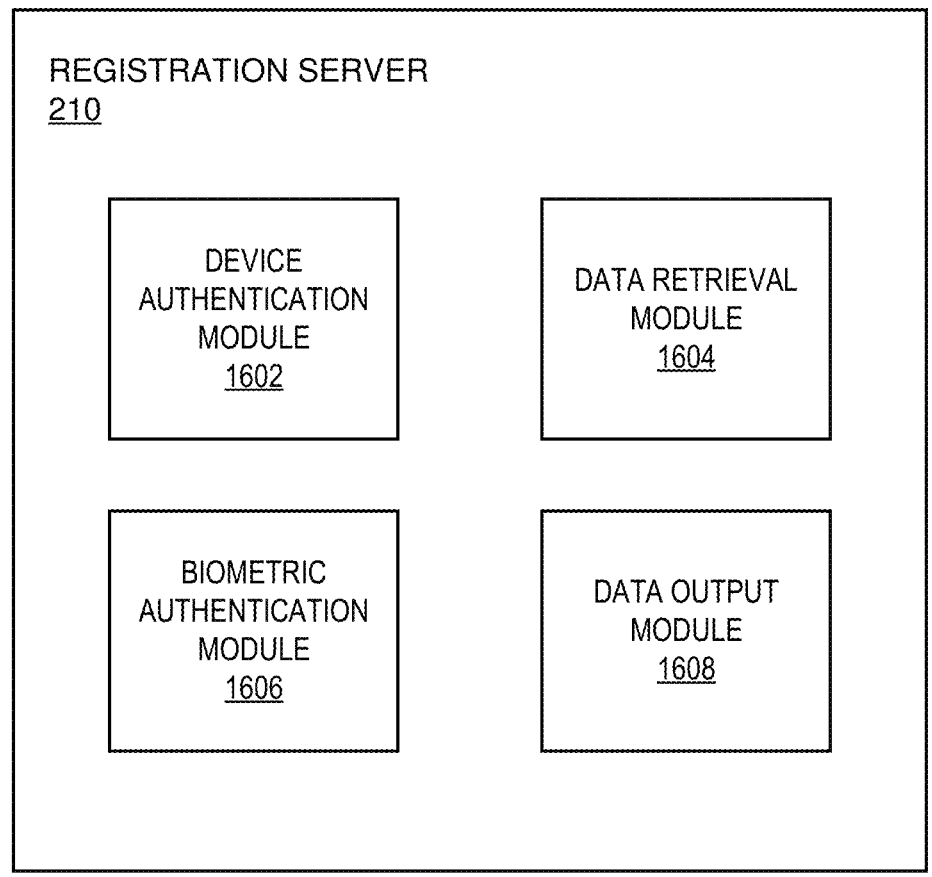
FIG. 16 is a block diagram illustrating an embodiment of a registration server.

FIG. 16 is a block diagram illustrating an embodiment of registration server 210. The registration server 210 includes software routines for automating the process of registering new patients and ensures that a patient never needs to register more than once. The registration server 210 includes a device authentication module 1602, data retrieval module 1604, biometric authentication module 1606 and data output module 1608. The device authentication module 1602 receives PDK information sent by a Reader 108 and is coupled to the biometric authentication module, which receives biometric data from the PDK 102 and performs biometric authentication. The device authentication is also coupled to the data retrieval module 1604. By automating patient registration, the registration server 210 saves time and expense as well as reduces errors and patient frustration.

Figure 17:
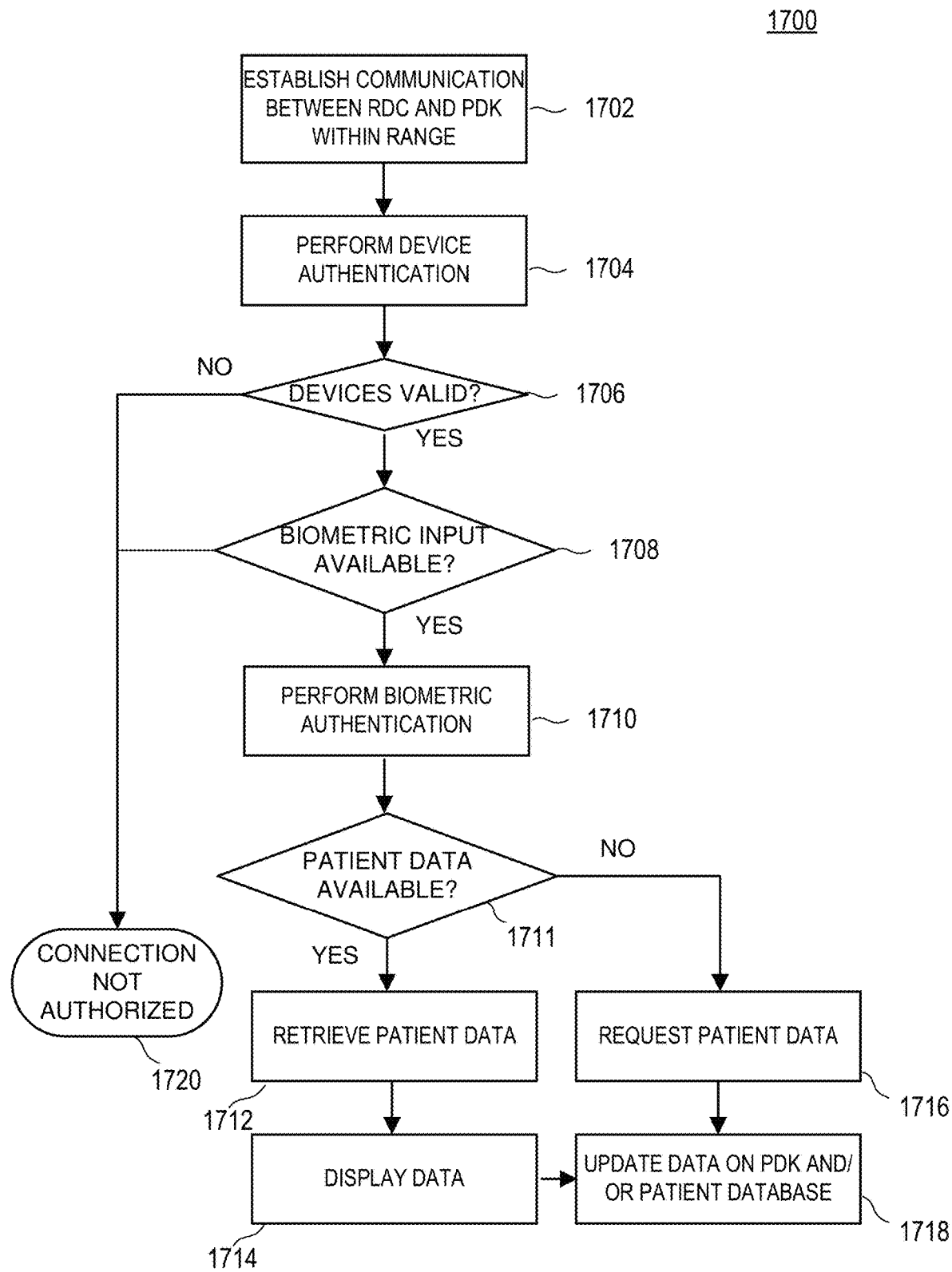
FIG. 17 is a flowchart illustrating one embodiment of a process for automatic patient registration.

FIG. 17 is a flowchart illustrating one embodiment of a process 1700 for automatic patient registration. When a patient carrying or wearing a PDK comes within the range of a Reader 108, communication is automatically established 1702 between the RDC 604 of the Reader 108. Once communication with the PDK 108 is established, device authentication 1704 is performed.

In one embodiment, the device authentication module 1602 performs 1704 device authentication. In another embodiment, the device authentication is performed by the Reader 108 as described in step 804 of FIG. 8. An example embodiment of a method for performing 1704 device authentication is illustrated in the previous FIG. 9.

Next, the device authentication module 1602 determines 1706 whether the PDK 102 is valid. If the PDK 102 is found to be invalid (1706—No), a connection is not authorized 1720 and the process ends and without automatic registration of the patient. However, if the PDK 102 is found to be valid (1706—Yes), the biometric authentication module 1606 determines 1708 whether biometric input is available and performs 1710 biometric authentication. In one embodiment, a patient provides biometric information by swiping their finger on a Reader 108. In another embodiment, the patient provides biometric information by swiping their finger on the biometric reader 470 of the PDK 102. If biometric information is not available (the patient has not swiped his finger or entered a PIN number), connection is not authorized 1720 and the process ends. If biometric information is available, biometric authentication is performed 1710. Example embodiments for performing biometric authentication are described in FIGS. 11A-D. Those skilled in the art will recognize that depending on the level of authentication desired, the need for steps 1708 and 1710 may be omitted. In other words, for routine procedures like a physical, biometric authentication is not required, while for other more invasive, complex and expensive procedures, biometric authentication is required.

Once biometric authentication is performed 1710, the data retrieval module 1602 of the registration server 210 retrieves information from the PDK 102 to determine 1711 whether patient information is available on the PDK 102. In some embodiments, patient core data is stored in the PDK 102. Patient core data includes some or all of the following information: the patient's name, social security number, emergency contacts, demographics, advanced directives, past medical and surgical history, family and social history, pharmacy contact information, medical insurance information, photo, software application serial number, and other information uniquely identifying the patient. If patient data is available (1711—Yes), the patient data is retrieved 1712 from the PDK 102 and displayed 1714 on the display 718 of the provider interface device 120. The health care provider can then review or update the information as needed. During the patient's visit, new information may be generated. While the PDK 102 is in range, e.g. in the doctor's office, the Reader 108 sends signals to the PDK 102 and the new information is automatically saved 1718 to the patient's PDK. In one embodiment, the new information is also saved to the Central Registry 114 and Private Registries 116a, 116b of the local services module 124. If patient data is not available (1711—No), the registration module 210 requests 1716 patient data. Patient data may then be entered via the provider interface device 120. Once data is entered, the information is saved 1718 to the PDK 102 and/or Central Registry 114 and Private Registries 116.

For example, when a patient enters a provider's facility, the process 1700 described above allows the patient to walk up to the registration table and simply swipe a finger on a biometric reader to check-in for an appointment. This replaces the cumbersome process of the traditional patient check-in procedure with a simple finger swipe, therefore improving patient experience, minimizing entry errors and lowering labor costs.

As another example, when a patient is being examined by a provider, the process 1700 described above allows the patient's retrieved core data to be automatically displayed on the provider interface device 120 in the examining room, operating room or emergency room, therefore making the patient's information easily accessible during examinations, surgery preparation or emergency room treatment.

Figure 18:
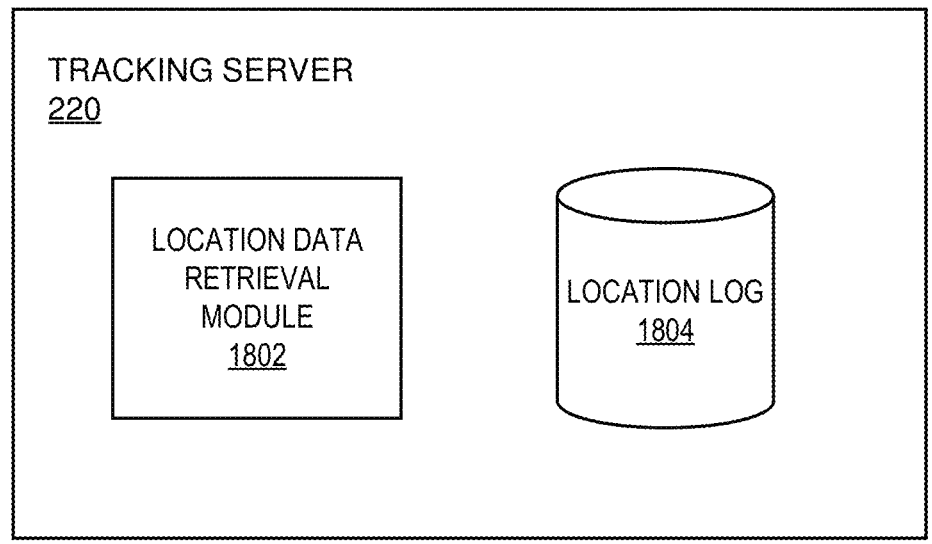
FIG. 18 is a block diagram illustrating an embodiment of a tracking server.

FIG. 18 is a block diagram illustrating an embodiment of a tracking server 220. The tracking server 220 enables real-time tracking of individuals, equipment and supplies by monitoring and storing location information of individuals, equipment or supplies with associated PDKs. Providers can be located immediately in case of an emergency. Location of patients can be monitored to ensure timely administration of medications. Additionally, location of equipment and supplies can also be constantly monitored therefore minimizing search time and inventory surplus requirements. One embodiment of the tracking server 220 includes a location data retrieval module 1802 and a location log. In one embodiment, the location log is a database, such as a Structured Query Language (SQL) database.

In one embodiment, multiple Readers 108 are placed at certain and known positions throughout the healthcare facility. For example, a Reader is placed above each doorway of every room and at every provider interface device 120. In another embodiment, Readers 108 are placed in a grid pattern throughout the healthcare facility. In one embodiment, every provider carries associated PDK uniquely identifying the provider and PDKs are attached to each piece of equipment and every cart of supplies. Example embodiments of a tracking system are described in U.S. patent application Ser. No. 11/939,451 to John Giobbi, et al., entitled "Tracking System Using Personal Digital Key Groups" filed on Nov. 13, 2007, the entire contents of which are incorporated herein by reference.

Figure 19A:
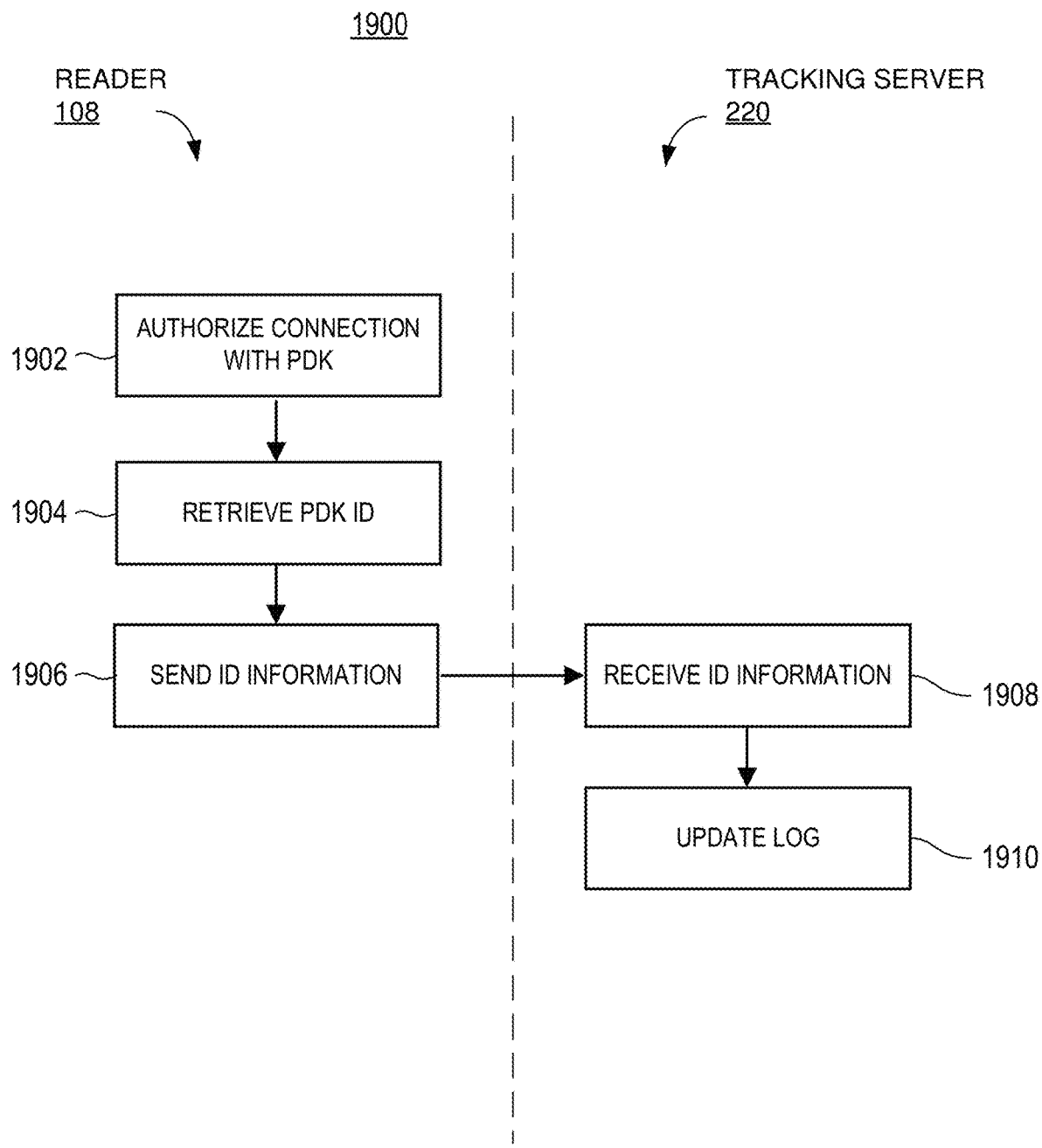
FIG. 19A is a flowchart illustrating one embodiment of a process for tracking of equipment and individuals.

A flowchart illustrating one embodiment of a process 1900 for tracking of equipment and individuals is shown in FIG. 19A. When a PDK comes within the range of a Reader 108, connection is authorized 1902 between the RDC 604 of the Reader 108 and the PDK 102. In one embodiment, the RDC 604 continually transmits beacons that are detected by the PDK 102 when it enters a proximity zone of the Reader 108. In an alternative embodiment, the communication is instead initiated by the PDK 102 and acknowledged by the Reader 108. As shown in the previous FIG. 8, device authentication is first performed and once the Reader 108 establishes if the PDK 102 is a valid device and PDK 102 establishes if the Reader 108 is valid, connection can be authorized.

Once connection is authorized 1902, the Reader 108 retrieves 1904 the PDK 102 information, such as PDK ID 412 and other information identifying the owner or entity associated with the PDK 102. In one embodiment, the reader ID 618 of the Reader 108 is sent to the PDK 102 and stored in the activity log 490 of the PDK 102. The reader and PDK information is sent 1906 to the tracking server 220. The location data retrieval module 1802 receives 1908 the information, including the PDK ID 412. The information is updated 1910 in the location log 1804 of the tracking server 220.

In one embodiment, the location log data is retrieved by the provider interface device 120. In such embodiments, the provider interface device 120 displays the locations of the individuals and equipment being tracked; therefore making it possible to locate anyone and any piece of equipment at any given moment. In some embodiments, the location log data is displayed graphically, for example, with a map of the facility and indications on the map identifying locations of tracked items and people. In other embodiments, the location log data is displayed on the provider interface device 120 with text describing the locations of the tracked items and people.

Figure 19B:
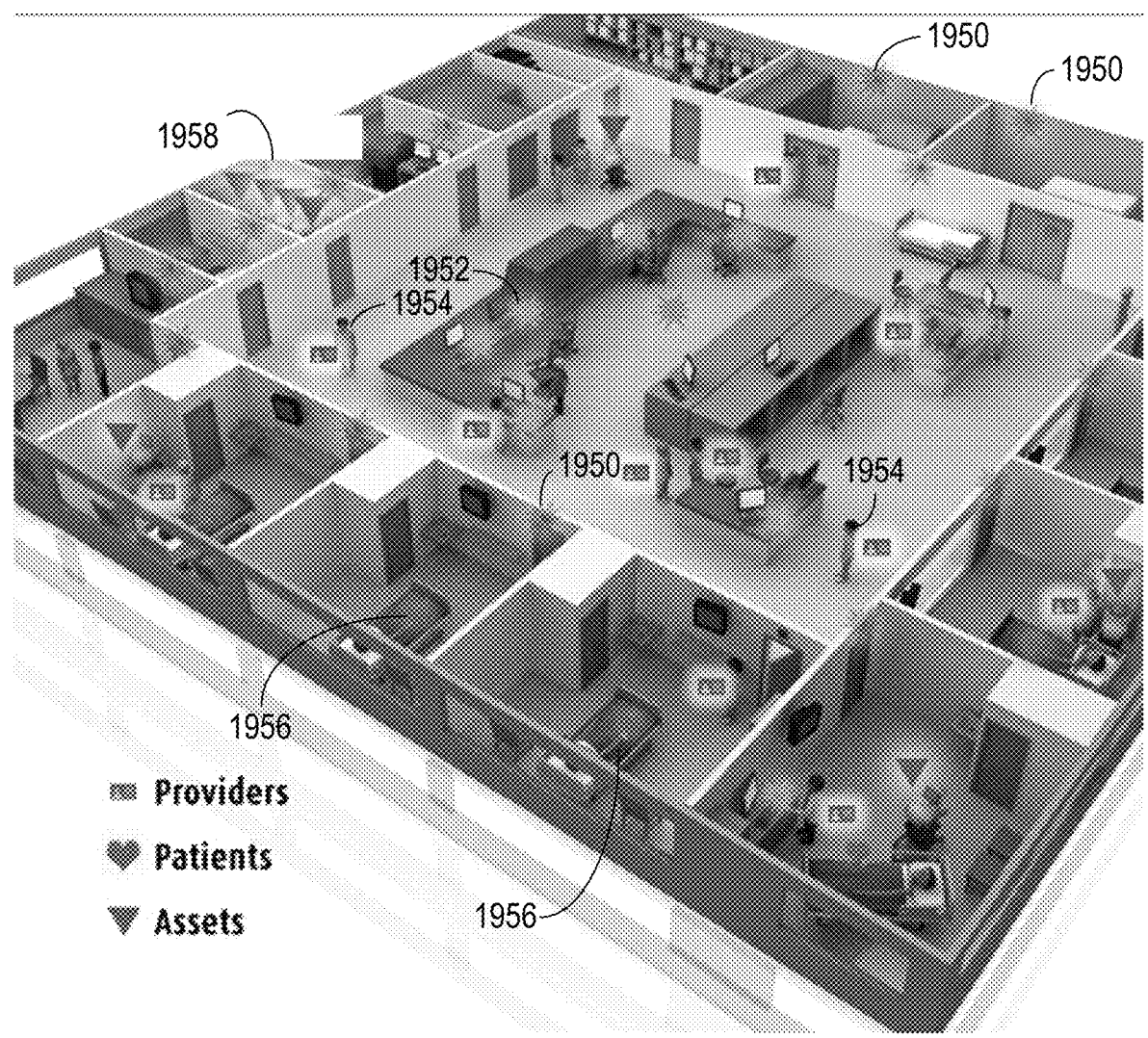
FIG. 19B is a graphical representation illustrating a patient, provider and equipment tracking within a healthcare facility.

This process 1900 occurs whenever a PDK 102 enters the proximity zone of each Reader 108 that it passes enabling constant tracking and location of individuals carrying PDKs and equipment with affixed PDKs. FIG. 19B is a graphical representation illustrating a patient, provider and equipment tracking within a healthcare facility. Readers 1950 are located at various locations throughout the healthcare facility to receive PDK information. Provider interface devices are also equipped with readers 1952 for receiving PDK information. The Readers 1950 and 1952 receive information from the provider PDKs 1954, patient PDKs 1956 and equipment PDKs 1958 enabling the location and tracking of providers, patients and equipment anywhere throughout the healthcare facility.

Figure 20:
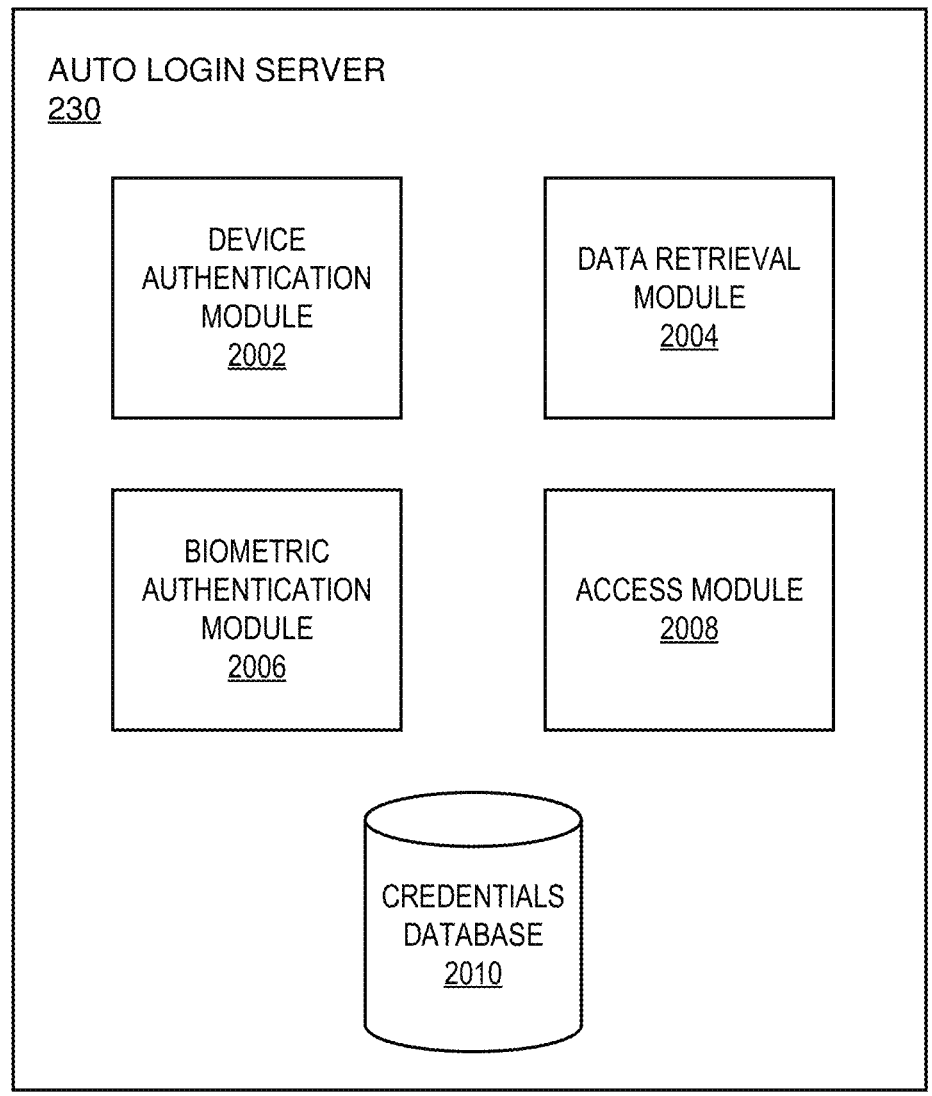
FIG. 20 is a block diagram illustrating an embodiment of an auto login server.

FIG. 20 is a block diagram illustrating an embodiment of an auto login server 230. The auto login server 230 allows for automated electronic signing on of providers into the healthcare computer system, therefore eliminating the constant and time-consuming login and logout of healthcare providers such as doctors, nurses, physician assistants, medical technicians, and other caregivers. In one embodiment, providers can utilize their PDKs to automatically log in to the application software system by simply approaching or entering the proximity zone of a Reader 720 of a provider interface device 120. In such embodiments, no manual input is necessary. The auto login server 230 includes a device authentication module 2002, a data retrieval module 2004, a biometric authentication module 2006, an access module 2008 and a credentials database 2010. In some embodiments the auto login server resides in the local services module 124. The auto login server includes input and output ports for receiving data from and sending data to Readers 108. The device authentication module 2002 is coupled to the biometric authentication module 2006 and data retrieval module 2004. The data retrieval module is couple to communicate with the access module, which is further configured to send access authorization to readers 720, 108 and provider interface device 120.

Figure 21A:
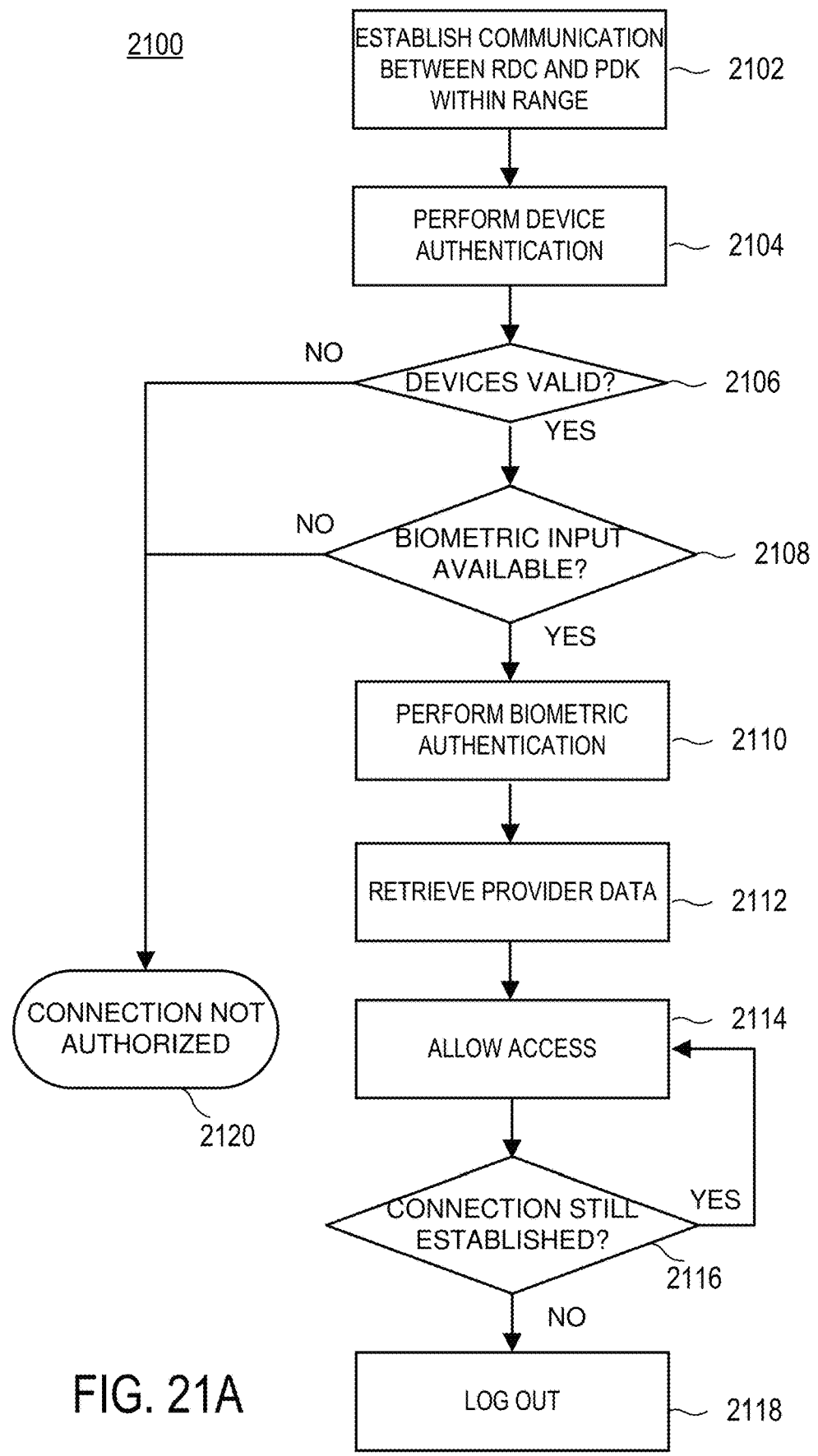
FIG. 21A is a flowchart illustrating one embodiment of a process for automatic login of providers.

FIG. 21A is a flowchart illustrating one embodiment of a process 2100A for automatic login of providers. When a provider carrying or wearing a PDK 102 comes within the range of a Reader 720 of a provider interface device 120, communication is automatically established 2102 between the RDC 604 of the Reader 720 of a provider interface device 120. In one embodiment, the PDK 102 is incorporated into an identification badge of the provider. Once communication with the PDK 108 is established, device authentication is performed 2104.

In one embodiment, the device authentication module 2002 performs 2104 device authentication. In another embodiment, the device authentication is performed by the Reader 108 as described in step 804 of FIG. 8. An example embodiment of a method for performing 2104 device authentication is illustrated in the previous FIG. 9.

Next, the device authentication module 2002 determines 2106 whether the PDK 102 is valid. If the PDK 102 is found to be invalid, connection is not authorized 2116 and the process ends without the logging in of the provider.

If the PDK is found to be valid, the biometric authentication module 2006 determines 2106 if biometric information is available. If biometric information is available, the biometric authentication module 2006 performs 2110 biometric authentication. In one embodiment, a provider provides biometric information by swiping their finger on a Reader 108 of the provider interface device 120. In another embodiment, the provider provides biometric information by entering a PIN number. In yet another embodiment, the provider provides biometric information be swiping their finger on the biometric reader 470 of the PDK 102. If biometric information is not available (the provider has not swiped his finger or entered a PIN number), connection is not authorized 2120 and the process ends. If biometric information is available, biometric authentication is performed 2110. Example embodiments for performing biometric authentication are described in FIGS. 11A-D.

Once biometric authentication is performed 2110, the data retrieval module 2004 of the registration server 210 retrieves information from the PDK 102 of the provider and the access module 2008 allows 2114 access into the healthcare software application system. In some embodiments where biometric authentication is not required, the access module 2008 compares the received data with data stored in the credentials database 2010 to allow or deny access.

In one embodiment, when a login window appears on the provider interface device 120, the medical services application 730 of the provider interface device 120 orchestrates the retrieval of the login credential information from the PDK 102 of the provider and enters the log in information into the login window. In another embodiment, when a login window appears on the provider interface device 120, the medical services application 730 of the provider interface device 120 orchestrates the retrieval of the login credential information from the credentials database 320 and enters the log in information into the login window In some embodiments, provider identifying information is stored in the PDK 102. As long as connection is established (2116—Yes) (the provider is in the proximity zone of the reader 720 of the provider interface device 120), access is allowed 2114. If the provider steps outside the proximity zone of the reader 720, connection is no longer established (2116—No) and the provider is logged out 2118 of the healthcare software application system. Those skilled in the art will recognize that depending on the level of authentication desired, the need for steps 2108 and 2110 may be omitted.

In some embodiments, various rules are applied. In one embodiment, biometric input is required for users who haven't logged in for an extended period of time. In one embodiment, the extended period of time is eight hours. In another embodiment, the extended period of time is twenty four hours. In one embodiment, a secure screen saver is utilized in place of a full login/logout procedure. In another embodiment, the system allows for multiple users to be simultaneously logged in to a single workstation.

Figure 21B:
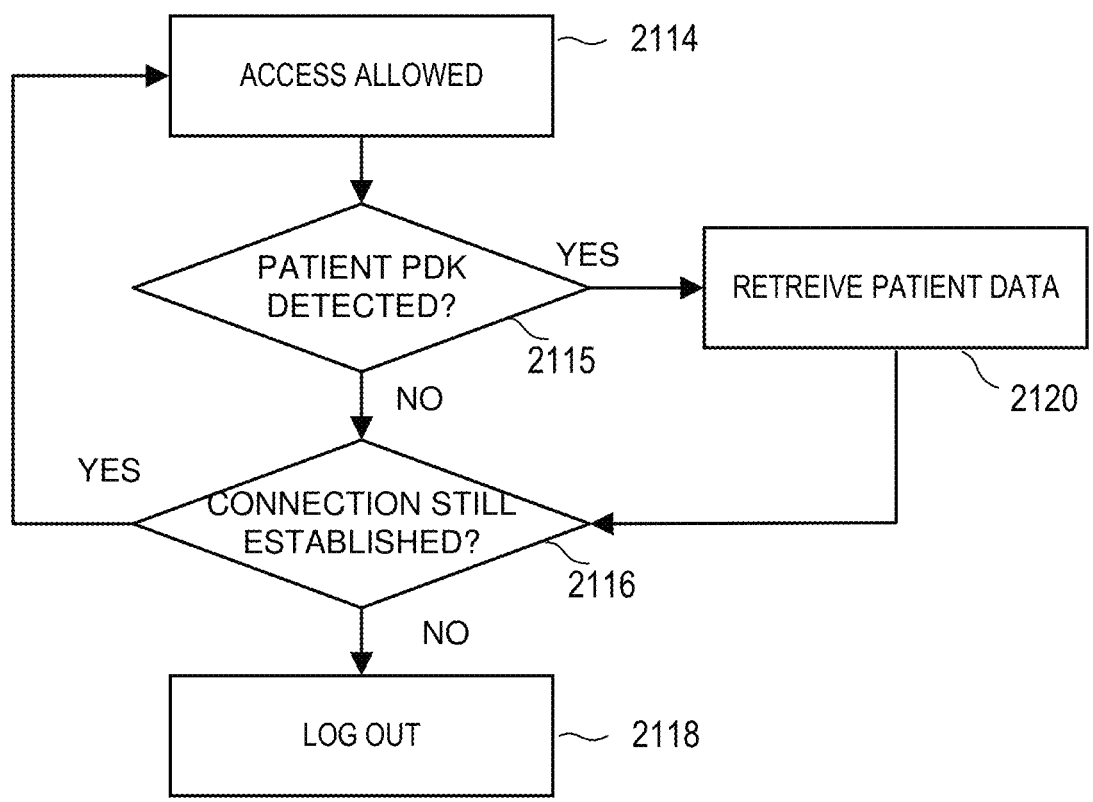
FIG. 21B is a flowchart illustrating another embodiment of a process for automatic login of providers.

FIG. 21B is a flowchart illustrating one embodiment of a process 2100B for automatic login of providers. The steps 2102-2114 of FIG. 21A are the same with the embodiment shown in FIG. 21B. This embodiment allows automatic login when a provider enters an examination room. Once access is allowed 2114, a determination 2115 is made as to whether a patient's PDK is detected, i.e. a patient is waiting in the exam room waiting to be examined. If a patient's PDK is detected (2115—Yes), the patient's data is retrieved 2120. As described above in FIG. 21A, the provider remains logged in as long as connection is still established (2116—Yes). If the patient's PDK is not detected (2115—No), patient data is not retrieved and the provider simply remains logged in as long as connection is established (2126—Yes).

In some embodiments, if the provider makes any changes or annotations to the patient's information while being logged into the system, a notation will be recorded in the patient's information that the particular provider made the change or annotation. This enables accurate tracking of recorded patient data and accountability for patient care.

Figure 21C:
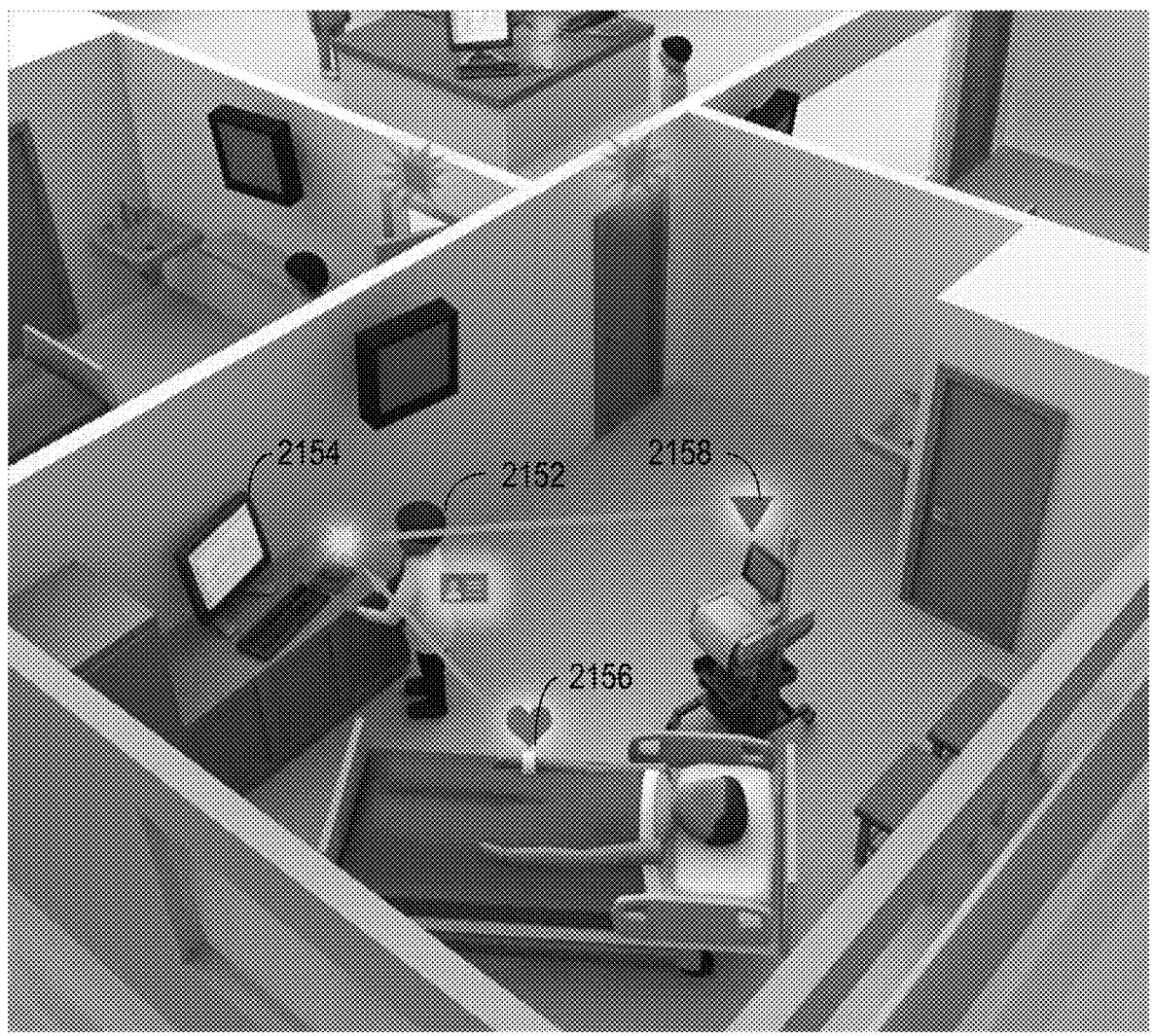
FIG. 21C is a graphical representation of one embodiment of automatic login of providers.

FIG. 21C is a graphical representation of one embodiment of automatic login of providers. In this illustration, a provider 2152 with a unique identifying PDK enters a patient's room and walks up to a provider interface device 2154. The reader of the provider interface device 2154 retrieves information from the provider's 2152 PDK and automatically logs the provider 2152 into the software system. The reader of the provider interface device 2154 also retrieves information from the PDKs 2156 and 2158 of the patient and equipment. The patient's information is then displayed on the provider interface device 2154. In some embodiments, whenever a logged in provider enters or edits a patient's information on the provider interface device 2154, an annotation is made identifying the logged in provider as the user who has made the additions or edits to the patient's information.

Figure 22:
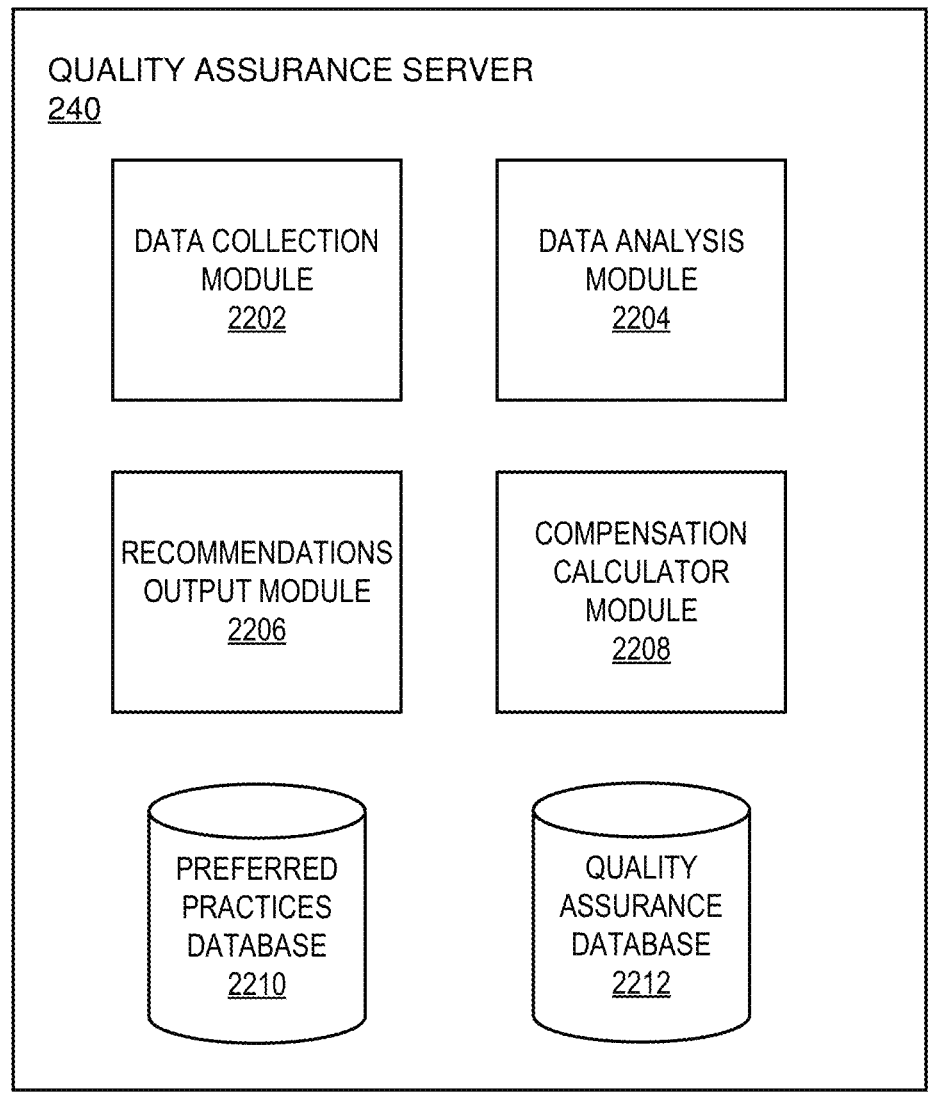
FIG. 22 is a block diagram illustrating an embodiment of a quality assurance server.

FIG. 22 is a block diagram illustrating an embodiment of a quality assurance server 240. The quality assurance server 240 provides recommendations for improving patient care by monitoring patient treatment and provider activity. The quality assurance server 240 includes input and output ports to send and receive data from PDK 102 via the Reader 108 and is also configured to send and receive data from the provider interface device 120. The quality assurance server 240 includes a data collection module 2202, a data analysis module 2204, a recommendations output module 2206, a compensation calculator module 2208, a preferred practices database 2210 and a quality assurance database 2212. The data collections module 2202 is configured to receive data from the Reader 108 and provider interface device 120 and send the data to the data analysis module 2204. The data analysis module 2204 is coupled to the recommendations output module 2206, the compensation calculator module 2208, a preferred practices database 2210 and the quality assurance database 2212. The recommendations output module 2206 is configured to send to the provider interface device 120 and the PDK 102 via the Reader 108.

Figure 23:
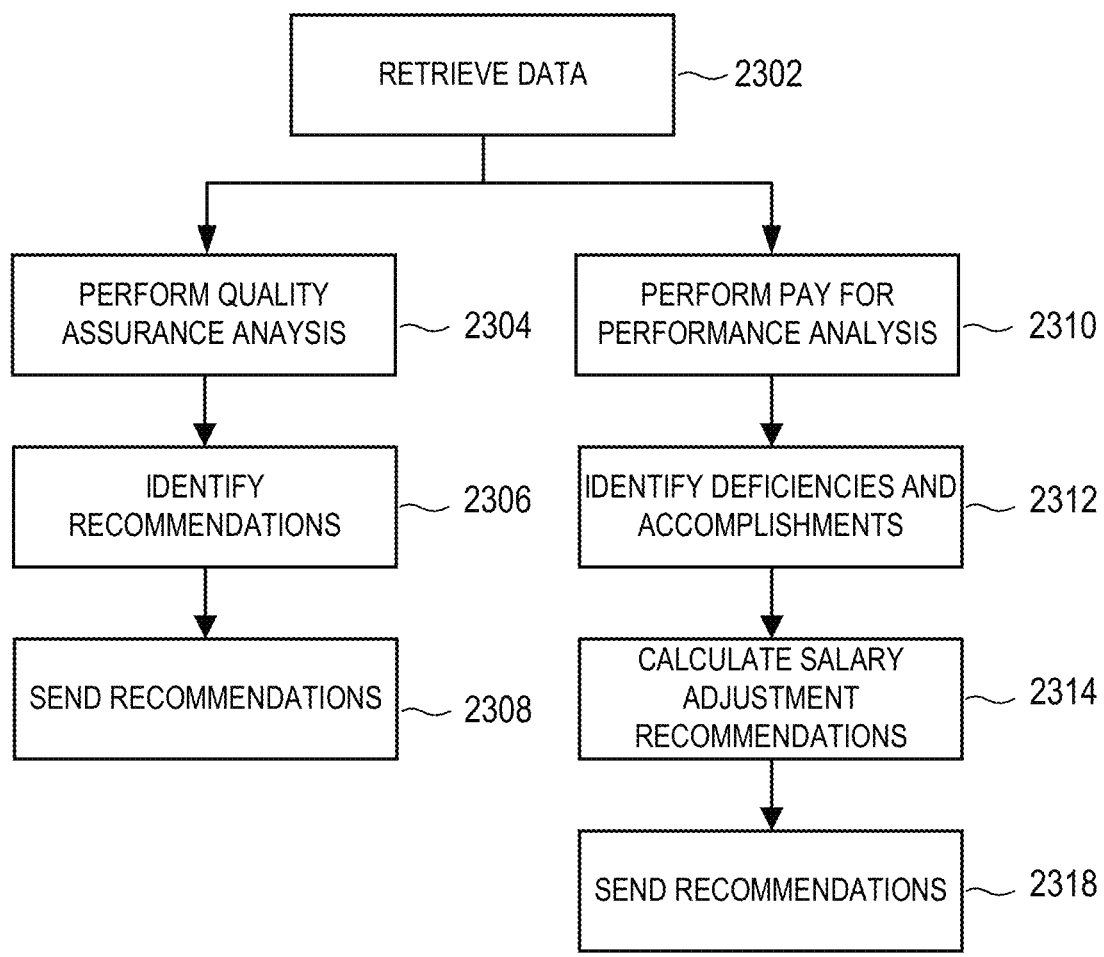
FIG. 23 is a flowchart illustrating one embodiment of a process for analyzing patient care and provider performance.

FIG. 23 is a flowchart illustrating one embodiment of a process 2300 for analyzing patient care and provider performance. The data collection module 2202 retrieves 2302 data from the patient's profile information. In one embodiment, the retrieved data includes the patient's treatment history, prescribed and administered medications, number of doctor's visits, and other information related to the current care and treatment of the patient. In one embodiment, the data is retrieved from the activity log 490 of the patient's PDK 102. A quality assurance analysis is performed 2304 on the data to ensure the optimal care for the patient. The retrieved data is compared with the standards and preferred practices stored in the preferred practices database 2210. The preferred practices database stores standards and preferred practices that define the optimal or recommended care appropriate for a given condition, service or treatment. Recommendations are identified 2306 and sent 2308 to the patient's profile for display on the provider interface device 120. For example, if the comparison of the received data from the activity log 490 shows that correct procedures and treatments have been administered, then this is recorded and stored in the activity log 490 for later use. In some embodiments, the compared information is stored in the quality assurance database 2212.

In another embodiment, analysis of the provider's performance is done 2310 to calculate effect on the provider's compensation. The log which stores the provider's rounds and various treatments given is analyzed and also compared to preferred practices stored in the preferred practices database 2210. Deficiencies and accomplishments are identified 2312. Appropriate salary adjustment is calculated 2314 and recommendations are sent 2318 to affect the provider's compensation.

To illustrate the above in an example, the preferred practices dictates that an admitted patient needs to be visited by his or her provider every four hours, three times a day. Each time a provider visits a patient, information is sent to the patient's PDK 102 and provider's PDK 102 and stored in the activity log 490. The activity data is retrieved 2302 be the data collection module 2202 of the quality assurance server 240. A quality assurance analysis is performed 2304 and monitored data from the activity log 490 is compared with the preferred practices stored in the preferred practices database 2210. In this example, the activity log 490 provides evidence that the doctor only visited the patient two times in one day. Since the preferred practices dictate that the patient should be seen three times, recommendations for more frequent visits are identified 2306 and sent 2308 to the patient's profile for display on the provider interface device 120.

Further, an analysis of the provider's performance is done 2310 to calculate effect on the provider's compensation. Deficiencies in the provider's care are identified 2312 and the appropriate salary adjustment is calculated 2314 and recommendations are sent 2318 to affect the provider's compensation.

Figure 24:
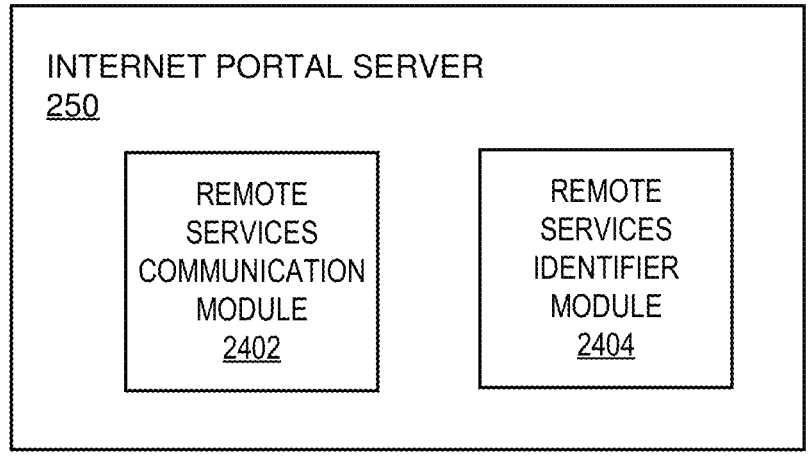
FIG. 24 is a block diagram illustrating an embodiment of an internet portal server.

FIG. 24 is a block diagram illustrating an embodiment of an internet portal server 250. The internet portal server 250 provides a consistent interface to the third party link module 126. Such services may include accessing a patient's virtual database records or insurance information or sending prescription requests to remote pharmacies. The internet portal server 250 includes a remote services communication module 2402 and a remote services identifier module 2404.

Figure 25:
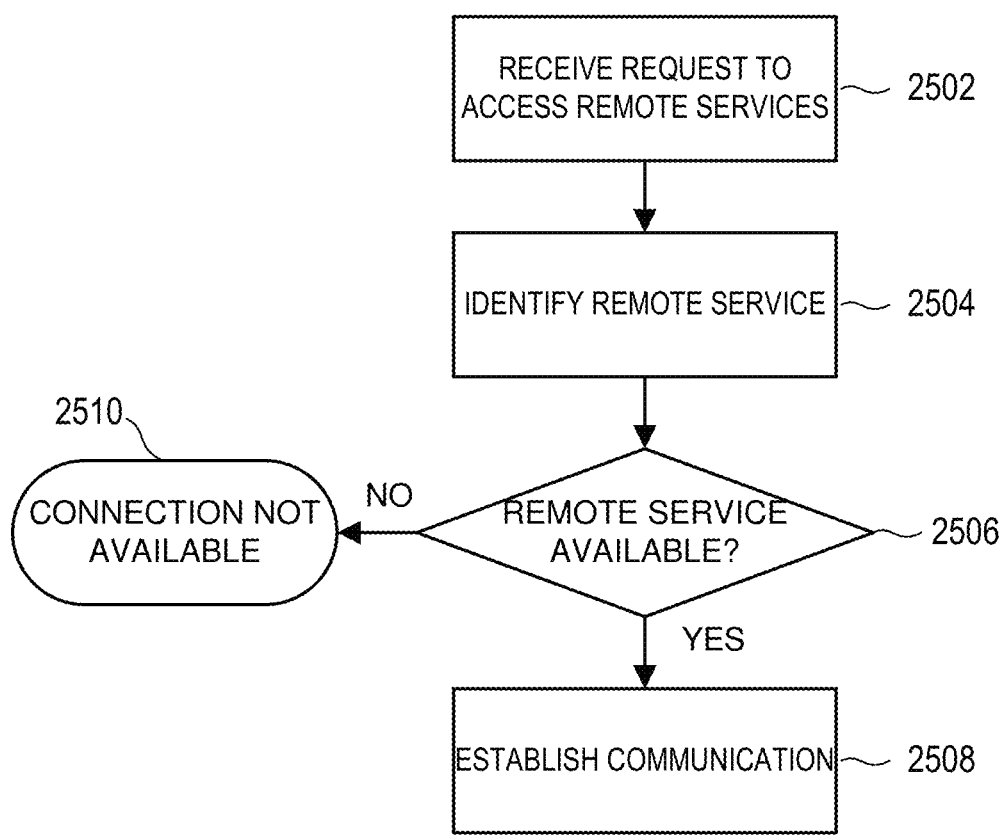
FIG. 25 is a flowchart illustrating one embodiment of a process for communicating with remote services.

FIG. 25 is a flowchart illustrating one embodiment of a process 2500 for communicating with remote services of the third party link module 126. The remote services communication module 2402 receives 2502 a request from a provider interface device 120 to access one of the remote services of the third party link module 126. The remote services identifier module 2404 identifies 2504 which remote service to contact. For example, if the request includes insurance information as well as payment information, the remote services identifier module 2404 determines that the request from the provider interface device 120 needs to communicate with the insurance links server 340 and the billing service server 350.

A determination is then made to determine whether the requested remote service is available 2506. If the remote service is not available (2506—No), then connection is not established. In some embodiments, an error message is sent to the provider interface device 120 with a notification of the unavailability of the requested remote service. If the remote service is available (2506—Yes), communication with that remote service is established 2508.

Figure 26:
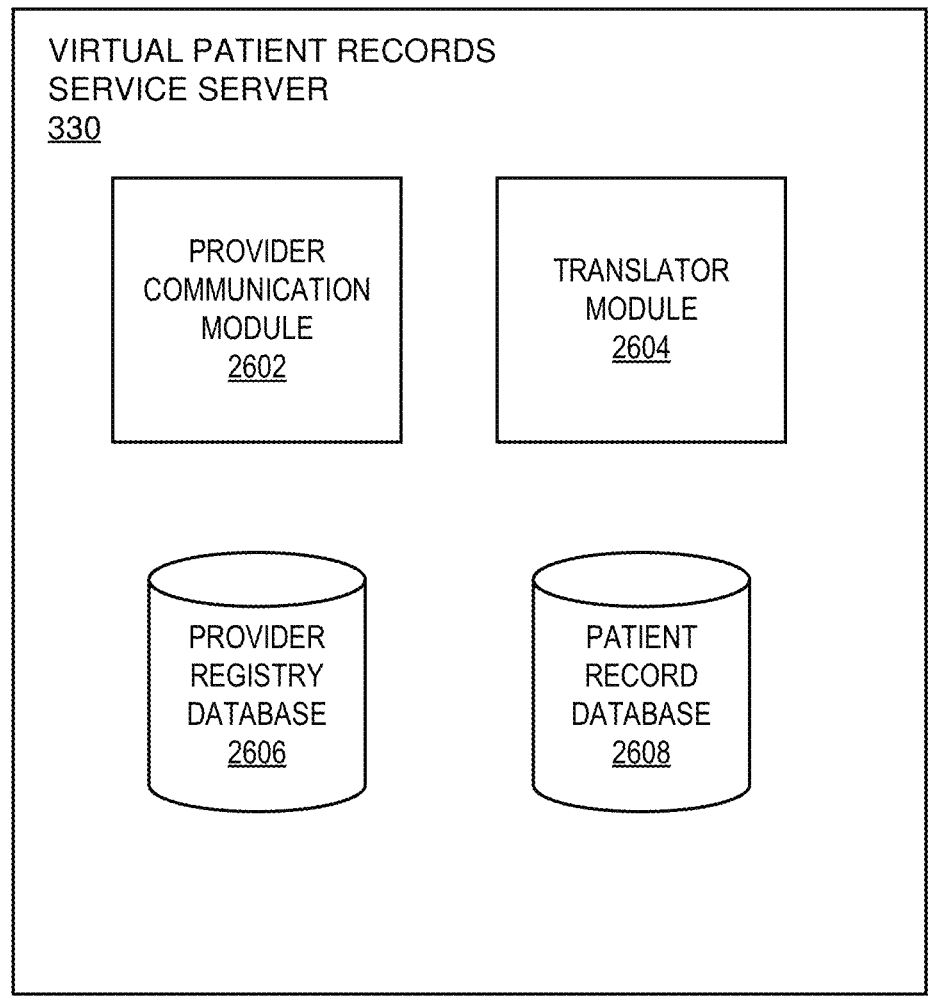
FIG. 26 is a block diagram illustrating an embodiment of a virtual patient records service server.

FIG. 26 is a block diagram illustrating an embodiment of a virtual patient records service server 330. The virtual patient records service server 330 provides a virtual database of a complete record of a patient's medical files by automatically creating links to participating providers' records and enabling centralized and automated access to those records. The virtual patient records service server 330 includes a provider communication module 2602, a translator module 2604, a provider registry database 2606 and a patient records database 2608. The virtual patient records service server 330 includes input and output ports for communicating with the provider interface device 120, the PDK 102 via the Reader 108, and the record system 128. The provider communication module 2602 is configured to receive data from the provider interface device 120 and the PDK 102 via the Reader 108. The provider communication module 2602 is coupled to the translator module 2604, which is coupled to the provider registry database 2606 and patient record database 2608 and configured to send and receive data from the record system 128.

When a patient visits a provider's facility, the patient's medical information may be limitedly available at that provider's facility. Some facilities may store basic information about the patient, such as the patient's name, address, and insurance carrier. However, additional, more detailed information may be needed. The virtual patient records service server 330 provides a seamless link in accessing such detailed information.

The patient records database 2608 stores core data associated with each patient. In one embodiment, core data includes the patient's medical identification number, the patient's provider identification number, medical software information and portal link information. The provider registry database 2606 stores core data associated with particular providers, such as the provider's identification number, the provider's name and contact information. The core data stored in these databases is used to access more detailed information. As described above, the record system 128 is a database for storage of individuals' person health records.

Figure 27:
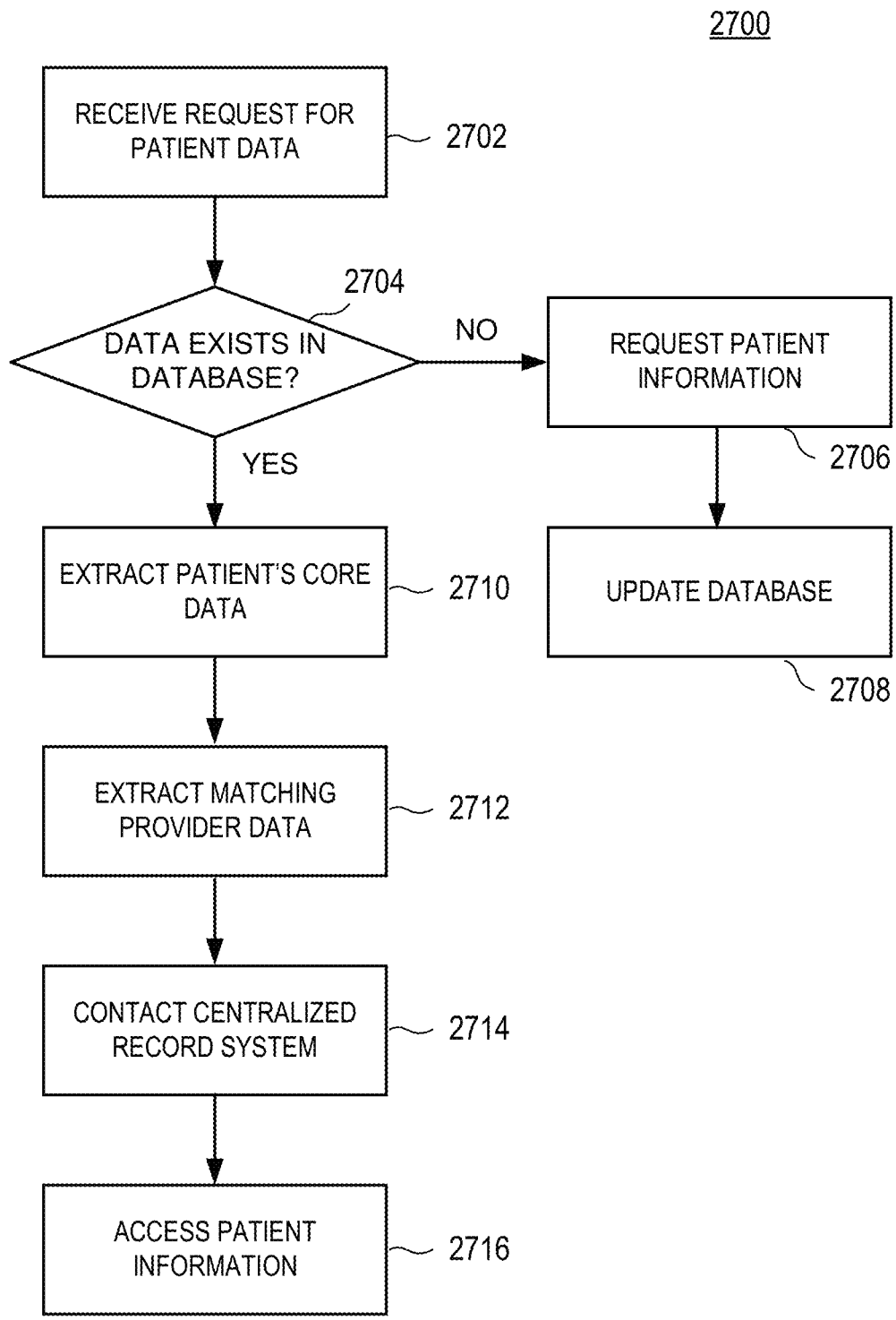
FIG. 27 is a flowchart illustrating one embodiment of a process for accessing virtual patient records.

FIG. 27 is a flowchart illustrating one embodiment of a process 2700 for accessing virtual patient records. The provider communication module 2602 of the virtual patient records service server 330 receives 2702 a request for patient data. A determination 2704 is made as to whether the data exists in the provider registry database 2606 or the patient records database. If the data does not exist (2704—No), patient information is requested 2706 and the provider registry database 2606 and patient records database 2608 are updated and information is stored for later use. The patient information is also sent to the record system 128 for storage. If the data does exist (2704—Yes) in the databases, the patient's core information is extracted from the patient records database 2608 and the corresponding information is extracted 2712 from the provider registry database 2606. The translator module 2604 of the virtual patient records service server 330 interprets the extracted data and contacts 2714 the record system 128. Detailed patient information can then be accessed 2716 from the centralized record system 128.

In one embodiment, any updates and changes stored in the memory 410 of the PDK 102 are sent to the record system 128. In one embodiment, a Reader 108 monitoring the location of an individual's PDK 102 detects when the PDK is about to exit the healthcare facility, for example, if the PDK 102 is approaching a Reader 108 located at a healthcare facility exit, and sends a notification to the virtual patient records service server 330. The virtual patient records service server 330 then instructs the Reader 108 to extract the information from the memory 410 of the PDK 102 and send the information to the records system 128. Similarly, any changes or edits made to the patient's personal health record in the record system 128 is uploaded to the patient's PDK before the patient exits the facility.

Figure 28:
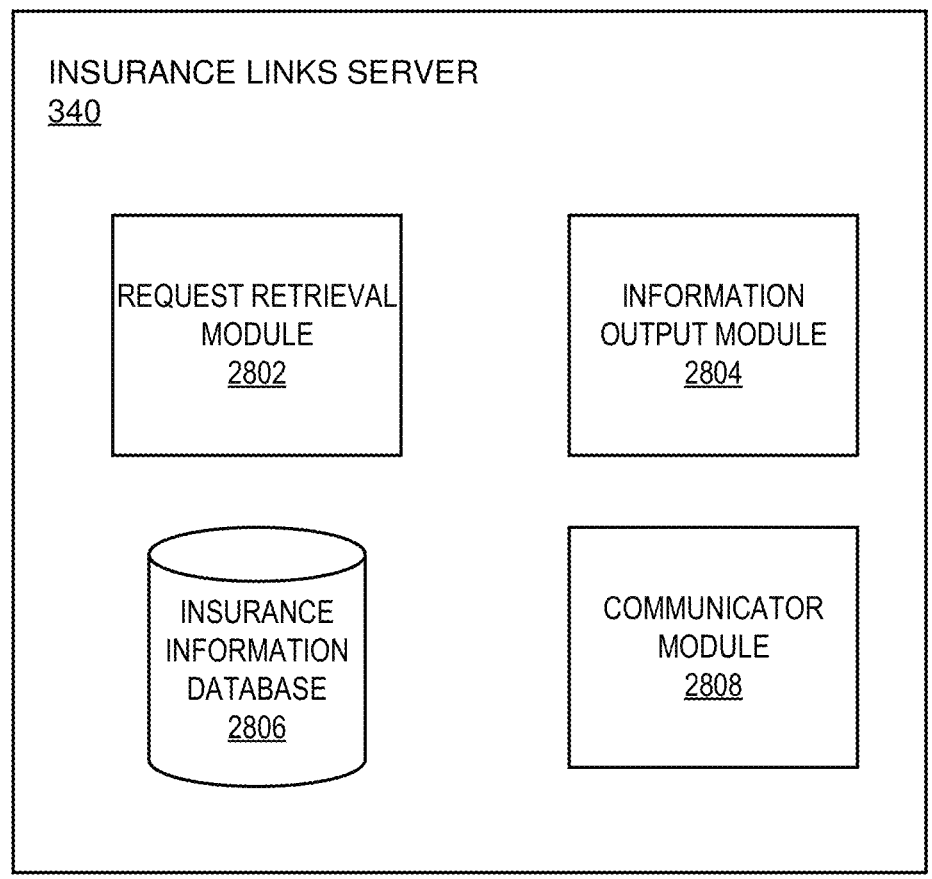
FIG. 28 is a block diagram illustrating an embodiment of an insurance links server.

FIG. 28 is a block diagram illustrating an embodiment of an insurance links server 340. The insurance links server 340 provides a portal of communication between the providers and insurance providers (payors), such as insurance server 144. The insurance links server 340 acts in conjunction with the billing services server 350 to effectively and efficiently update and report patients' billing statements. The insurance links server 340 includes a request retrieval module 2802, an information output module 2804, an insurance information database 2806 and a communicator module 2808.

Figure 29:
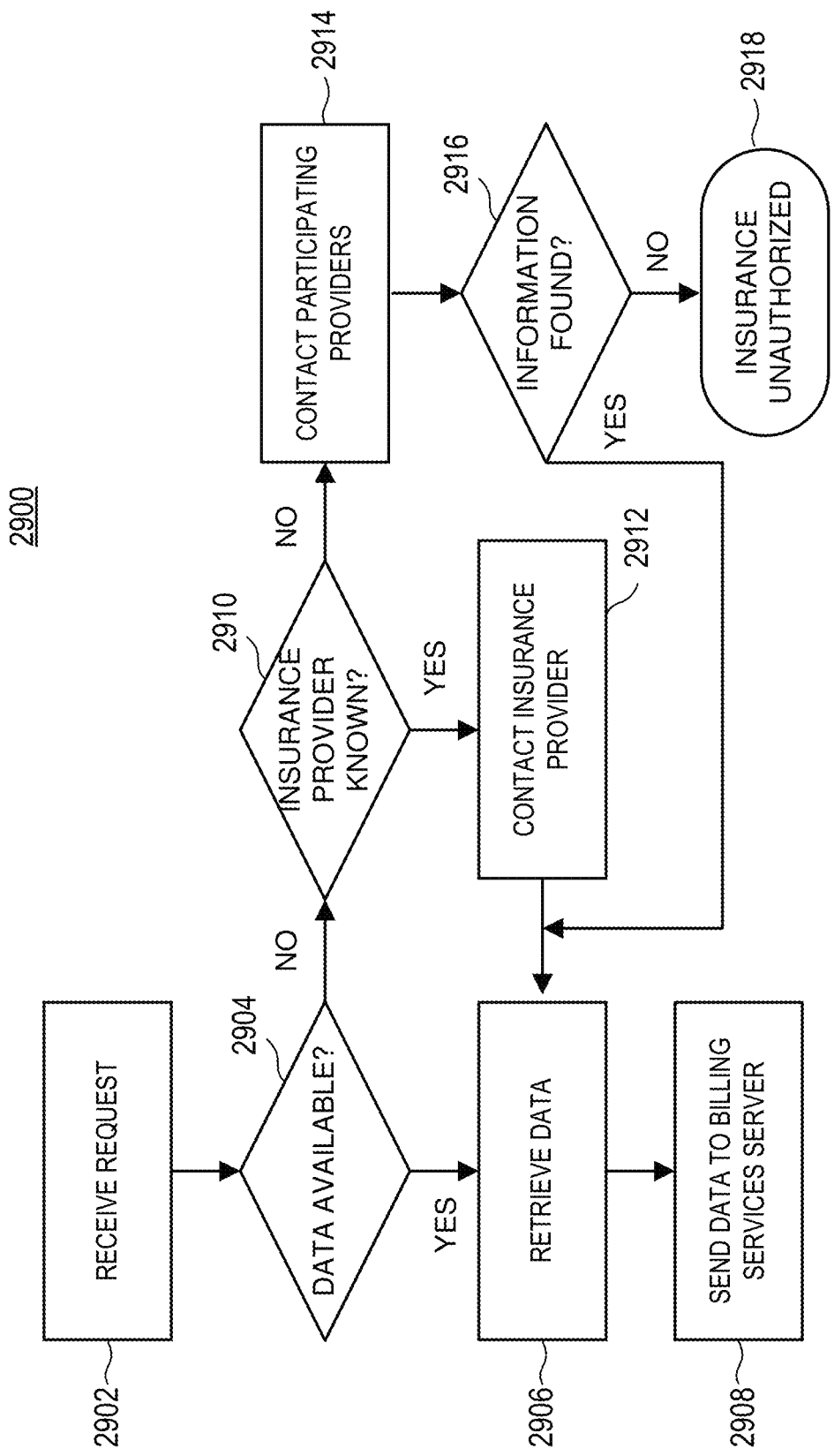
FIG. 29 is a flowchart illustrating one embodiment of a process for accessing patient insurance information.

FIG. 29 is a flowchart illustrating one embodiment of a process 2900 for retrieving and reporting patient insurance information. The request retrieval module 2802 receives 2902 a request for insurance information from an insurance provider service. A determination 2904 is made as to whether the insurance information is locally available in the insurance information database 2806 of the third party link module 126. If the data is locally available (2904—Yes), the insurance data is retrieved 2906 and sent 2908 to the billing services server for further processing. For example, if a patient visits a provider for a routine check-up, a request is sent via the provider interface device 120 to the insurance links server 340 to determine the patient's co-payment. If the co-payment information is available in the insurance information database 2806, that information is then sent to the billing services server 350 to update the patient's records and invoice accordingly.

If the data is not locally available in the insurance information database 2806 (2904—No), a determination is made as to whether the patient's insurance provider is known. If the insurance provider is known (2910—Yes) (i.e. the provider has provided the name of the insurance carrier with the request for information), the insurance provider is contacted 2912 by the communicator module 2808, which then retrieves 2906 the necessary insurance information and sends 2908 the information to the billing services server 350. If the insurance provider is not known (2910—No) (i.e. the provider has not provided the name of the insurance carrier with the request for information), the communicator module 2808 of the insurance links server 340 contacts participating insurance carriers to locate the patient's information. If the information is found (2916—Yes), the communicator module 2808 retrieves 2906 the necessary insurance information and sends 2908 the information to the billing services server 350. If the information is not found (2916—No) in any of the contacted providers, an error message is sent to the provider interface device 120 with a notification that the insurance was not authorized.

Figure 30:
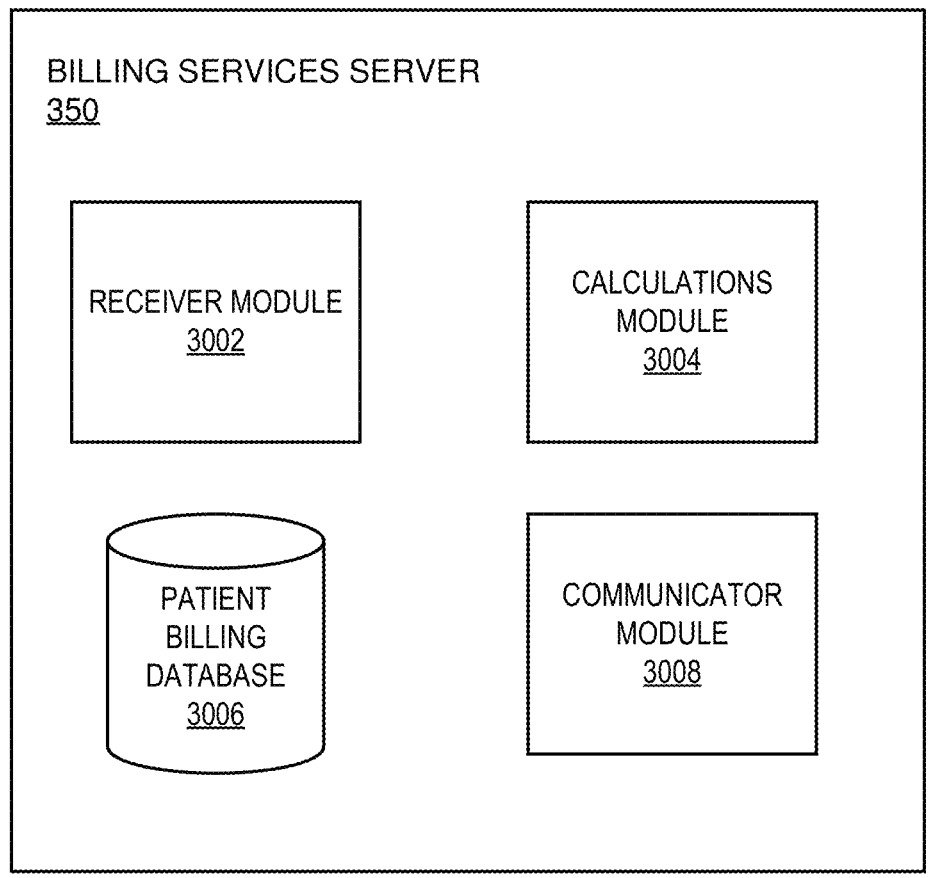
FIG. 30 is a block diagram illustrating an embodiment of a billing services server.

FIG. 30 is a block diagram illustrating an embodiment of a billing services server 350. The billing services server 350 includes a receiver module 3002, a calculations module 3004, a patient billing database 3006 and a communicator module 3008. The billing services server 350 works in cooperation with the insurance link sever 340 to update patient billing information.

Figure 31:
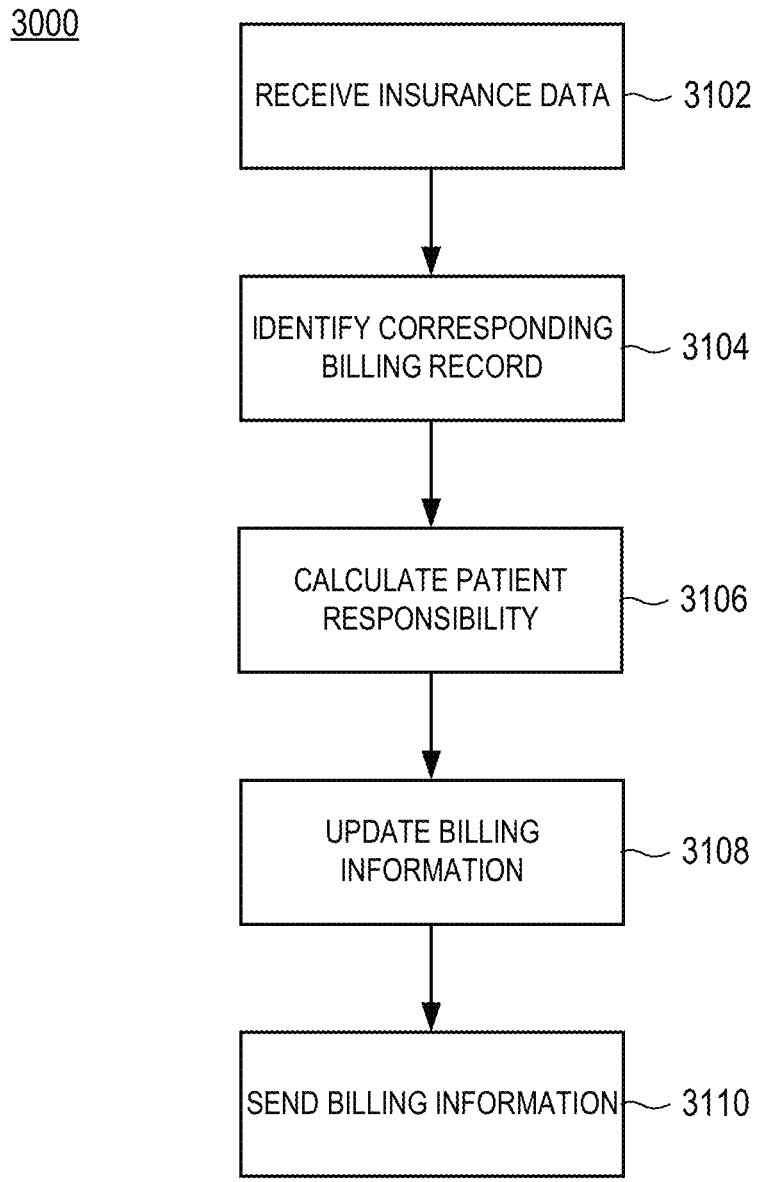
FIG. 31 is a flowchart illustrating one embodiment of a process for updating and reporting patient billing information.

FIG. 31 is a flowchart illustrating one embodiment of a process for updating and reporting patient billing information. The receiver module 3002 receives 3102 insurance data from the insurance links server 340. The corresponding patient billing record is identified 3104 within the patient billing database 3006. The calculations module 3004 calculates 3106 the patient's financial responsibility based on the received insurance information and billing information in the patient billing database 3006 and updates 3108 the patient's statement accordingly. In one embodiment, the updated billing information is stored in the patient billing database 3006. In another embodiment, the updated billing information is sent 3110 by the communicator module 3008 to be stored in the profile information of a patient's PDK.

Figure 32:
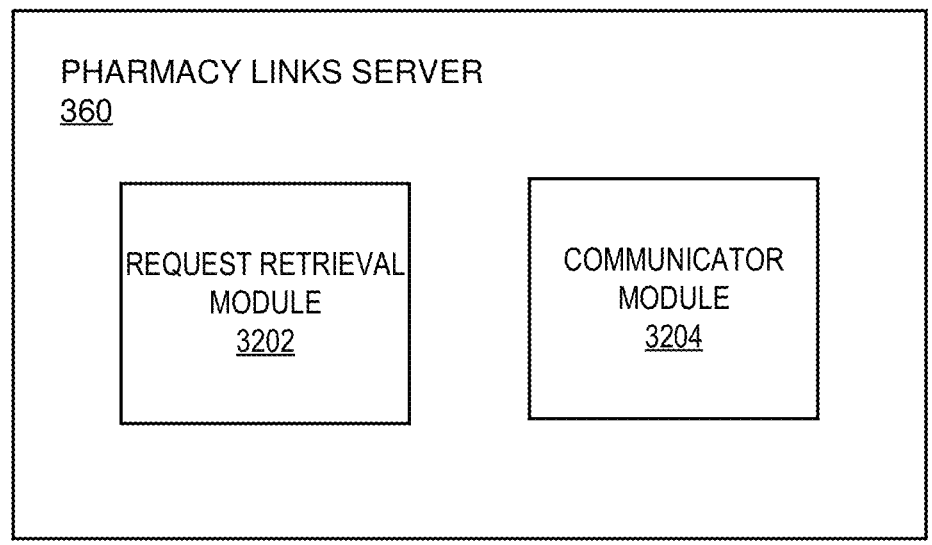
FIG. 32 is a block diagram illustrating an embodiment of a pharmacy links server.

FIG. 32 is a block diagram illustrating an embodiment of a pharmacy links server 360. The pharmacy links server 360 provides a portal of communication between health care providers and patients pharmacies, such as the pharmacy server 142 of the third party site 140 (FIG. 1). The pharmacy links server 360 therefore enables fast and effective filling out of patients' prescriptions. The pharmacy links server 360 includes a request retrieval module 3202 and a communicator module 3204.

Figure 33:
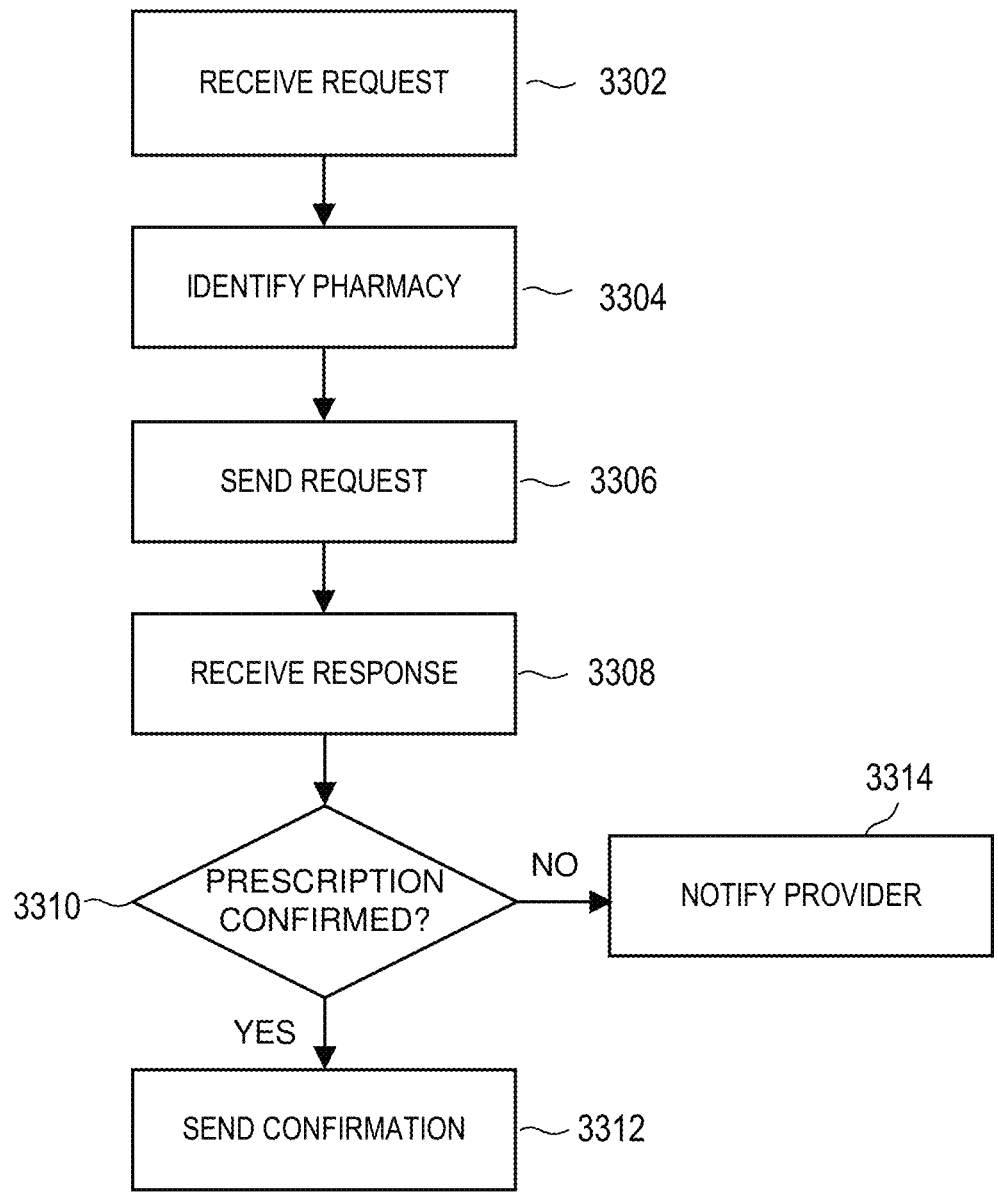
FIG. 33 is a flowchart illustrating one embodiment of a process for enabling communication with a remote pharmacy.

FIG. 33 is a flowchart illustrating one embodiment of a process 3300 for enabling communication with a remote pharmacy. The request retrieval module 3202 of the pharmacy links server 360 receives 3302 a request to fill out or re-fill a prescription for a patient. The communicator module 3204 identifies 3304 the appropriate pharmacy and sends 3306 a request for a prescription to the identified pharmacy. In one embodiment, once the request is received, a response is sent by the pharmacy and received 3308 by the communicator module 3204. In one embodiment, the response contains information as whether the prescription request was successful. If the prescription was confirmed (3310—Yes), a confirmation is sent 3312 to the provider interface device 120. If the prescription was not confirmed, for example, if the medication is not available or if the pharmacy needs more information, a notification is sent 3314 to the provider interface device 120 indicating the failure to fill out the prescription.

Figure 34:
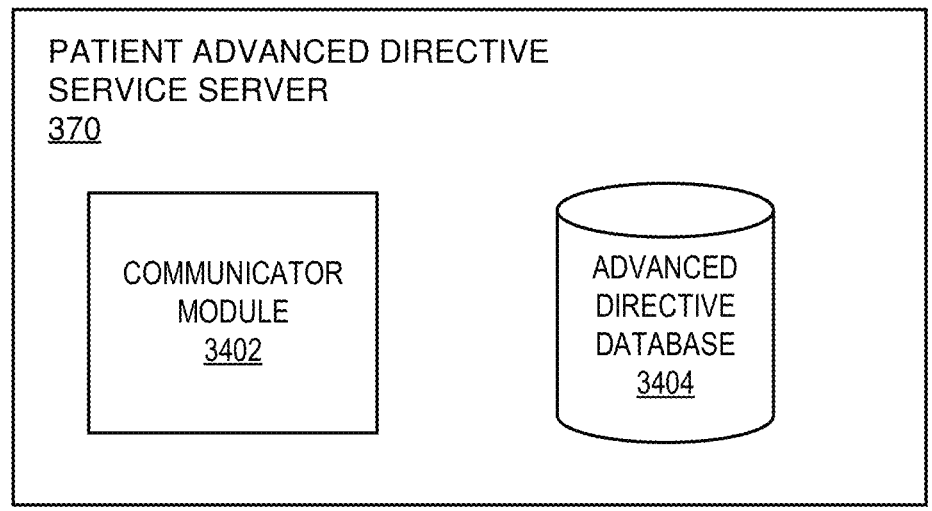
FIG. 34 is a block diagram illustrating an embodiment of a patient's advanced directive services server.

FIG. 34 is a block diagram illustrating an embodiment of a patient advanced directive services server 350. The patient advanced directive services server 350 provides storage for and secure access to a patient's advanced directive. The patient advanced directive services server 350 includes a communicator module 3402 and an advanced directive database 3404. The advanced directive database 3404 is a secure database that allows only authorized access.

Figure 35:
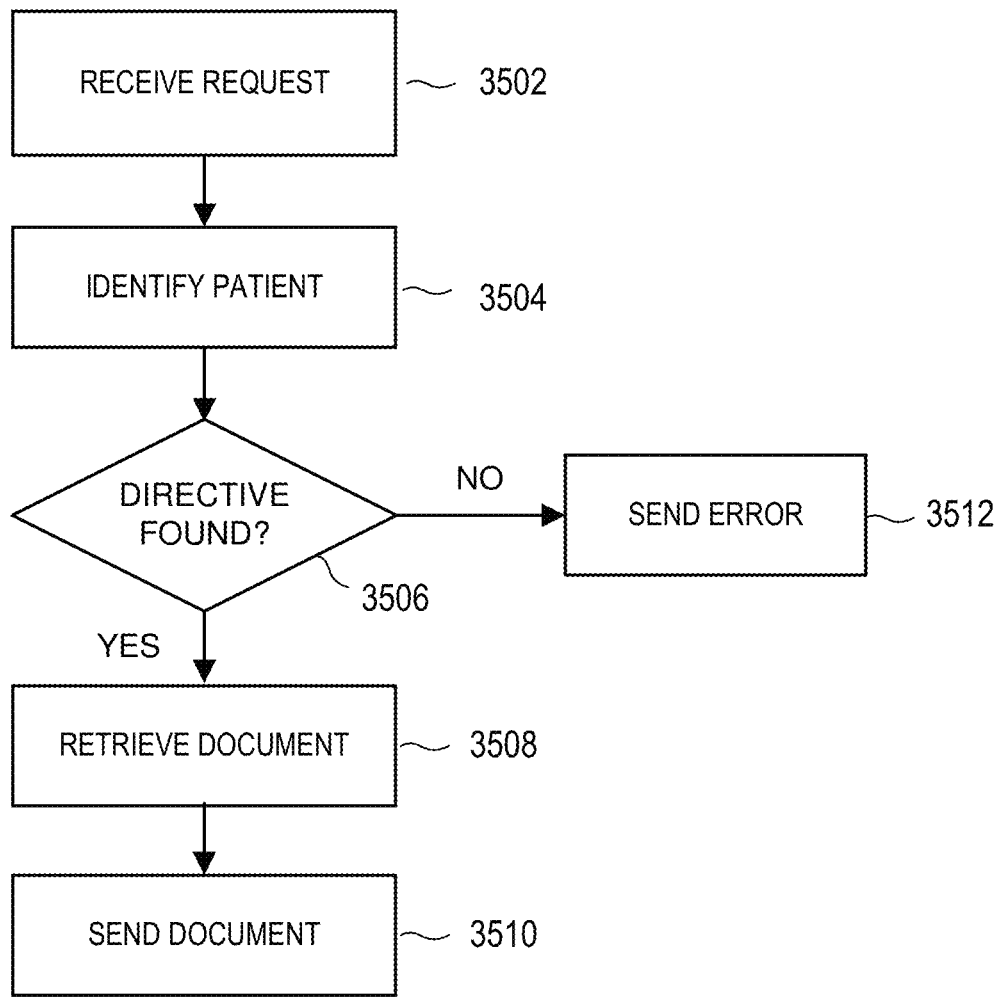
FIG. 35 is a flowchart illustrating one embodiment of a process for securely retrieving patient advanced directives.

FIG. 35 is a flowchart illustrating one embodiment of a process for securely retrieving patient advanced directives. The patient's advanced directive service server 350 receives 3502 a request for a patient's advanced directive. The patient is identified 3504 and a search is performed in the advanced directive database 3704. If the patients advanced is found (3506—Yes), the document is retrieved 350 and sent 3510 to the requestor. If the patients advanced is not found (3506—No), an error message is sent 3512 notifying the requestor that the advanced directive does not exist for the patient.

Figure 36:
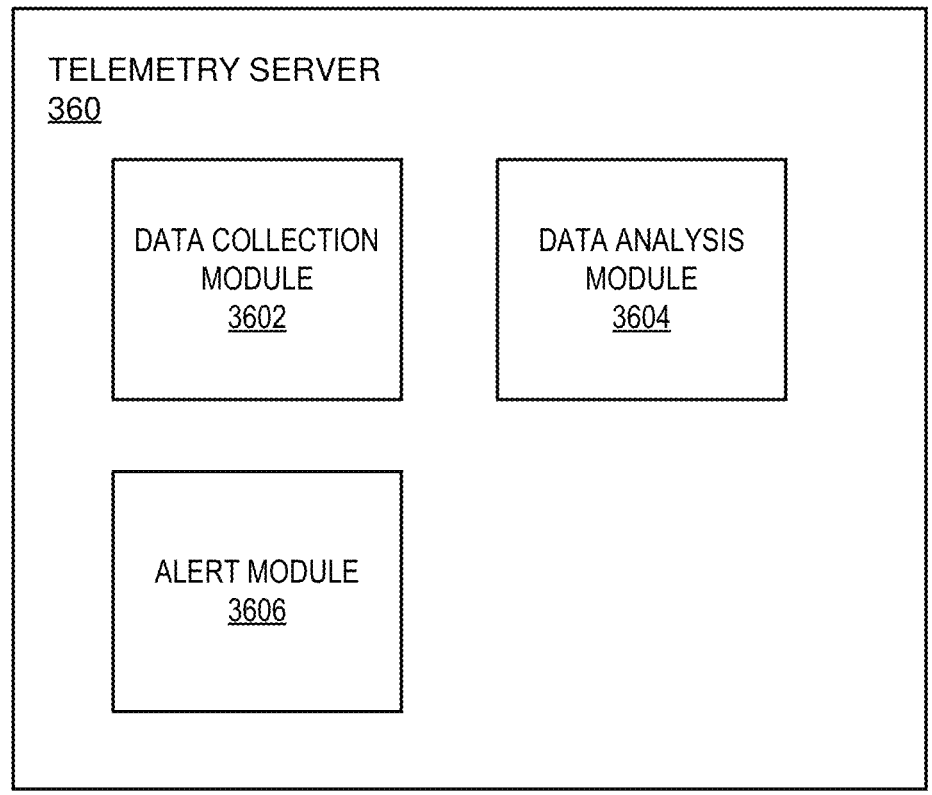
FIG. 36 is a block diagram illustrating an embodiment a telemetry server.

FIG. 36 is a block diagram illustrating an embodiment a telemetry server 260. The telemetry server 260 provides automatic updates and alerts for monitored patients presently located in a healthcare facility. The telemetry server 260 includes a data collection module 3602, a data analysis module 3604 and an alert module 3606. The data collection module 3602 is configured to receive patient status data from readers 108 located throughout the healthcare facility and is coupled to the data analysis module 3604, which is further coupled to the alert module 3606. The data analysis module 3604 receives the patient status data from the data collection module 3602 and processes the data to determine whether notifications should be sent. The alert module 3606 receives information from and sends it to one or more PDK 102 and/or provider interface devices 120.

In one embodiment, a telemetry monitor (not shown) continuously monitors a patient's status. In such embodiments, the PDK 102 is configured to wirelessly communicate with the telemetry monitor, which sends information to the PDK 102 to therefore be sent to the telemetry server 260. In another embodiment, the telemetry monitor is integrated into the PDK 102. In yet another embodiment, the telemetry monitor is configured to wirelessly communication with the Reader 108 or reader 720 of the provider interface device 120. In some embodiments, the telemetry monitor is integrated into the Reader 108 or the reader 720 of the provider interface device 120.

In one embodiment, automatic updates and alerts are available for monitored patients presently located in a healthcare facility. In such embodiments, Readers 108 automatically scans every monitored patient at regular intervals. The monitor data is compared to suggested normal data for each patient and when problems are detected, immediate alerts are issued to the appropriate individuals or areas within the healthcare facility. The monitored data is also automatically collected and stored.

Figure 37:
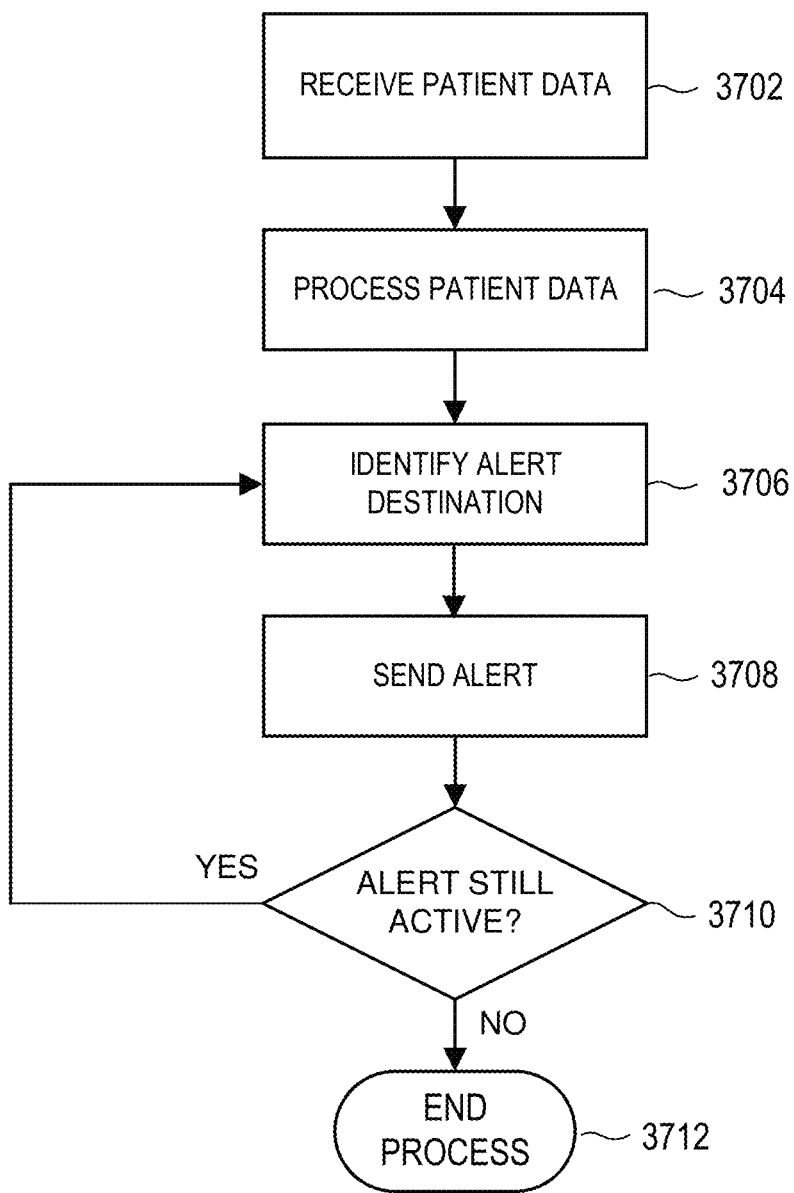
FIG. 37 is a flowchart illustrating one embodiment of a process for providing automatic updates and alerts for monitored patients.

FIG. 37 is a flowchart illustrating one embodiment of a process 3700 for providing automatic updates and alerts for monitored patients. The data collection module 3602 is receives 3702 patient status data from readers 108 located throughout the healthcare facility. The data analysis module 3604 receives the patient status data from the data collection module 3602 and processes 3704 the data to determine whether notifications should be sent. The alert module 3606 receives information from identifies 3706 the alert destination and sends 3708 it to the identified alert destination. A determination 3710 is made as to whether the alert is still active. If the alert is not active (3710—No) (i.e. there has been a response to the patient or the alert was deactivated at the alert destination), the process ends 3712. If the alert is still active (i.e. there has been no response to the patient or the alert was not deactivated at the alert destination) (3710—Yes), another alert destination is identified 3706 and the process repeats until the alert is no longer active. In one embodiment, if the alert is still active, the alert destination is broadened, for example, to be distributed to a wider area of coverage.

For example, a patient in the Intensive Care Unit (ICU) is continuously monitored to ensure a stable health status. If the electrocardiogram (EKG) machine detects that the patient's heart activity is abnormal, an alert is sent to the nurse's station. If a nurse sees the alert and responds to the patient, the nurse can deactivate the alert and the notification process ends. However, if no one is at the nurse's station, and the alert remains activated, another alert is sent to the PDK 102 of the patient's doctor. Further, if the patient's doctor does not respond and deactivate the alert, the alert may be broadened to be broadcasted to an entire unit, department, wing, floor or facility. In some embodiments, the alerts are continuously sent until a provider or other healthcare provider responds to the patient or deactivates the alert. In other embodiments, the patient can be monitored whether or not the patient is currently in their hospital room.

The order in which the steps of the methods of the present invention are performed is purely illustrative in nature. The steps can be performed in any order or in parallel, unless otherwise indicated by the present disclosure. The methods of the present invention may be performed in hardware, firmware, software, or any combination thereof operating on a single computer or multiple computers of any type. Software embodying the present invention may comprise computer instructions in any form (e.g., source code, object code, interpreted code, etc.) stored in any computer-readable storage medium (e.g., a ROM, a RAM, a magnetic media, a compact disc, a DVD, etc.). Such software may also be in the form of an electrical data signal embodied in a carrier wave propagating on a conductive medium or in the form of light pulses that propagate through an optical fiber.

While particular embodiments of the present invention have been shown and described, it will be apparent to those skilled in the art that changes and modifications may be made without departing from this invention in its broader aspect.

In the above description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to an apparatus for performing the operations herein. This apparatus can be specially constructed for the required purposes, or it can comprise a general-purpose computer selectively activated or reconfigured by a computer program stored in the computer. Such a computer program can be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and modules presented herein are not inherently related to any particular computer or other apparatus. Various general-purpose systems can be used with programs in accordance with the teachings herein, or it may prove convenient to construct more specialized apparatuses to perform the method steps. The required structure for a variety of these systems will appear from the description below. In addition, the present invention is not described with reference to any particular programming language. It will be appreciated that a variety of programming languages can be used to implement the teachings of the invention as described herein. Furthermore, as will be apparent to one of ordinary skill in the relevant art, the modules, features, attributes, methodologies, and other aspects of the invention can be implemented as software, hardware, firmware or any combination of the three. Of course, wherever a component of the present invention is implemented as software, the component can be implemented as a standalone program, as part of a larger program, as a plurality of separate programs, as a statically or dynamically linked library, as a kernel loadable module, as a device driver, and/or in every and any other way known now or in the future to those of skill in the art of computer programming. Additionally, the present invention is in no way limited to implementation in any specific operating system or environment.

It will be understood by those skilled in the relevant art that the above-described implementations are merely exemplary, and many changes can be made without departing from the true spirit and scope of the present invention.

What is claimed is:

1. A method comprising:
   determining, by a reader device, that a first portable electronic device associated with a patient and a second portable electronic device associated with a healthcare provider are located within a proximity zone of the reader device;
   wirelessly receiving, at the reader device, private healthcare data associated with the patient from the first portable electronic device located within the proximity zone of the reader device responsive to a successful biometric verification of the patient at the first portable electronic device;

wirelessly receiving, at the reader device, user credentials associated with the healthcare provider from the second portable electronic device located within the proximity zone of the reader device responsive to a successful biometric verification of the healthcare provider at the second portable electronic device;

automatically logging into a healthcare provider device associated with the reader device based on the user credentials;

sending the private healthcare data from the reader device to a server for performing an audit, the private healthcare data being accessible to the reader device as long as the first portable electronic device and the second portable electronic device are located within the proximity zone of the reader device, the server generating a recommendation for patient care based on performing the audit;

receiving, at the reader device, the recommendation; and presenting the recommendation on the healthcare provider device associated with the reader device.

2. The method of claim 1, further comprising:
receiving, at the reader device, a notification of an appointment check-in by the patient responsive to the successful biometric verification of the patient; and
presenting the notification of the appointment check-in by the patient on the healthcare provider device associated with the reader device.

3. The method of claim 1, wherein one or more of the reader device, the first portable electronic device, and the second portable electronic device further comprise:
a biometric reader configured to obtain a representation of a physical or a behavioral characteristic derived from one of the patient and the healthcare provider.

4. The method of claim 1, wherein automatically logging into the healthcare provider device associated with the reader device further comprises:
presenting a login window on the healthcare provider device;
retrieving the user credentials associated with the healthcare provider from the second portable electronic device; and
automatically entering the user credentials into the login window.

5. The method of claim 1, wherein one or more of the first portable electronic device and the second portable electronic device are integrated into at least one of a cell phone, an identification badge, a wearable device, a clothing item or a jewelry item.

6. The method of claim 5, further comprising:
receiving, at the reader device, annotation of the private healthcare data made by the healthcare provider on the healthcare provider device; and
sending the annotation of the private healthcare data from the reader device to the first portable electronic device for storage.

7. The method of claim 1, wherein sending the private healthcare data from the reader device to the server for performing the audit further comprises:
sending the private healthcare data from the reader device to the server for performing quality assurance analysis, the quality assurance analysis including comparing the private healthcare data with a preferred practice database defining appropriate care routines and identifying the recommendation for the patient care based on the comparing.

8. The method of claim 1, further comprising:
receiving, at the reader device, a first identification code uniquely identifying the first portable electronic device and a second identification code uniquely identifying the second portable electronic device responsive to determining that the first portable electronic device and the second portable electronic device are located within the proximity zone of the reader device.

9. The method of claim 1, wherein determining that the first portable electronic device associated with the patient and the second portable electronic device associated with the healthcare provider are located within the proximity zone of the reader device comprises detecting whether the first portable electronic device and the second portable electronic device are located within the proximity zone of the reader device for at least a predetermined period of time.

10. The method of claim 1, wherein the private healthcare data includes one or more of patient name, patient identification number, patient address, patient treatment and surgical history, prescribed and administered medications, reason for patient office visits, number of doctor visits, billing information, and insurance information.

11. A system comprising:
one or more processors; and
a memory including instructions that, when executed by the one or more processors, cause the system to:
determine, by a reader device, that a first portable electronic device associated with a patient and a second portable electronic device associated with a healthcare provider are located within a proximity zone of the reader device;
wirelessly receive, at the reader device, private healthcare data associated with the patient from the first portable electronic device located within the proximity zone of the reader device responsive to a successful biometric verification of the patient at the first portable electronic device;
wirelessly receive, at the reader device, user credentials associated with the healthcare provider from the second portable electronic device located within the proximity zone of the reader device responsive to a successful biometric verification of the healthcare provider at the second portable electronic device;
automatically log into a healthcare provider device associated with the reader device based on the user credentials;
send the private healthcare data from the reader device to a server for performing an audit, the private healthcare data being accessible to the reader device as long as the first portable electronic device and the second portable electronic device are located within the proximity zone of the reader device, the server generating a recommendation for patient care based on performing the audit;
receive, at the reader device, the recommendation; and
present the recommendation on the healthcare provider device associated with the reader device.

12. The system of claim 11, wherein the instructions, when executed by the one or more processors, further cause the system to:
receive, at the reader device, a notification of an appointment check-in by the patient responsive to the successful biometric verification of the patient; and present the notification of the appointment check-in by the patient on the healthcare provider device associated with the reader device.

13. The system of claim 11, wherein one or more of the reader device, the first portable electronic device, and the second portable electronic device further comprise:
a biometric reader configured to obtain a representation of a physical or a behavioral characteristic derived from one of the patient and the healthcare provider.

14. The system of claim 11, wherein to automatically log into the healthcare provider device associated with the reader device, the instructions, when executed by the one or more processors, further cause the system to:
present a login window on the healthcare provider device;
retrieve the user credentials associated with the healthcare provider from the second portable electronic device; and
automatically enter the user credentials into the login window.

15. The system of claim 11, wherein one or more of the first portable electronic device and the second portable electronic device are integrated into at least one of a cell phone, an identification badge, a wearable device, a clothing item or a jewelry item.

16. The system of claim 15, wherein the instructions, when executed by the one or more processors, further cause the system to:
receive, at the reader device, annotation of the private healthcare data made by the healthcare provider on the healthcare provider device; and
send the annotation of the private healthcare data from the reader device to the first portable electronic device for storage.

17. The system of claim 11, wherein to send the private healthcare data from the reader device to the server for performing the audit, the instructions, when executed by the one or more processors, further cause the system to:
send the private healthcare data from the reader device to the server for performing quality assurance analysis, the quality assurance analysis including a comparison of the private healthcare data with a preferred practice database defining appropriate care routines and identification of the recommendation for the patient care based on the comparison.

18. The system of claim 11, wherein the instructions, when executed by the one or more processors, further cause the system to:
at the reader device, receive a first identification code uniquely identifying the first portable electronic device and a second identification code uniquely identifying the second portable electronic device responsive to determining that the first portable electronic device and the second portable electronic device are located within the proximity zone of the reader device.

19. The system of claim 11, wherein to determine that the first portable electronic device associated with the patient and the second portable electronic device associated with the healthcare provider are located within the proximity zone of the reader device, the instructions, when executed by the one or more processors, further cause the system to detect whether the first portable electronic device and the second portable electronic device are located within the proximity zone of the reader device for at least a predetermined period of time.

20. The system of claim 11, wherein the private healthcare data includes one or more of patient name, patient identification number, patient address, patient treatment and surgical history, prescribed and administered medications, reason for patient office visits, number of doctor visits, billing information, and insurance information.

\* \* \* \* \*